US010632442B2

(12) United States Patent
Kim

(10) Patent No.: US 10,632,442 B2
(45) Date of Patent: Apr. 28, 2020

(54) APPARATUS FOR A MASS PRODUCTION OF MONODISPERSE BIODEGRADABLE POLYMER-BASED MICROSPHERES AND A MULTI-CHANNEL FORMING DEVICE INCORPORATABLE THEREIN

(71) Applicant: INVENTAGE LAB, INC., Seongnam-si, Gyeonggi-do (KR)

(72) Inventor: Ju Hee Kim, Gyeonggi-do (KR)

(73) Assignee: INVENTAGE LAB INC., Seongnam-si (KR)

( * ) Notice: Subject to any disclaimer, the term of this patent is extended or adjusted under 35 U.S.C. 154(b) by 253 days.

(21) Appl. No.: 15/788,930

(22) Filed: Oct. 20, 2017

(65) Prior Publication Data
US 2018/0133672 A1 May 17, 2018

Related U.S. Application Data

(60) Provisional application No. 62/421,501, filed on Nov. 14, 2016.

(51) Int. Cl.
*B01L 3/00* (2006.01)
*B01F 13/00* (2006.01)
(Continued)

(52) U.S. Cl.
CPC .............. *B01J 13/06* (2013.01); *A61K 9/0019* (2013.01); *A61K 9/146* (2013.01); *A61K 9/1647* (2013.01);
(Continued)

(58) Field of Classification Search
None
See application file for complete search history.

(56) References Cited

U.S. PATENT DOCUMENTS 7,553,434 B2 * 6/2009 Kawai ................... B01D 11/04
264/14
8,114,319 B2 * 2/2012 Davis ................... B01F 5/0646
264/11
(Continued)

FOREIGN PATENT DOCUMENTS

JP 2012011268 A 1/2012

OTHER PUBLICATIONS

Communication dated Mar. 20, 2018, issued by the Korean Intellectual Property Office in corresponding Korean Application No. 10-2018-7005510.

*Primary Examiner* — Mary Lynn F Theisen
(74) *Attorney, Agent, or Firm* — Sughrue Mion, PLLC

(57) ABSTRACT

A method and an apparatus for a large-scale production of monodisperse microspheres and biodegradable polymer-based drug delivery systems and design optimization method for the apparatus are provided. The method uses a plurality of microchips, each microchip having at least a first pathway, a second pathway and an outlet, wherein the first pathway and the second pathway merge at a cross point being one end of the outlet, and the method comprises preparing a polymer-phase solution including a degradable polymer and a water-phase solution including a surfactant, having the polymer-phase solution flow through the first pathway, having the water-phase solution flow through the second pathway, gathering a mixed solution flowing out of the outlet, and collecting the microspheres by filtering out the water-phase solution.

20 Claims, 93 Drawing Sheets

(51) Int. Cl.
  *B01J 19/00* (2006.01)
  *B01J 2/06* (2006.01)
  *B01J 13/06* (2006.01)
  *A61K 9/00* (2006.01)
  *A61K 9/16* (2006.01)
  *A61K 9/14* (2006.01)
  *A61K 31/365* (2006.01)
  *A61K 31/58* (2006.01)
  *C08J 5/00* (2006.01)
  *B01J 2/02* (2006.01)

(52) U.S. Cl.
  CPC ............ *A61K 31/365* (2013.01); *A61K 31/58* (2013.01); *B01F 13/0059* (2013.01); *B01F 13/0069* (2013.01); *B01L 3/502707* (2013.01); *C08J 5/00* (2013.01); *B01J 2/02* (2013.01); *B01J 2/06* (2013.01); *B01J 2219/00889* (2013.01); *B01L 2200/0647* (2013.01); *B01L 2300/0816* (2013.01); *B01L 2300/161* (2013.01); *C08J 2367/04* (2013.01)

(56) References Cited

U.S. PATENT DOCUMENTS

| | | | |
|---|---|---|---|
| 9,259,701 B2* | 2/2016 | Palmer | B01J 2/08 |
| 2003/0053934 A1* | 3/2003 | Andersson | B01F 5/0646 422/72 |
| 2005/0016851 A1* | 1/2005 | Jensen | B01F 5/0646 204/471 |
| 2005/0087122 A1* | 4/2005 | Ismagliov | B01F 5/0646 117/2 |
| 2005/0087767 A1* | 4/2005 | Fitzgerald | B01J 19/0093 257/200 |
| 2006/0014894 A1 | 1/2006 | Torii et al. | |
| 2010/0022680 A1* | 1/2010 | Karnik | A61K 47/6937 523/105 |
| 2010/0184928 A1* | 7/2010 | Kumacheva | B01F 3/0807 526/65 |
| 2015/0182964 A1* | 7/2015 | Samper | B01L 3/502746 137/1 |
| 2016/0271610 A1* | 9/2016 | Foulds | B01F 13/0062 |
| 2017/0145169 A1* | 5/2017 | Oakey | B01J 19/0093 |
| 2018/0355350 A1* | 12/2018 | Link | C12N 15/1075 |
| 2019/0099729 A1* | 4/2019 | Go | C08J 3/12 |
| 2019/0126230 A1* | 5/2019 | Ozasa | B01J 14/00 |

* cited by examiner

APPARATUS FOR A MASS PRODUCTION OF MONODISPERSE BIODEGRADABLE POLYMER-BASED MICROSPHERES AND A MULTI-CHANNEL FORMING DEVICE INCORPORATABLE THEREIN

BACKGROUND

This invention generally relates to an apparatus and a method for mass producing monodisperse microspheres including therein biodegradable polymers.

Pharmaceutical and bio-medical companies, in response to constant pressure to launch new products onto the market, are spending billions of dollars annually on developing ever more complex and sophisticated therapeutics. However, it is widely acknowledged that many of those therapeutics never reach the market. Even the most promising compound can fail clinical trials if unfavorable pharmacokinetics or poor delivery prevents it from reaching its site of action. Controlling the particulate characteristics of a drug formulation is an increasingly important consideration in pharmaceutical manufacturing, for it can improve a compound's probability of success by improving availability and reducing dosing.

For companies active in biological research, precise control over particle characteristics enables development of novel and sophisticated therapies with advanced drug-delivery systems, and one of such advanced drug-delivery systems currently being actively researched, developed and utilized is so called polymeric drug-delivery system (DDS), capable of, through the use of biodegradable, biocompatible and non-toxic polymers, such as, e.g., polylactic acid (PLA)/polyglycolic (PGA), providing a controlled release of therapeutic agents in constant doses over long periods, cyclic dosage, and tunable release of both hydrophilic and hydrophobic therapeutic agents (see FIG. 1).

One of the most well-known and representative medical products utilizing the polymeric drug-delivery system is Ellanse™ M from Aqutis/Sinclair, a medical product for tissue regeneration purposes. The product, i.e., Ellanse™ M, includes of monodisperse biocompatible and biodegradable polymeric microspheres, PLA being the active ingredient thereof, and as a consequence of the polymer, i.e., PLA, biodegrading over 2 year period, the tissue generation (or restoration or augmentation) effects of the product end up lasting over the same period of time, provided that the polymeric microspheres in the product are approximately of the same size, i.e., monodispersed.

The most widely used methods for a mass production of polymeric DDS, include phase separation, spray drying and solvent extraction-evaporation, as in the case of mass production of Ellanse™ M. It is, however, almost impossible to control the size of the polymeric microspheres using these processes, resulting in a wide particle size distribution, i.e., polydisperse. Since the optimum desired results of the product can be attained through a narrow microsphere size distribution or monodispersed, those microspheres of undesired sized, therefore, should be removed though a separate process, e.g., filtering, which, in turn, ends up, in addition to increasing the processing time, detrimentally affecting the final yield thereof.

SUMMARY

It is, therefore, an object of the present invention to provide an apparatus and a method for a large scale production of polymer-based drug delivery system based on microfluidics.

It is another object of the present invention to provide method for optimizing the designing of an apparatus and processes for mass production of monodisperse biodegradable polymer-based microspheres and biodegradable polymer-based drug delivery systems.

It is still another object of the present invention to provide an apparatus and a method for a mass production of microspheres incorporating therein biodegradable polymers.

It is a further object of the present invention to provide an apparatus and a method for a high yielding mass production of monodisperse biodegradable polymer-based microspheres and biodegradable polymer-based medical products.

It is yet further object of the present invention to provide an apparatus and a method for a high yielding mass production of monodisperse biodegradable polymer-based microspheres and biodegradable polymer-based medical products, the microspheres therein having a diameter ranging from 25 μm to 200 μm.

It is yet another object of the present invention to provide an apparatus and a method for a high yielding mass production of monodisperse biodegradable polymer-based microspheres and biodegradable polymer-based medical products, capable of providing a controlled release of therapeutic drug/agent incorporated therein, the microspheres therein having a diameter ranging from 25 μm to 200 μm.

It is still another object of the present invention to provide an apparatus and a method for a mass production of microspheres incorporating therein a biodegradable polymer for use in medical fillers, capable of providing a controlled biodegradation of the biodegradable polymer.

It is still another object of the present invention to provide an apparatus and a method for a mass production of biodegradable polymer-based microspheres incorporating therein a biodegradable polymer and a heartworm preventive drug/agent for use in heartworm preventives, capable providing a controlled release of the heartworm preventive drug/agent.

It is still another object of the present invention to provide an apparatus and a method for a mass production of microspheres incorporating therein a biodegradable polymer and a hair loss preventive drug/agent for use in hair loss preventives, capable of providing a controlled release of the hair loss preventive drug/agent.

In accordance with one aspect of the present invention, there is disclosed a method for design optimization of an apparatus for a large-scale production of monodisperse microspheres and biodegradable polymer-based drug delivery systems and process optimization using therewith, wherein the apparatus comprising a multichannel microsphere forming unit for initially generating the monodisperse microspheres and biodegradable polymer-based drug systems of a desired diameter and shape including therein at least two microchannels with a fixed dimension and at least two solutions, one solution known as a first solution and the other, a second solution, the first solution and the second solution being immiscible with respect to each other, one of the solutions including at least one biodegradable polymer dissolved therein in a predetermined amount, respectively known as a biodegradable polymer concentration, and the other solution including at least one surfactant dissolved therein in a predetermined amount, respectively known as a surfactant concentration, each of the solutions flowing in the respective microchannel at a constant flow rate, known respectively as a biodegradable polymer solution flow rate and a surfactant solution flow rate, the microchannels flowing therein the biodegradable polymer solution and the surfactant solution merging with each other at a merging point at an angle, known respectively as the merging angle, to form an outflow microchannel, resulting in the formation of monodisperse microspheres at the merging point having the desired diameter and shape including therein the biodegradable polymers, the monodisperse microspheres flowing out of the apparatus through the outflow microchannel along with the biodegradable polymer solution and the surfactant solution, the formation of the monodisperse microspheres having the desired diameter and shape resulting from interaction of the immiscibility of the solutions with respect to each other, the presence of the surfactant and the concentration thereof in the surfactant solution, the concentration of the biodegradable polymer in the biodegradable polymer solution, the merging angle, wettability between the solutions and the microchannel walls, the flow rate of the biodegradable polymer solution and the surfactant solution and the dimension of the microchannels, the method involving an optimization of the factors mentioned above, the method further comprising:

(1) determining the biodegradable polymer to be used and a first solvent in which the biodegradable polymer is to be dissolved, resulting in the biodegradable polymer solution, and determine the surfactant to be used and a second solvent in which the surfactant is to be dissolved, resulting in the surfactant solution, in such a way that the solutions are to be immiscible with respect to each other;

(2) fixing a material on which the microchannels to be formed, resulting in fixing of the wettability;

(3) fixing the diameter of the microspheres to be formed;

(4) fixing the dimension of the microchannels to be formed on the material by determining a relationship between the dimension and the diameter of the microspheres to be formed by forming the microspheres by varying the channel dimension while holding constant the flow rate of the biodegradable polymer solution, the flow rate of the surfactant solution, the biodegradable polymer concentration, the surfactant concentration and the merging angle;

(5) forming the microchannels on the materials to be incorporated in the multichannel microsphere forming unit in such a way that each of the biodegradable polymer solutions and the surfactant solutions flowing in the respective microchannels to flow an identical distance from an inlet of the multichannel microsphere forming unit to an outlet thereof, resulting in the flow rates of the biodegradable polymer solution and the surfactant solution within the respective microchannels in the multichannel microsphere forming unit to remain constant therethroughout;

(6) determining a relationship between the flow rate of the surfactant solution on the diameter of the microspheres to be formed by forming the microspheres by varying the flow rate of the surfactant concentration while holding constant the channel dimension, the flow rate of the biodegradable solution, the biodegradable polymer concentration, the surfactant concentration, the merging angle;

(7) determining a relationship between the flow rate of the biodegradable polymer solution on the diameter of the microspheres to be formed by forming the microspheres by varying the flow rate of the biodegradable polymer concentration while holding constant the channel dimension, the flow rate of the surfactant solution, the biodegradable polymer concentration, the surfactant concentration and the merging angle;

(8) determining a relationship between the surfactant concentration on the diameter of the microspheres to be formed by forming the microspheres by varying the surfactant concentration while holding constant the channel dimension, the flow rate of the surfactant solution, the flow rate of the biodegradable polymer solution, the biodegradable polymer concentration and the merging angle;

(9) determining a relationship between the biodegradable polymer concentration on the diameter of the microspheres to be formed by forming the microspheres by varying the surfactant concentration while holding constant the channel dimension, the flow rate of the surfactant solution, the flow rate of the biodegradable polymer solution, the biodegradable polymer concentration and the merging angle;

(10) determining a relationship between the merging angle on the diameter of the microspheres to be formed by forming the microspheres by varying the merging angle while holding constant the channel dimension, the flow rate of the surfactant solution, the flow rate of the biodegradable polymer solution, the biodegradable polymer concentration and the surfactant concentration; and

(11) determining the optimum design of the apparatus, including therein the multichannel microsphere forming unit, for the large scale production of the monodisperse microspheres and biodegradable polymer-based drug delivery systems of the desired diameter and shape incorporating therein the optimum merging angle and the optimum dimension of the microchannels determined through which the biodegradable polymer solution and the surfactant solution flow and the optimum processes to be used therewith incorporating therein the optimum flow rates of the biodegradable polymer solution and the optimum concentrations of the biodegradable polymer and surfactant in the respective solutions determined.

In accordance with another aspect of the present invention, there is disclosed an apparatus for a mass production of microspheres comprising: a multi-channel microsphere forming unit including a plurality of first microchannels through which a first source material is flowable, a plurality of second microchannels through which a second source material immiscible with the first material is flowable, a plurality of first merging point where the plurality of first microchannels and the plurality of second microchannels are merged and the microspheres initially get formed, and a plurality of third microchannels extending from the plurality of first merging points and through which a first mixed solution including therein the microspheres formed, the first source material and the second source material is flowable; a first source material reservoir containing the first source material and in fluid communication with the plurality of first microchannels; a second source material reservoir containing the second source material and in fluid communication with the plurality of second microchannels; a flow control unit configured to supply a first gas to the first source material reservoir at a first source material flow rate and to supply a second gas to a second source material reservoir at a second source material flow rate; and a product reservoir for accommodating the microspheres formed from the multi-channel forming unit, wherein the first source material contained in the first source material reservoir is delivered to the plurality of first microchannels of the multi-channel forming unit in a flow rate corresponding to the first source material flow rate of the first gas, and the second source material contained in the second source material reservoir is delivered to the plurality of second microchannels of the multi-channel forming unit in an flow rate corresponding to the second source material flow rate of the second gas, the first source material is delivered to the plurality of first microchannels at a constant first flow rate without fluctuation, and the second source material is delivered to the plurality of second microchannels at a constant second flow rate without fluctuation.

In accordance with yet another aspect of the present invention, there is disclosed a multi-channel microsphere forming device for forming microspheres from a first source material and a second source material immiscible with the first source material, the device comprising: an upper case including a first annular manifold formed on a side of the upper case, a second annular manifold radially inside of the first annular manifold on the side of the upper case, a first inlet line configured to deliver the first source material and the second inlet line configured to deliver the second source material to the second annular manifold, a second annular manifold formed on the side of the upper case radially inside of the first annular manifold; a lower case including a product exhausting hole formed at a center of the lower case; a lower multi-channel plate disposed on the lower case and including a plurality of first microchannels radially arranged and formed on a side of the lower multi-channel plate, a plurality of second microchannels radially arranged and formed on a side of the lower multi-channel plate, a plurality of third microchannels radially arranged and formed on a side of the lower multi-channel plate, and a center through-hole formed at a center of the lower multi-channel plate, wherein the plurality of first microchannels and the plurality of second microchannels are merged at a plurality of first merging points and the plurality of third microchannels are arranged in direction to center through-hole from the plurality of first merging points; and an upper multi-channel plate disposed between the upper case and the lower multi-channel plate, including a plurality of first channel connection holes disposed between the plurality of first microchannels and the first annular manifold, and a plurality of second channel connection holes disposed between the first annular manifold and the plurality of second microchannels.

In accordance with still another object of the present invention, there is disclosed a method for forming microspheres for use in medical fillers, the method comprising: preparing a first source material in which a surfactant is dissolved in water; preparing a second source material in which the biodegradable polymer is dissolved in an organic solvent; supplying the first source material and the second source material to multichannel forming unit in which the first source material flows through a plurality of first microchannels, the second source material flows through the plurality of second microchannels, the first source material and the second source material are mixed with each other at a plurality of merging points where the plurality of first microchannels and the plurality of second microchannels meet with each other, and a mixed solution of the first source material and the second source material flows through a plurality of third microchannels extending from the plurality of first merging points; forming, in the mixed solution, a plurality of microspheres including the biodegradable polymer and having a diameter of 0.4 to 1.4 times the diameter of a target size microspheres; and collecting a plurality of formed microspheres, wherein the width or height of the plurality of third microchannels is different from the diameter of the target size microspheres differ by less than 30%.

In accordance with yet still another object of the present invention, there is disclosed a method for forming microspheres with a biodegradable and a heartworm preventive drug for use in heartworm preventives, the method comprising: preparing a first source material in which a surfactant is dissolved in water; preparing a second source material in which the biodegradable polymer and the heartworm preventive are dissolved in an organic solvent; supplying the first source material and the second source material to multichannel forming unit in which the first source material flows through a plurality of first microchannels, the second source material flows through the plurality of second microchannels, the first source material and the second source material are mixed with each other at a plurality of merging points where the plurality of first microchannels and the plurality of second microchannels meet with each other, and a mixed solution of the first source material and the second source material flows through a plurality of third microchannels extending from the plurality of first merging points; forming, in the mixed solution, a plurality of microspheres including the biodegradable polymer and the heartworm preventive drug and having a diameter of 0.4 to 1.4 times the diameter of a target size microspheres; and collecting a plurality of formed microspheres, wherein the width or height of the plurality of third microchannels is different from the diameter of the target size microspheres by less than 30%.

It is still further another objective present invention, there is disclosed a method for forming microspheres with a biodegradable polymer and hair loss preventive drug for use in a hair loss preventive, the method comprising: preparing a first source material in which a surfactant is dissolved in water; preparing a second source material in which the biodegradable polymer and the hair loss preventive drug are dissolved in an organic solvent; supplying the first source material and the second source material to multichannel forming unit in which the first source material flows through a plurality of first microchannels, the second source material flows through the plurality of second microchannels, the first source material and the second source material are mixed with each other at a plurality of merging points where the plurality of first microchannels and the plurality of second microchannels meet with each other, and a mixed solution of the first source material and the second source material flows through a plurality of third microchannels extending from the plurality of first merging points; forming, in the mixed solution, a plurality of microspheres including the biodegradable polymer and the finasteride and having a diameter of 0.4 to 1.4 times the diameter of a target size microspheres; and collecting a plurality of formed microspheres, wherein the width or height of the plurality of third microchannels is different from the diameter of the target size microspheres by less than 30%.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, not is every component of each embodiment of the invention shown where illustration is not necessary to allow those of ordinary skill in the art to understand the invention. In the figures:

FIGS. 66A to 65C illustrate SEM images of the Test Product (DOP-12) incorporating therein the biodegradable polymer (PLGA) at a concentration of 40 weight %, 50 weight % and 60 weight %, respectively.

DETAILED DESCRIPTION

This invention generally relates to an apparatus and a method for a large scale production of microspheres incorporating therein biodegradable polymers; and more particularly to an apparatus and a method for a high yielding large scale production of monodisperse microspheres and biodegradable polymer-based medical products based on microfluidics which is a multidisciplinary field dealing with the behavior, precise control and manipulation of fluids that are geometrically constrained to typically a small scale, having one of the following features:

(1) small volumes (µL, nL, pL, fL)
(2) small size
(3) low energy consumption
(4) effects of the micro domain Droplet-based HCMMM (Highly Controlled Method for Mass-production of Mcrospheres) is a rapidly growing interdisciplinary field of research combining soft matter physics, biochemistry and microsystems engineering, and is deemed to be a method having the distinction of manipulating discrete volumes of fluids in immiscible phases with low Reynolds number and laminar flow regimes. Interest in droplet-based HCMMM systems has been growing substantially in past decades. Droplet-based HCMMM of the present invention offers the feasibility of handling miniature volumes of fluids conveniently, providing better mixing and is deemed suitable for high throughput experiments/mass production of polymeric DDS.

Figure 1:
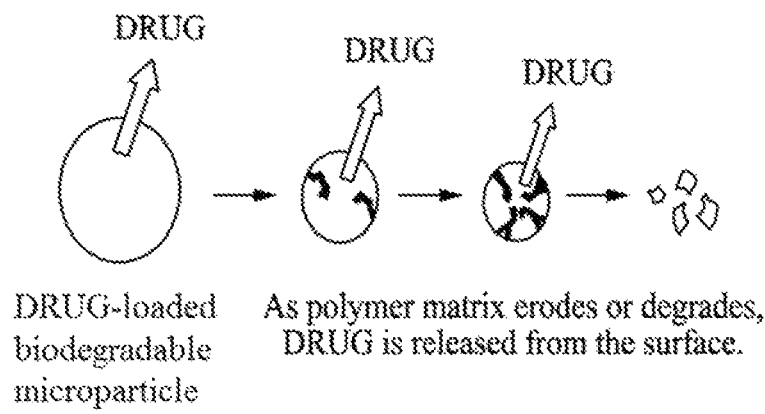
FIG. 1 illustrates a Biodegradable Microsphere loaded with Drug.

Currently, researches into drug delivery systems seeking to improve the pharmacological activity of therapeutic agents, i.e., active ingredients, by enhancing pharmacokinetics (absorption, distribution, metabolism and excretion) and also by amending pharmacodynamic properties, such as the mechanism of action, pharmacological response, and affinity to the site of action are actively being carried out, and one of such a research involves the use of polymers, as (1) a therapeutic agent carrier to the site of action, in drug delivery, the therapeutic agent being protected from interacting with other molecules which could cause a change in the chemical structure of the active ingredient causing it to lose its pharmaceutical action; and (2) a therapeutic agent vehicle for providing a controlled release thereof (see FIG. 1 below). Moreover, polymeric carriers avoid the interaction of the therapeutic agent with macromolecules such as proteins, which could sequester the active ingredient preventing its arrival at the action place.

If a polymer is to be used as a carrier, the next step is to design a type of polymeric structure that will permit obtaining the desired release conditions. Therefore, the polymeric structure should be: i) biodegradable, because the chemical bonds that make up its chemical structure break; ii) disassemblable, because the various pieces forming the polymer disassemble but the chemical bonds do not break; and iii) undisassemblable, because the chemical bonds do not disassemble or break, that is, the polymer remains unchanged. In the first two cases, micro-sized polymeric carriers could be used. However, if the polymeric structure of the polymer is neither biodegradable nor disassemblable, then nano-sized polymers should preferably be used.

In the case of biodegradable polymers, another option to consider in their design is the chemical structure of the polymer (degree of hydrophobicity, covalent bonds between monomers, etc.), since the speed and degradation condition, and therefore, the rate and the site of therapeutic agent release, can be modulated depending on the chemical structure of the polymer used.

An attempt was made by the inventor(s) to combine the ideas presented hereinabove to develop an apparatus and a method for a large scale-production of biodegradable polymer-based monodisperse microspheres.

Figure 2:
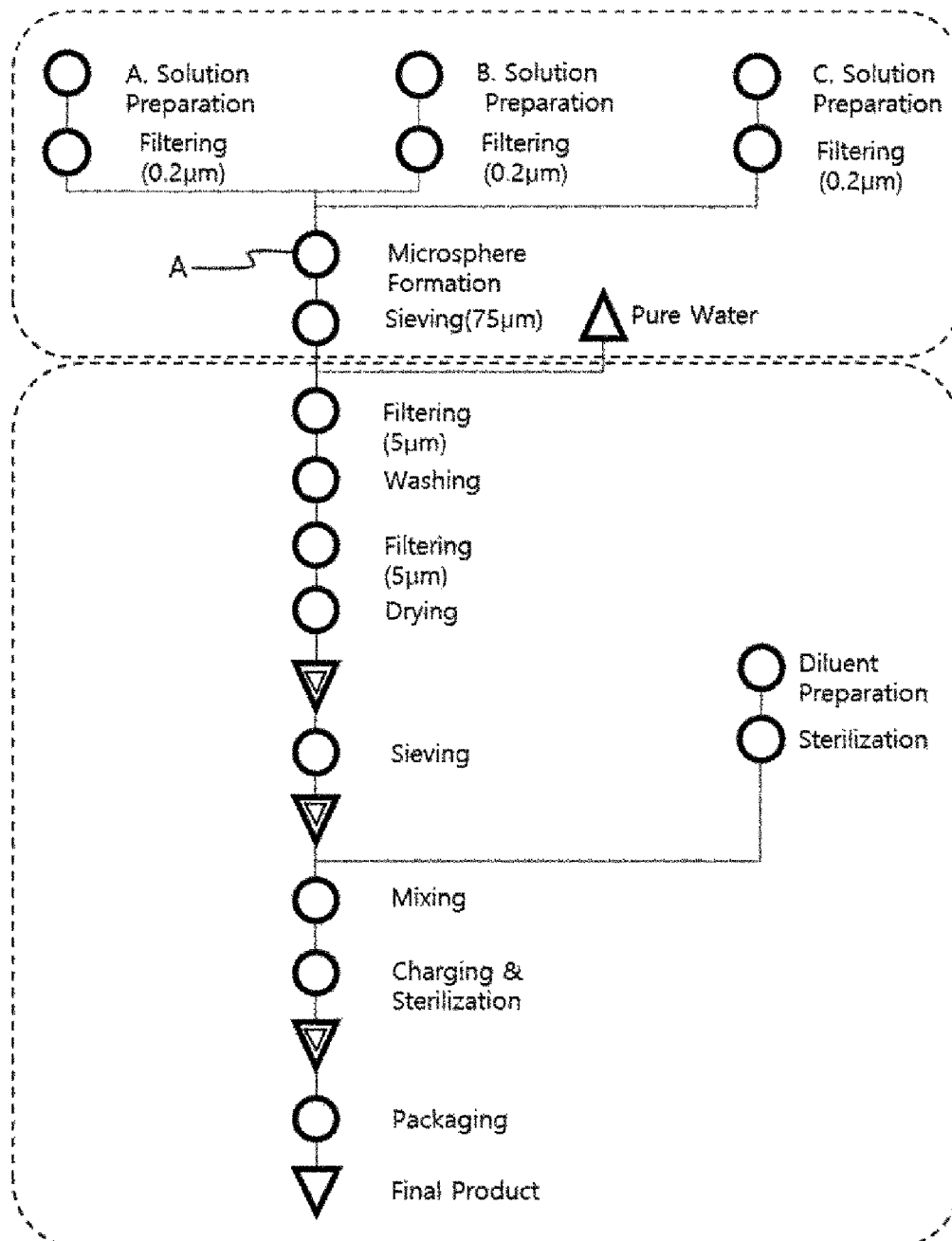
FIG. 2 is a Process Flow Chart & Apparatus Layout (Lab-scale).

Shown in FIG. 2 is the process flow chart and the layout of the apparatus for a lab-scale production of biodegradable polymer-based monodisperse microspheres based on HCMMM, respectively, wherein the process includes: (1) Preparing a biodegradable polymer-based solution including therein the biodegradable polymer and a water-phase solution including therein a surfactant; (2) Filtering the solutions prepared for a sterilization purpose; (3) Preparing biodegradable polymer-based microspherical droplets by forcing the filtered solutions, i.e., the filtered biodegradable polymer solution and the filtered water-phase solution into a microchip (A in FIG. 3); (4) Sieving and filtering the biodegradable polymer-based microspherical droplets; (5) Washing the sieved and filtered biodegradable polymer-based microspherical droplets with pure water; (6) Filtering the biodegradable polymer-based microspherical droplets washed with pure water; (7) Drying the biodegradable polymer-based microspherical droplets; (8) Filtering the biodegradable polymer-based microspherical droplets to obtain the biodegradable polymer-based microspheres of a desired size, i.e., monodisperse; (9) Mixing the biodegradable polymer-based microspheres with a diluent that has been sterilized; (10) Charging and Sterilizing the biodegradable polymer-based microspheres that have been mixed; and (11) Packaging the biodegradable polymer-based microspheres that have been charged and sterilized to obtain the final product. The steps (1) through (8) describe the method for producing monodisperse biodegradable polymer-based microspheres, and the steps (9) though (11) can be changed, modified or omitted depending on the final product desired. The steps shown in FIG. 2 are the steps required to produce medical fillers including therein monodisperse biodegradable polymer-based microspheres having a diameter of 50 µm, meaning that the specification of the filters and the sieves shown in FIG. 2 can be changed depending on the requirements of the final product. Although steps (1) through (3) can be performed in a clean room of class 10,000, steps (3) though (11) should be performed in a clean room of class 100. The biodegradable polymer is dissolved in an oil-based solvent or organic solvent and the surfactant, in pure water, making the solutions prepared immiscible with respect to each other. The solution including therein the biodegradable polymer and the solution including therein the surfactant will, henceforth, be known as the biodegradable polymer solution and the water-phase solution, respectively and the solutions, without saying, are immiscible, with the respect to one another.

The biodegradable polymers used in the present invention are selected from the group consisting of: polylactic acid (PLA), polyglycolic acid (PGA), poly (lactic acid-glycolic acid), polycaprolactone and their derivative groups, preferably polycaprolactone (PCL), but not limited thereto. The number average molecular weight of the above biodegradable polymers is not particularly limited, but ranges at between 5,000 and 300,000, preferably between 8,000 and 250,000, and more preferably between 10,000 and 200,000.

The boiling point of the organic solvent used in the present invention should be less than 120° C. and is immiscible with water. For example, it is selected from the group consisting of: dichloromethane, chloroform, chloroethane, dichloroethane, trichloroethane and their mixture groups, preferably dichloromethane, but not limited thereto.

The type of the surfactants used in the present invention is not particularly limited, provided that it can facilitate a stable emulsification of the biodegradable polymer solutions. Specifically, it is selected from the group consisting of: nonionic surfactant, anionic surfactant, cationic surfactant, and their mixture groups, more specifically the group consisting of: methylcellulose, polyvinylpyrrolidon, lecithin, gelatin, polyvinyl alcohol, polyoxyethylene sorbitan fatty acid ester, polyoxyethylene castor oil derivative, sodium lauryl sulfate, sodium stearate, ester amine, linear diamine, fatty amine and their mixture groups, and preferably polyvinyl alcohol (PVA), but not limited thereto.

Figure 3:
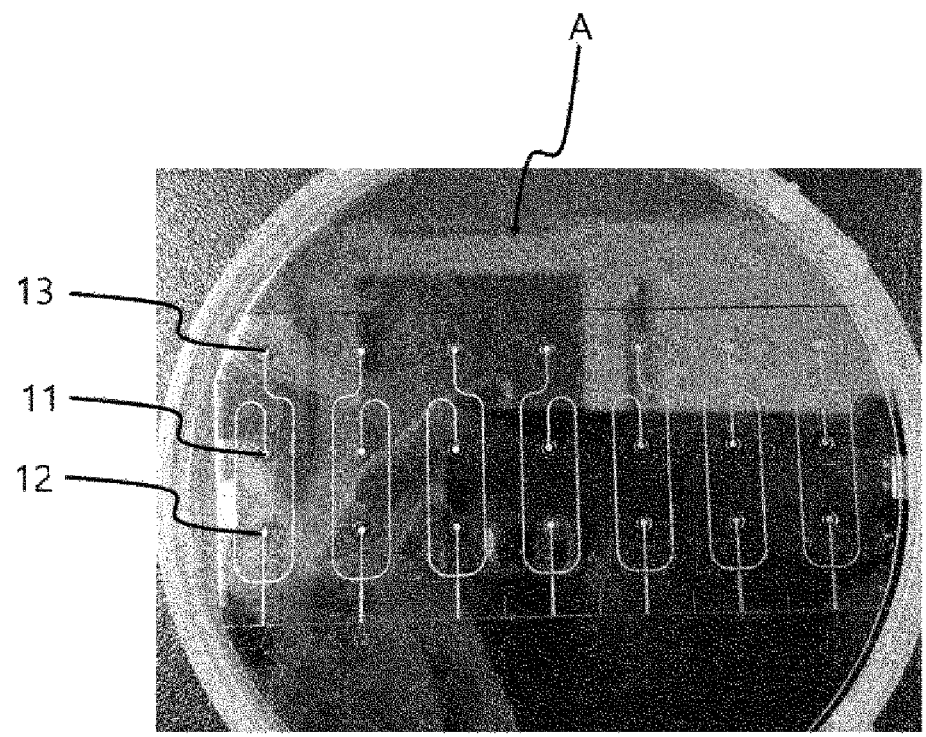
FIG. 3 illustrates a Microchip Design viewed from the top (Photo).
Figure 4:
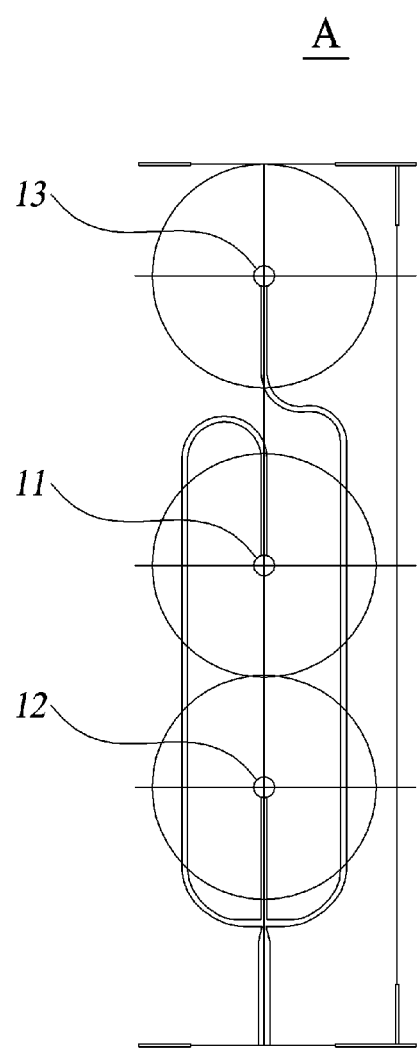
FIG. 4 illustrates a Microchip Design (Top View).
Figure 5:
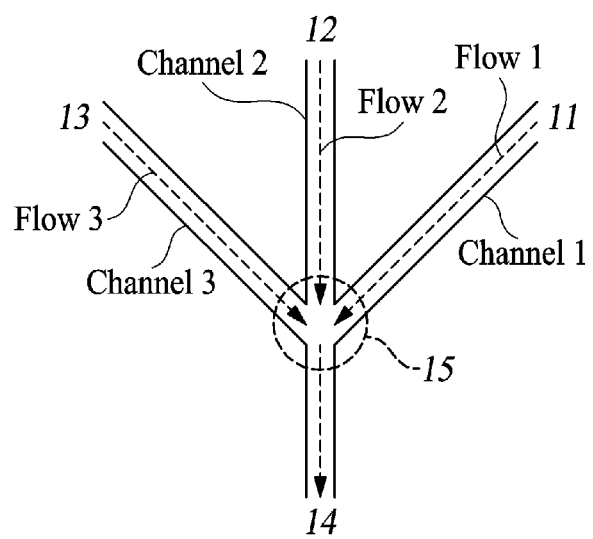
FIG. 5 is a schematic diagram of the Microchip and the Flows established therein.

One of the most critical importance issues in producing of monodisperse biodegradable polymer-based microsphere is the design of the microchip to be used, incorporating therein a plurality of microchannels based on HCMMM principles, the microchannels being the pathways through which the biodegradable polymer-phase solution and the water-phase solution prepared in the steps described hereinabove, and a solution including therein biodegradable polymer-based microspherical droplets formed flow, and FIGS. 3, 4 and 5 are a photo of the lab scale microchip used, a schematic diagram of the microchip viewed from the top and a simplified drawing at the crossing point of the microchannels therein, respectively. The microchip initially used in the present invention, as shown in FIGS. 3, 4 and 5, comprises three microchannels, i.e., 1, 2 and 3 in FIG. 5, one of the microchannles being the pathway through which the biodegradable polymer solution flows, i.e., Flow 2, in FIG. 5 and the remaining two microchannles, the pathway through which the water-phase solution flow, i.e., Flow 1 and Flow 3 in FIG. 5, the microchannel accommodating the flow of the biodegradable polymer solution being located between the microchannels accommodating the flow of the water-phase solution, the microchannels accommodating the flow of the water-phase solution merging with the microchannel accommodating the flow of the biodegradable polymer-phase solution at a merging point, i.e., 15, in FIG. 5, at an angle Ø, the merging point being the location where biodegradable polymer-based microspherical droplets get formed due to the interaction of the solutions flowing in the microchannels and the immiscibility of the solutions flowing through the microchannels meeting thereat, the microchannels accommodating the flows of the water-phase solution having just an inlet, i.e., 11 and 13 in FIGS. 3, 4 and 5, respectively, through which the solution enters the microchannel and the microchannel accommodating the flow of the biodegradable polymer-phase solution having an inlet, i.e., 12, in FIGS. 3, 4 and 5, and an outlet, i.e., 14, in FIG. 5, the solution including the biodegradable polymer-based microspherical droplets flowing out of the microchip though the outlet, i.e., 14 in FIG. 5. The number of microchannels in the microchip for accommodating the flows of the solutions can vary depending on the requirements of the final product. The solution including the biodegradable polymer-based microspherical droplets will henceforth be referred as the dispersed phase solution.

In the present invention, the water-phase solution enter the microchip A through the inlets 11 and 13, respectively, thereby establishing Flow 1 and the Flow 3 in the microchannels 1 and 3, respectively, and meets Flow 1 of the biodegradable polymer-phase solution at an angle between 30° and 90° at the merging point 15, where the microspherical droplets are formed due to the segmentation of the biodegradable polymer solution, i.e., Flow 2, by the water-phase solution, i.e., Flow 1 and Flow 3, and immiscibility of the two solutions, resulting in the formation of the dispersed phase solution, including therein the microspherical droplets formed at the merging point 15, which flows out of the microchip through the outlet 14.

In the microchip of the present invention, the microchannels therein were formed using a deep reactive ion etching (DRIE) method, i.e., by etching, on a silicon wafer in a vertical direction and anodically bonding glass thereon. The DRIE method is better suited than wet etching in forming the microchannels, for it enables vertical etching and can also provide a smooth surface when etching for 50 μm or deeper is required. Although, the microchannels of the present invention are formed on a silicon wafer, they can also be formed on glass, steel or on hydrophobic polymer wafer, such as PDMS. For example, the advantages of using these particular polymer surfaces are several. They are completely bioinert and antifouling, making them ideally suited for biopharmaceutical processing and manufacturing. The wafer chips themselves are relatively inexpensive and completely disposable. What is most important, the polymers enable establishment of segmented flow conditions with a high level of stability and reliability, allowing the mass production of monodisperse biodegradable polymer-based microspheres possible.

It has been experimentally determined that if the water-phase solution entering the microchip A through the inlets 11 and 13, respectively, thereby establishing Flow 1 and Flow 3 in the microchannels 1 and 3, respectively, meet the flow of the biodegradable polymer-phase solution, i.e., Flow 1 at an angle of either less than 30° or greater than at an angle 90°, it leads to widening of the size distribution of the microspherical droplets formed, i.e., polydisperse microspherical droplets. Accordingly, to obtain microspherical droplets with a narrow size distribution, i.e., monodisperse microspherical droplets, the angle at which the flows of the water phase solution merge with the flow of the biodegradable polymer solution, i.e., Ø, should be set between 30° and 90°.

There are a number of parameters that need to be controlled in order to obtain the desired objective, and it has been determined through the experiments by the inventor(s) that the critical/important parameters are the flow rate of the incoming flows, the viscosity of the incoming flows, the surfactant concentration in one of the incoming flows, the biodegradable polymer concentration in the other incoming flow, the channel wall wettability and the channel dimensions, and of the critical/important parameters mentioned, it is possible to "fix" the channel wall wettability by setting the materials to be used for the microchip and the solutions for flowing through the microchannels and forming the microspherical droplets, and the viscosity, by fixing the fluids and the concentration of the biodegradable polymer and the surfactant incorporating therein, respectively, leaving the flow rate of the incoming flows, i.e., incoming flow including therein the biodegradable polymer and incoming flow(s) including therein the surfactant, the channel dimension and the concentration of the biodegradable polymers and the surfactant in the respective incoming flows, as the variables.

A series of experiments were performed to determine the effects of the variables mentioned above, starting with the determination of the effects of the concentration of the biodegradable polymers in the biodegradable polymer-phase solution and the surfactant in the water-phase solution, respectively.

In one embodiment of the present invention, the concentration of the surfactant in the water-phase solution has been varied between 0.10 and 0.50 weight % while holding the channel dimension and the incoming flow rates constant. In the surfactant concentration range specified, an increase in the concentration leads to a corresponding decrease in coagulation of the microspheres formed, leading to a narrow particle-size distribution due to a decrease in interfacial tension. If the surfactant concentration (PVA) of the water-phase solutions falls below 0.10 weight %, it results in widening particle-size distribution. However, if the concentration is 1.0 weight % or higher, it leads to a difficulty in washing and removing the surfactant from the microspheres obtained. It has further been experimentally determined that if the concentration of the surfactant is equal to or greater than 0.15 weight %, the effect thereof on the microsphere diameter becomes negligible up to 0.25 weight %, flattening out at around 0.30 weight %, as shown in Table 1 and FIG. 6. The optimum/ideal/realistic surfactant concentration in terms of the effectiveness and the cost factor, based on the experimental results, is between 0.15 weight % and 0.30 weight %.

TABLE 1

Effect of the Surfactant Concentration (weight %) on the Diameter of Microsphere (μm)

| Surfactant Concentration (wt %) | Microsphere Diameter (μm) |
|---|---|
| 0.10 | 59.4 |
| 0.15 | 49.8 |
| 0.20 | 49.5 |
| 0.25 | 49.5 |
| 0.30 | 49.4 |

Figure 7:
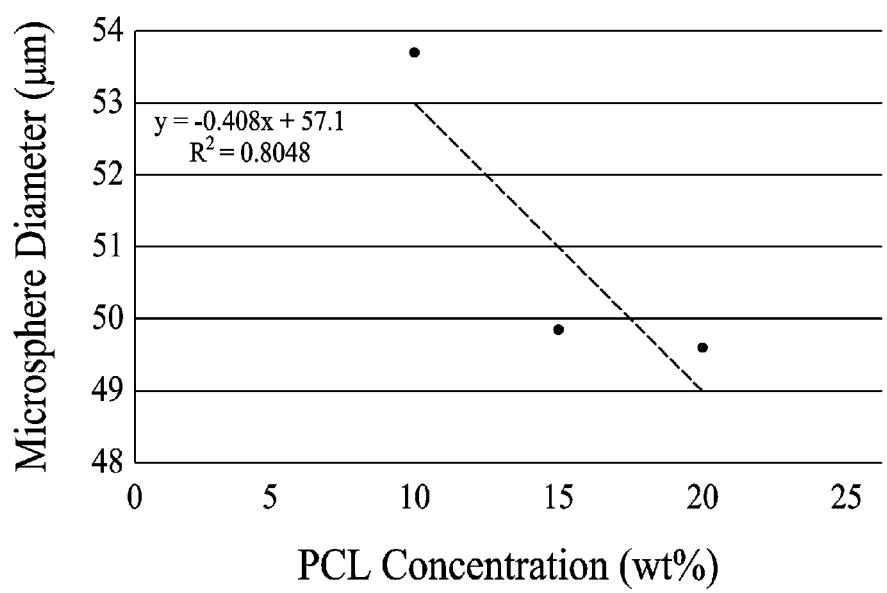
FIG. 7 illustrates the effect of the Biodegradable Polymer Concentration (weight %) on the Microsphere Diameter (μm).

Another set of experiments were performed to determine the effects of the concentration of the biodegradable polymers in the biodegradable polymer-phase solution by varying the concentration of the biodegradable polymer in the biodegradable polymer-phase solution between 5 and 30 weight % while holding the channel dimension and the flow rate of the incoming solutions constant. If the concentration of the biodegradable polymer is less than 5 weight %, it results in microspheres not being formed. If the concentration exceeds 30 weight %, it results in microspheres formed having non-spherical shape. There is shown in Table 2 and FIG. 7 shows the effects of the concentration of the biodegradable polymer (PCL) and the diameter of the microspheres formed.

TABLE 2

Effect of the Biodegradable Polymer Concentration (weight %) on the Microsphere Diameter (μm)

| PCL Concentration (wt %) | Microsphere Diameter (μm) |
|---|---|
| 10 | 53.6 |
| 15 | 49.8 |
| 20 | 49.5 |

Figure 6:
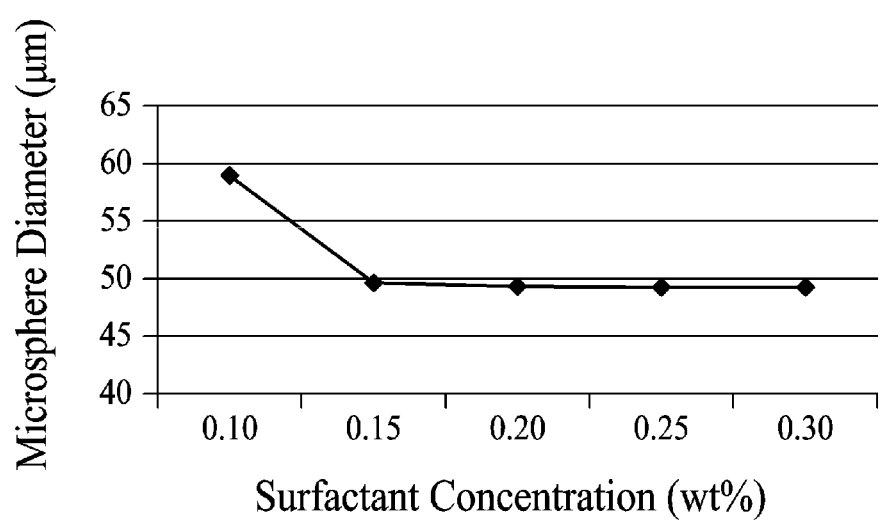
FIG. 6 illustrates the effect of the Surfactant Concentration (weight %) on the Microsphere Diameter (μm).

According to the results summarized in Table 2 and shown in FIG. 6, there is roughly a linear relationship existing between the concentration of the biodegradable polymer in the biodegradable polymer-phase solution and the microsphere diameter, as defined by the following relationship:

Microsphere Diameter=−0.408*(Biodegradable Polymer Concentration)+57.1 with a standard deviation of 0.8048.

Based on the experimental results, the biodegradable polymer concentration is between 5 weight % and 30 weight %, and the relationship developed can be used to "fine tune" the microsphere diameter, if not for all biodegradable polymers, at least for a PCL based system.

Figure 8:
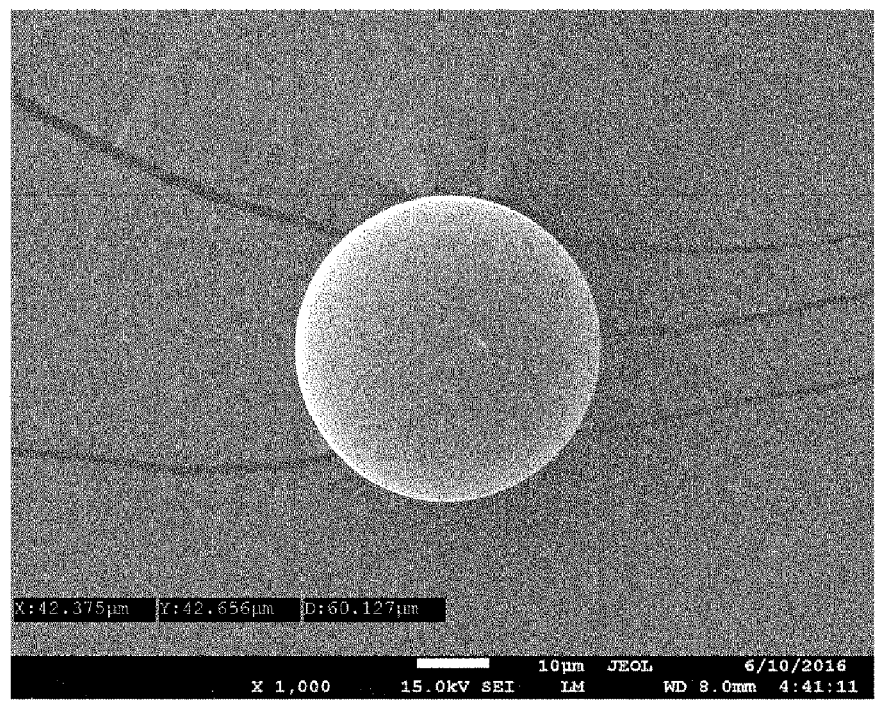
FIG. 8 is a photo of a Single Biodegradable Polymeric Microsphere obtained.
Figure 9:
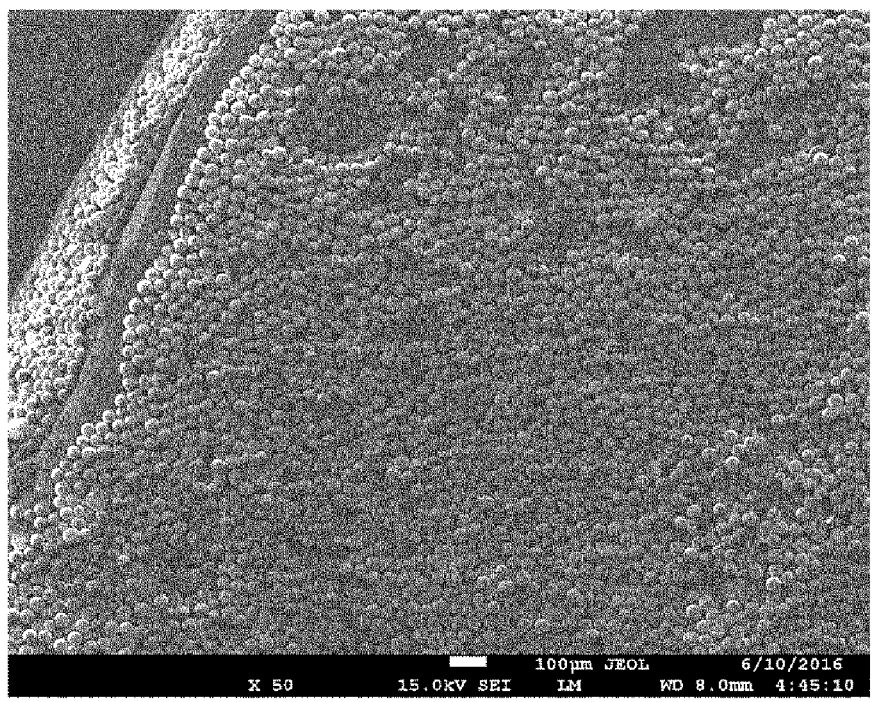
FIG. 9 is a photo of Monodisperse Biodegradable Polymeric Microspheres obtained.

Photos of the microspheres obtained based on the experiments performed for the embodiments above are shown in FIGS. 8 and 9.

Once the concentration of the surfactant and the biodegradable polymer get fixed in the respective incoming flows, i.e., within the ranges therefor specified above, the viscosity of the incoming flows will automatically get fixed and once the material for the microchip get fixed, the channel wall wettability will also get fixed, since it is usually material dependent property, leaving the flow rate of the incoming flows and the microchannel dimension as the variables/parameters to be determined/controlled.

In order to determine the effect of the microchannel dimension and the flow rate of the incoming flows on the microsphere diameter, three microchips with a microchannel having a channel dimension of 100 μm (width)×150 μm (depth), 200 μm (width)×150 μm (depth) and 300 μm (width)×150 μm (depth), respectively, were first obtained and the following sets of experiments were performed therewith, i.e., holding the flow rate of water-phase solution with a fixed surfactant concentration constant, i.e., at 0.25 weight %, while varying the flow rate of the biodegradable polymer solution with a fixed biodegradable polymer concentration constant, i.e., at 15 weight %, using each of the microchips and repeating the same procedure except for holding the flow rate of the biodegradable polymer-phase solution while varying the flow rate of the water-phase solution using each of the microchips (Please refer to Table 3) and the results of these experiments are summarized in Table 4.

TABLE 3

Experimental set-up to determine the Effect of Flow Rates and Channel Dimension on the Microsphere Diameter
Set 1: Channel Dimension: 300 μm × 150 μm
Test 1: Varying the flow rate of the water-phase solution while holding the flow rate of the biodegradable polymer-phase solution constant at 100 μl/min

|  | 1 | 2 | 3 |
|---|---|---|---|
| PCL (conc.) % | 15 | 15 | 15 |
| PVA (conc.) % | 0.25 | 0.25 | 0.25 |
| PVA (conc.) %-reservoir | 0.25 | 0.25 | 0.25 |
| PCL (flow rate)μl/min | 100 | 100 | 100 |
| PVA (flow rate)μl/min | 2000 | 3000 | 4000 |
| Organic Solvent Extraction Temperature | | | |
| temp(° C.)-17° C. | 1.5 | 1.5 | 1.5 |
| temp(° C.)-20° C. | 0.45 | 0.45 | 0.45 |
| temp(° C.)-25° C. | 0.45 | 0.45 | 0.45 |

Test 2: Varying the flow rate of the water-phase solution while holding the flow rate of the biodegradable polymer-phase solution constant at 130 μl/min

|  | 1 | 2 | 3 |
|---|---|---|---|
| PCL (conc.) % | 15 | 15 | 15 |
| PVA (conc.) % | 0.25 | 0.25 | 0.25 |
| PVA (conc.) %-reservoir | 0.25 | 0.25 | 0.25 |
| PCL (flow rate)μl/min | 130 | 130 | 130 |
| PVA (flow rate)μl/min | 2000 | 3000 | 4000 |

TABLE 3-continued

Test 3: Varying the flow rate of the water-phase
solution while holding the flow rate of the biodegradable
polymer-phase solution constant at 160 μl/min

|  | 1 | 2 | 3 |
|---|---|---|---|
| PCL (conc.) % | 15 | 15 | 15 |
| PVA (conc.) % | 0.25 | 0.25 | 0.25 |
| PVA (conc.) %-reservoir | 0.25 | 0.25 | 0.25 |
| PCL (flow rate)μl/min | 160 | 160 | 160 |
| PVA (flow rate)μl/min | 2000 | 3000 | 4000 |

Set 2: Channel Dimension: 200 μm × 150 μm
Test 1: Varying the flow rate of the water-phase
solution while holding the flow rate of the biodegradable
polymer-phase solution constant at 100 μl/min

|  | 1 | 2 | 3 |
|---|---|---|---|
| PCL (conc.) % | 15 | 15 | 15 |
| PVA (conc.) % | 0.25 | 0.25 | 0.25 |
| PVA (conc.) %-reservoir | 0.25 | 0.25 | 0.25 |
| PCL (flow rate)μl/min | 100 | 100 | 100 |
| PVA (flow rate)μl/min | 2000 | 3000 | 4000 |
| Organic Solvent Extraction Temperature |  |  |  |
| temp(° C.)-17° C. | 1.5 | 1.5 | 1.5 |
| temp(° C.)-20° C. | 0.45 | 0.45 | 0.45 |
| temp(° C.)-25° C. | 0.45 | 0.45 | 0.45 |

Test 2: Varying the flow rate of the water-phase
solution while holding the flow rate of the biodegradable
polymer-phase solution constant at 130 μl/min

|  | 1 | 2 | 3 |
|---|---|---|---|
| PCL (conc.) % | 15 | 15 | 15 |
| PVA (conc.) % | 0.25 | 0.25 | 0.25 |
| PVA (conc.) %-reservoir | 0.25 | 0.25 | 0.25 |
| PCL (flow rate)μl/min | 130 | 130 | 130 |
| PVA (flow rate)μl/min | 2000 | 3000 | 4000 |

Test 3: Varying the flow rate of the water-phase
solution while holding the flow rate of the biodegradable
polymer-phase solution constant at 160 μl/min

|  | 1 | 2 | 3 |
|---|---|---|---|
| PCL (conc.) % | 15 | 15 | 15 |
| PVA (conc.) % | 0.25 | 0.25 | 0.25 |
| PVA (conc.) %-reservoir | 0.25 | 0.25 | 0.25 |
| PCL (flow rate)μl/min | 160 | 160 | 160 |
| PVA (flow rate)μl/min | 2000 | 3000 | 4000 |

TABLE 4

Effect of Microchannel Dimension and Flow Rate of
Incoming Flows on Microsphere Diameter

| Microchannel Dimension(μm*μm) | Flow Rate of Biodegradable Polymer-phase Solution: 15 wt % PCL (μl/min) | Flow Rate of Water-phase Solution: 0.25 wt % PVA(μl/min) | Microsphere Diameter(μm) |
|---|---|---|---|
| 200*150 | 100 | 2000 | 146.7 |
| 200*150 | 100 | 3000 | 125.2 |
| 200*150 | 100 | 4000 | 97.67 |
| 200*150 | 130 | 2000 | 128 |
| 200*150 | 130 | 3000 | 60.87 |
| 200*150 | 130 | 4000 | 67.09 |
| 200*150 | 160 | 2000 | 164.4 |
| 200*150 | 160 | 3000 | 160.2 |
| 200*150 | 160 | 4000 | 66.04 |
| 300*150 | 100 | 2000 | 213.9 |
| 300*150 | 100 | 3000 | 145.1 |
| 300*150 | 100 | 4000 | 173.4 |
| 300*150 | 130 | 2000 | 230.6 |
| 300*150 | 130 | 3000 | 134.9 |
| 300*150 | 130 | 4000 | 167.8 |
| 300*150 | 160 | 2000 | 268.1 |
| 300*150 | 160 | 3000 | 234.1 |
| 300*150 | 160 | 4000 | 228 |

Effects of the Microchannel Dimension and Flow Rate of the Incoming Flows on the Microsphere Diameter Based on the experimental results shown in Table 4, effects of the microchannel dimension and the flow rate of the incoming flows on the diameter of the microspheres formed, the microchannel dimension has more immediate/direct/controllable effects on the diameter/size of the microspheres formed than the flow rate of the incoming flows, and the effects of each factors, i.e., the dimension and the flow rate of the incoming flows, will be described in detail hereinbelow.

Figure 10:
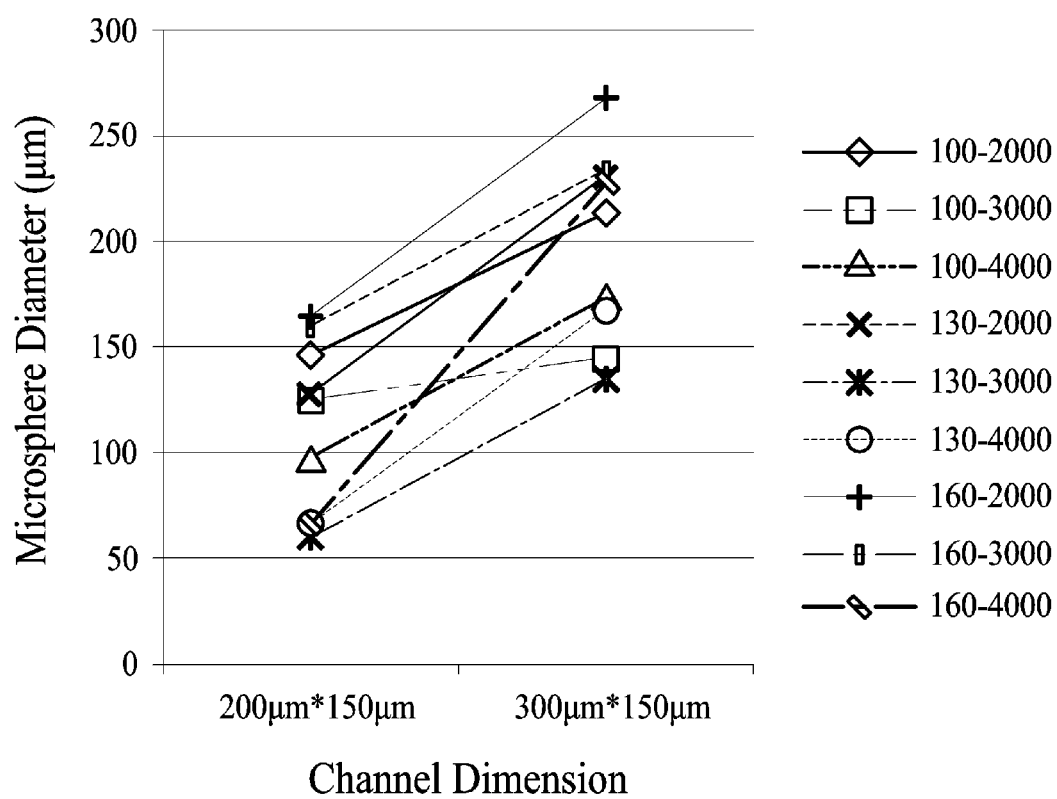
FIG. 10 illustrates the effect of Microchannel Channel Dimension on the Microsphere Diameter, with the Flow Rate of the Incoming Flows held constant.
Figure 11:
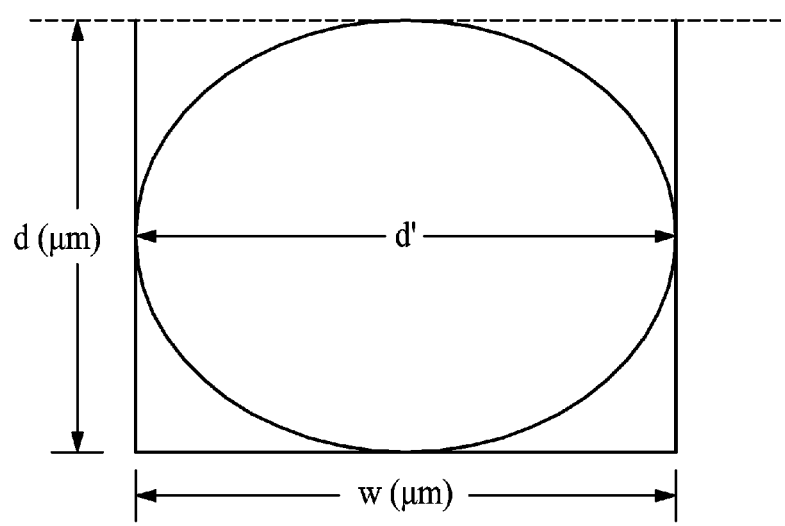
FIG. 11 is a cross-sectional view of the Microchannel and the Microsphere formed therein.
Figure 12A:
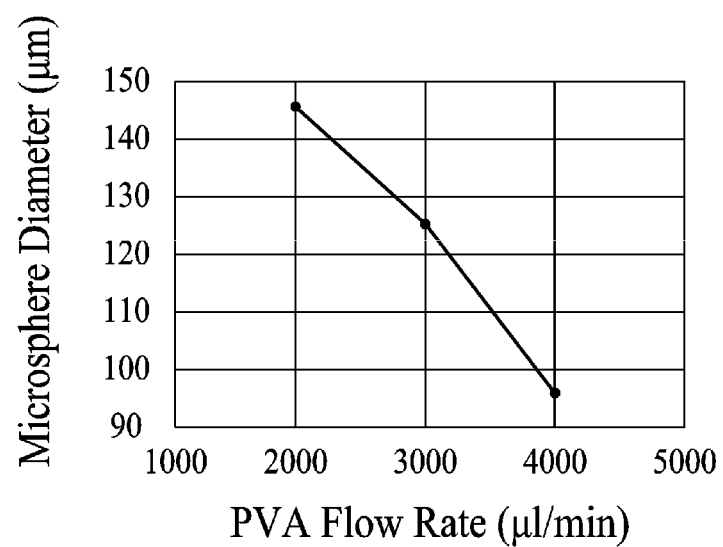
FIG. 12A illustrates the effect of the Flow Rate of the Water-Phase Solution on the Microsphere Diameter (Flow Rate of the Biodegradable Polymer-phase Solution and the Dimension of the Microchannel Constant at 100 μl/min and 200 μm*150 μm, respectively, while varying that of the Water-phase Solution).
Figure 12B:
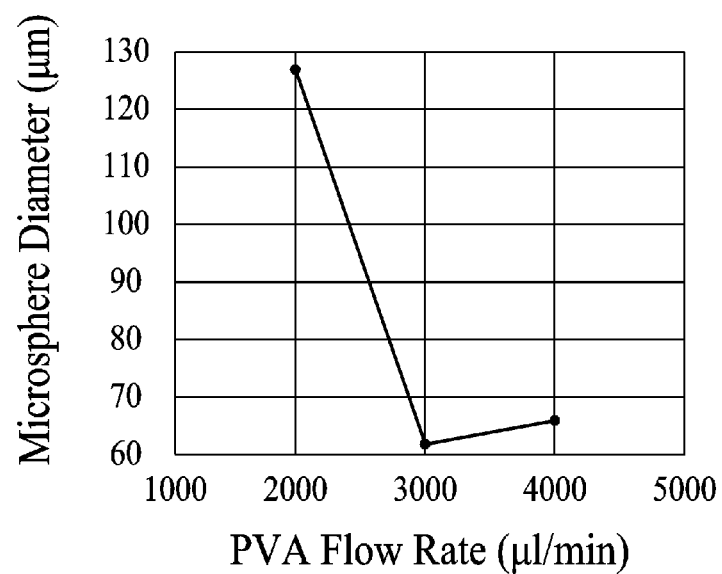
FIG. 12B illustrates the effect of the Flow Rate of the Water-Phase Solution on the Microsphere Diameter (Flow Rate of the Biodegradable Polymer-phase Solution and the Dimension of the Microchannel Constant at 100 μl/min and 200 μm*150 μm, respectively, while varying that of the Water-phase Solution).
Figure 12C:
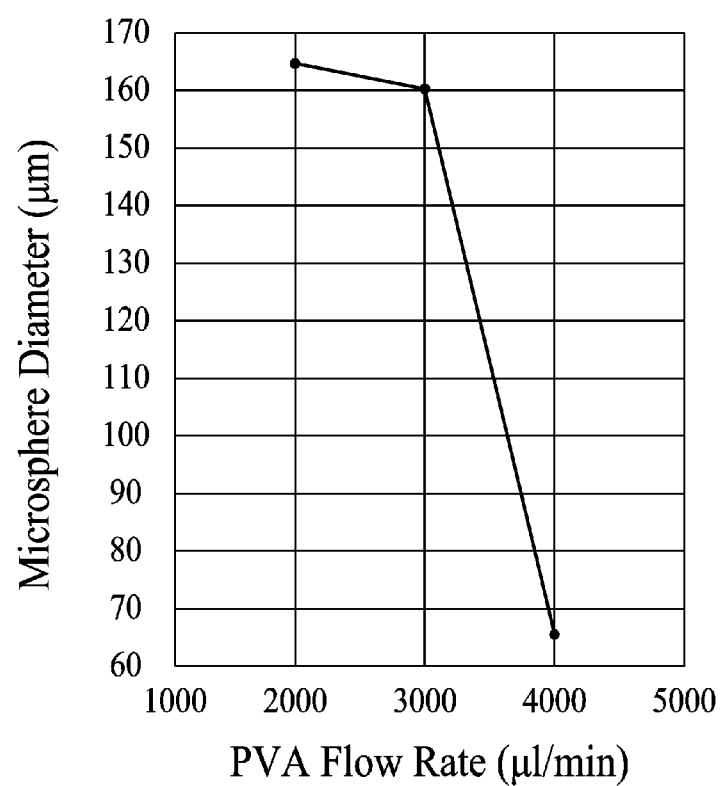
FIG. 12C illustrates the effect of the Flow Rate of the Water-Phase Solution on the Microsphere Diameter (Flow Rate of the Biodegradable Polymer-phase Solution and the Dimension of the Microchannel Constant at 100 μl/min and 200 μm*150 μm, respectively, while varying that of the Water-phase Solution).
Figure 12D:
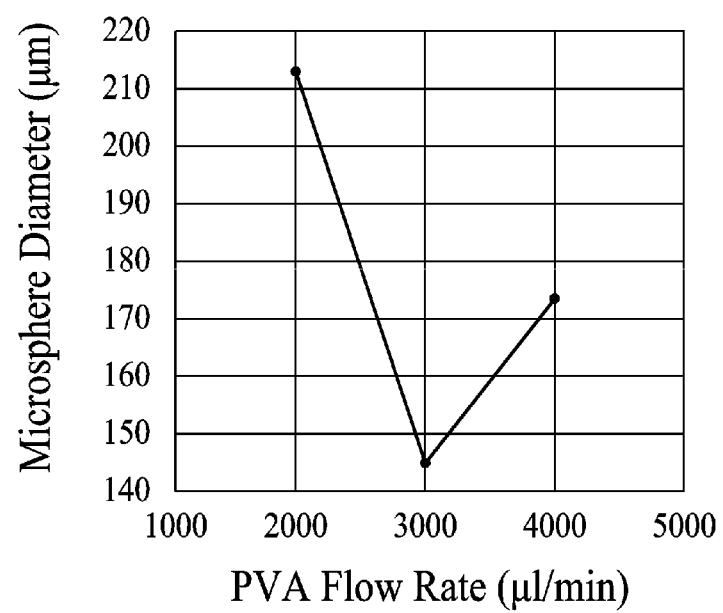
FIG. 12D illustrates the effect of the Flow Rate of the Water-Phase Solution on the Microsphere Diameter (Flow Rate of the Biodegradable Polymer-phase Solution and the Dimension of the Microchannel Constant at 100 μl/min and 200 μm*150 μm, respectively, while varying that of the Water-phase Solution).
Figure 12E:
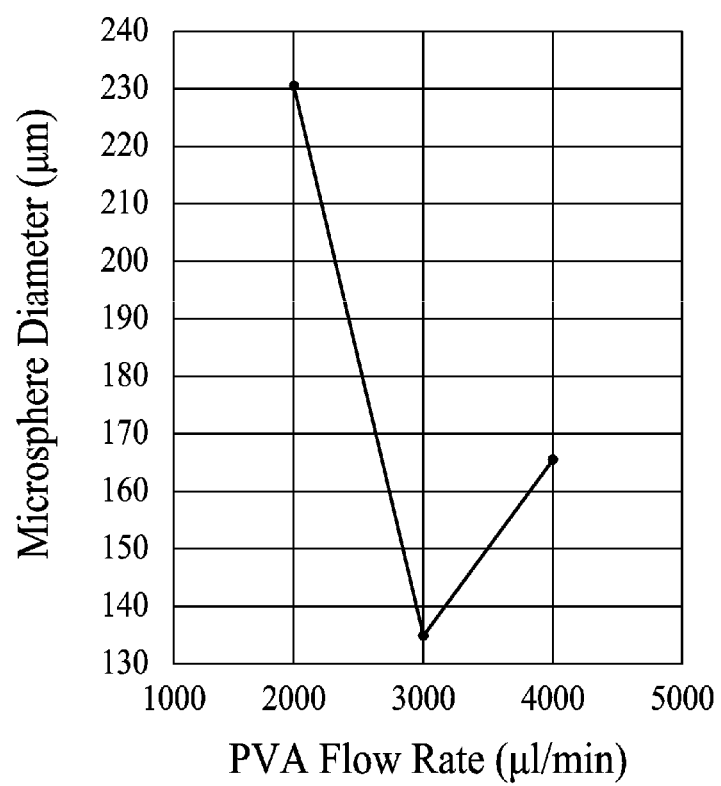
FIG. 12E illustrates the effect of the Flow Rate of the Water-Phase Solution on the Microsphere Diameter (Flow Rate of the Biodegradable Polymer-phase Solution and the Dimension of the Microchannel Constant at 100 μl/min and 200 μm*150 μm, respectively, while varying that of the Water-phase Solution).
Figure 12F:
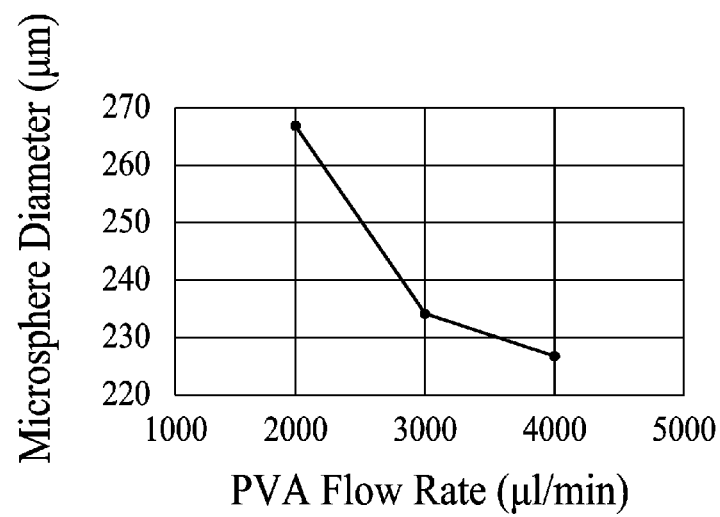
FIG. 12F illustrates the effect of the Flow Rate of the Water-Phase Solution on the Microsphere Diameter (Flow Rate of the Biodegradable Polymer-phase Solution and the Dimension of the Microchannel Constant at 100 μl/min and 200 μm*150 μm, respectively, while varying that of the Water-phase Solution).

Effect of the Microchannel Dimension on the Diameter of the Microspheres Determined while Holding the Flow Rate of the Incoming Flows Constant As shown in FIG. 10, there is a strong correlation, i.e., usually a linear relationship or close thereto, between the channel dimension of the microchannel and the microsphere diameter, d': An increase in channel dimension results in a corresponding increase in microsphere diameter, d'. Ideally speaking, the cross-section of the microchannel should be a circle, i.e., similar to the cross-section of the microsphere to be formed, which is an extremely difficult task, and accordingly, the next best solution thereto would be formation of microchannels having a cross-section thereof being a square, as shown in FIG. 11, i.e., the depth (d) and the width (w) of the cross-section of the microchannels being identical. It has been experimentally determined that in order to expedite an efficient formation of monodisperse microspheres, the dimension of the microchannel, i.e., the width (w) and the depth (d), as shown in FIG. 11, should be within 30% of the desired diameter, d'. That is, if the desired microsphere diameter is 100 μm, the width (w) or the depth (d) of the microchannel should preferably be within 70 μm and 130 μm or a combination thereof. Another way of saying what has been stated above is that the cross-sectional area of the microchannels, i.e., depth (d)×width (w), should be within 30% of the cross-sectional area of the microsphere desired, i.e., (0.5 d')×(0.5 d')π. Should this task of forming microchannels whose cross-section is a square is difficult, it has been experimentally further determined that at least either one of the depth (d) or the width (w) of the cross section of the microchannels should be within 30% of the desired diameter of the microspheres to be formed.

Effect of the Flow Rate of Incoming Flows on the Microsphere Diameter

According to the results obtained, of the two flow rates, i.e., the flow rate of the water-phase solution including therein the surfactant and that of the biodegradable polymer-phase solution including therein the biodegradable polymer, the flow rate of the water-phase solution is more critical than that of the biodegradable polymer-phase solution, although not as critical as that of the microchannel dimension, as can be seen in FIG. 10, in affecting the diameter of the microspheres being formed, for the flow of the water-phase solution, and hence the rate thereof, is the flow providing the force for segmenting the biodegradable polymer-phase solution to the desired size of microspheres, i.e., the microspheres having the desired diameter, and the effects of the flow rate of the water-phase solution are shown in Table 5 and FIGS. 12A through 12F. As can be seen from Table 5 and FIGS. 12A through 12F, the diameter of the microspheres is generally inversely linearly proportional to the flow rate of the water-phase solution, i.e., an increase in the flow rate results in a corresponding decrease in the diameter of the microspheres, and this relationship only is applicable only in a certain range of the flow rate, for if the flow rate of the water-phase solutions is too low, it results in the formation of biodegradable polymer-based microspheres having a wide microsphere diameter distribution and if the flow rate is more too high, it results in the formation of microspheres having diameters of less than 10 µm diameter, possibly resulting in the biodegradable polymer-based microspheres being easily absorbed by the body or the biodegradable polymer-based microspheres having a too short of biodegradation time when injected into the body. At the crossing point, the relatively slower moving biodegradable polymer-phase solution gets pressed by the relatively faster moving water-phase solution, resulting disrupting the flow of the biodegradable polymer-phase solution, isolating a small amount of the biodegradable polymer-phase solution to be surrounded by the water-phase solution, leading to the formation of microspherical droplets due to the surface tension. For the current system involving a microchannel made up of silicon wafer, a water-phase solution including therein PVA as the surfactant and a biodegradable polymer-phase solution including therein PCL as the biodegradable polymer, the range of the flow rate of the water-phase solution that be incorporated is between 500 µl/min and 5000 µl/min.

TABLE 5

Effect of the Flow Rate of the Water-phase Solution on the Diameter of the Microspheres (a)

| | PCL (µl/min) | PVA (µl/min) | Microsphere Diameter (µm) |
|---|---|---|---|
| 200 (µm) X 150 (µm) | 100 | 2000 | 146.7 |
| | 100 | 3000 | 125.2 |
| | 100 | 4000 | 97.7 |

(b)

| | PCL (µl/min) | PVA (µl/min) | Microsphere Diameter (µm) |
|---|---|---|---|
| 200 (µm) X 150 (µm) | 130 | 2000 | 128 |
| | 130 | 3000 | 60.8 |
| | 130 | 4000 | 67.1 |

TABLE 5-continued

Effect of the Flow Rate of the Water-phase Solution on the Diameter of the Microspheres (c)

| | PCL (µl/min) | PVA (µl/min) | Microsphere Diameter (µm) |
|---|---|---|---|
| 200 (µm) X 150 (µm) | 160 | 2000 | 164.4 |
| | 160 | 3000 | 160.2 |
| | 160 | 4000 | 66.0 |

(d)

| | PCL (µl/min) | PVA (µl/min) | Microsphere Diameter (µm) |
|---|---|---|---|
| 300 (µm) X 150 (µm) | 100 | 2000 | 213.9 |
| | 100 | 3000 | 145.1 |
| | 100 | 4000 | 173.4 |

(e)

| | PCL (µl/min) | PVA (µl/min) | Microsphere Diameter (µm) |
|---|---|---|---|
| 300 (µm) X 150 (µm) | 130 | 2000 | 230.6 |
| | 130 | 3000 | 134.9 |
| | 130 | 4000 | 167.8 |

(f)

| | PCL (µl/min) | PVA (µl/min) | Microsphere Diameter (µm) |
|---|---|---|---|
| 300 (µm) X 150 (µm) | 160 | 2000 | 268.1 |
| | 160 | 3000 | 234.1 |
| | 160 | 4000 | 228.0 |

Effect of the Flow Rate of the Biodegradable Polymer-Phase Solution on the Microsphere Diameter In another embodiment of the present invention, the flow rate of the biodegradable polymer-phase solution ranges between 10 µl/min and 500 µl/min, and preferably between 50 µl/min and 200 µl/min. If the biodegradable polymer-phase solution flows at a rate lower 50 µl/min, it leads to microspheres becoming smaller, resulting in shortening of the biodegradation time and having a wide particle-size distribution. Meanwhile, if the biodegradable polymer-phase solution flow at a rate higher than 200 µl/min, it leads to microspheres becoming larger, making it difficult to inject and having a wide particle-size distribution. There is shown in Table 6 and FIG. 13 the effects of the flow rate of the biodegradable polymer-phase solution on the diameter of the microspheres formed.

Figure 13:
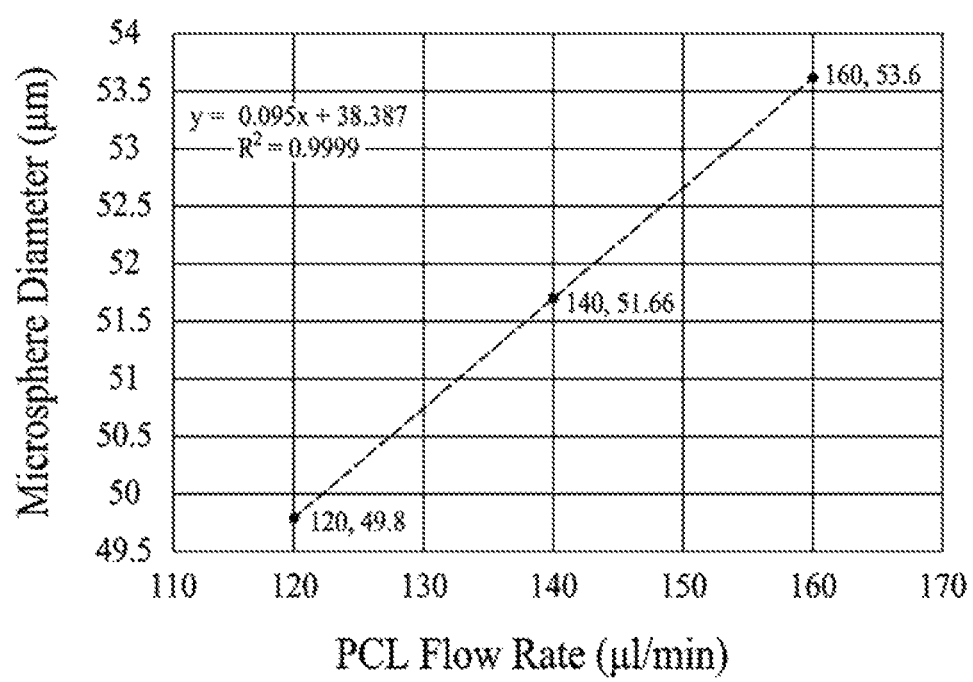
FIG. 13 illustrates the effect of the Flow Rate (μm/min) of the Biodegradable Polymer-phase Solution on the Microsphere Diameter (μm).

According to the results shown in Table 6 and FIG. 13, there is a strong linear relationship between the flow rate and the diameter, as defined by the following relationship:

Microsphere Diameter=0.095*(Flow Rate)+38.387
with a standard deviation of 0.9999.

TABLE 6

Effect of the Flow Rate (μl/min) of the
Biodegradable Polymer Solution on
the Microsphere Diameter (μm)

| PCL Flow Rate (μl/min) | Microsphere Diameter (μm) |
|---|---|
| 120 | 49.8 |
| 140 | 51.7 |
| 160 | 53.6 |

Although there is a linear relationship between the flow rate of the biodegradable polymer-phase solution and the diameter of the microspheres formed, the effect thereof on the diameter is not as critical as those of the channel dimension and the flow rate of the water-phase solution, i.e., very minor effect on the diameter, and hence it should be used as a "controlling parameter for fine-tuning" the diameter of the final microspheres formed, i.e., after using the channel dimension and the flow rate of the water-phase solution to initially fix the diameter of the microspheres obtained.

It has been experimentally determined that the ratio of the flow rate of the biodegradable polymer-phase solution to the flow rate of the water-phase solution ranges between 1:2 to 1 to 100, preferably between 1:2 to 1:50.

Hereinafter, the present invention will be described in further detail through the following example, using a microchip incorporating therein the simplest form of microchannles, i.e., lab-scale, shown in FIGS. 3, 4 and 5 and the principles developed hereinabove. The example is only for illustrating the invention more specifically, and it is obvious to the persons in the industry with common knowledge that the scope of the invention is not limited to the examples according to the content of the invention.

Firstly, 10 mL of the biodegradable polymer-phase solution was obtained by dissolving polycaprolactone (PCL) with Mn~45,000 or less, wherein Mn is the number average molecular weight obtained by dividing the molecular weight of the molecular species comprising polymeric compounds with molecular weight distribution by the number or mole fraction, in a solvent, e.g., dichloromethane (solvent, melting point: 39.6° C.) at a concentration of 15 weight %. Secondly, 250 mL of the water-phase solution is prepared by dissolving a surfactant, i.e., polyvinyl alcohol (PVA) having a molecular weight of 85000 to 124000, in purified water at a concentration of 0.25 weight %. Thirdly, 100 mL of the receiver solution is prepared by dissolving polyvinyl alcohol in purified water at a concentration of 0.25 weight percent. The above biodegradable polymer-phase solution is injected into one of the microchannels, i.e., Channel 2, at a fixed flow rate, e.g., 100 μl/min' as Flow 2 and the prepared water-phase solution at 90° angle from the flow of the biodegradable polymer solution through Channel 1 and Channel 3, as Flow 1 and Flow 3 at a fixed rate, e.g., 1000 μl/min.

Dispersed phase is generated at the merging point 15 of the biodegradable polymer-phase solution and the water phase solution. Thereafter, the dispersed phase, including therein the microspheric droplets formed at the merging point 15, flows out through the outlet 14 to be collected in the receiver solution, and dichloromethane solvent is extracted therefrom by keeping the receiver solution included therein the dispersed phase at room temperature (25° C.) for about 24 hours, resulting a water-phase solution containing biodegradable polymer-based microspherical droplets. Microspherical droplets are separated out from the water phase solution through a filtering process. Microspheres containing biodegradable polymers are finally obtained by washing the microsphere droplets to remove the remaining polyvinyl alcohol and dichloromethane solution, followed by a drying process (Please refer to FIG. 2).

To be more specific, the method described above is largely composed of four flows, i.e., Flow 1, Flow 2, Flow 3 and Flow 4: Flow 2 established by the flow of biodegradable polymer-phase solution prepared by dissolving biodegradable polymer in an organic solvent; Flow 1 and Flow 3, established by the flow of the water-phase solutions prepared by dissolving the surfactant in purified water; and Flow 4, established by the flow resulting from Flows 1, 2 and 3 meeting at the merging point 15. Flow 2 runs in the same direction as Flow 4, and Flow 1 and Flow 3 run toward each other and merge together at the crossing point 15 (Please refer to FIG. 5). The flow rate of Flow 1, Flow 2 and Flow 3 and the angle at which Flow 1 and Flow 3 merge with Flow 2 affect the size of microspheres generated, the particle size distribution and the production yield.

In the present invention, those biodegradable polymer-based microspherical droplets formed at the merging point 15 are collected in a receiver containing a receiver solution including therein a surfactant, and the reason for using the receiver solution including therein the surfactant is to prevent those biodegradable polymer-based microspherical droplets from coagulating.

Those biodegradable polymer-based microspherical droplets collected in the step described above undergo a first drying at a temperature between 0° C. and 50° C., and preferably between, 20° C. and 25° C. When an emulsion in form of a droplet is kept at under the boiling point of the organic solvent for a certain amount of time, for example, between 12 and 48 hours, the organic solvent therein gets extracted from the droplet, resulting in the formation of a microsphere though solidification process.

The biodegradable polymer-based microspheres formed in the step described above are filtered and are then washed with purified water at least once, preferably between one and three times to remove the remaining surfactant and solvent, followed by one more filtering process. The washing process may be repeated until the remaining surfactant and the solvent are completely removed.

In an embodiment herein, the step described above is followed by another drying process and the drying method to be used is not particularly limited. Although, however, the drying method to be used is not particularly limited, it is preferred that the microspheres should be dried in vacuum or using lyophilization to minimize heat damages to the biodegradable polymer included in the microspheres.

The average diameter of the biodegradable polymer-based microspheres produced using the apparatus and method prescribed hereinabove ranges between 10 μm and 200 μm, preferably between 30 μm and 150 μm. If the average diameter of the microspheres is less than 10 μm, the microspheres may easily end getting absorbed in the body when injected or the biodegradation time thereof may end of being too short to fulfill their intended purpose. On the other hand, if the average diameter of the microspheres exceeds 150 μm, it may result in creating difficulties in interdermal injection thereof.

When microspheres are prepared using a conventional batch process, for example, solvent extraction-evaporation process, it may lead to the formation of microspheres having irregular particle sizes and a relatively wider particle-size distribution. In such a case, the microspheres of an undesired size is separated out through, for example, filtering or sieving, to obtain the monodispersity of the microspheres, which will, in turn, end up detrimentally affecting the final yield of the process, in addition to unnecessarily complicating the manufacturing process. However, using the apparatus and the method based on immiscibility of the solutions used and basic underlying principles behind HCMMM, described herein above, it is possible to manufacture monodisperse biodegradable polymer-based microspheres, with a higher yield and enhanced simplicity and controllability.

Biodegradable polymer-based microspheres prepared in accordance with the apparatus and the method of the present invention is not limited to a particular usage. For example, they may be used in skin aesthetics or as a medical filler requiring bioresorption, particularly as injectable subcutaneous or intradermal fillers that can be implanted into the body, but not limited only thereto.

Although the reabsorbability time of biodegradable polymers-based microspheres prepared in accordance with the apparatus and the method of the present invention is not particularly limited, it should preferably be between one and three years, considering that they are used as biodegradable fillers for skin aesthetics or medical purposes.

SUMMARY OF THE EXPERIMENTAL RESULTS

To summarize there are five important parameters to be controlled to optimize the mass production of monodisperse microspheres, namely, the flow rate of the incoming flows, the viscosity of the incoming flow, the surfactant concentration in the water-phase solution, the biodegradable polymer concentration in the biodegradable polymer-phase solution, the channel wall wettability and the channel dimensions, and of the critical/important parameters mentioned, it is possible to fix the channel wall wettability by setting the material to be used for the microchip, and the viscosity, by fixing the fluids and the concentration of the biodegradable polymer and the surfactant being incorporate therein, respectively, the optimal concentration thereof being easily determined through experiments, leaving the flow rate of the incoming flows, i.e., incoming flow including therein the biodegradable polymer and incoming flow(s) including therein the surfactant, the channel dimension and the concentration of the surfactant and the biodegradable polymer in the respective incoming flows as the key variables to be controlled.

It has been experimentally determined that it the concentration of the surfactant is equal to or greater than 0.15 weight %, the effect thereof on the microsphere diameter becomes negligible up to 0.25 weight %, flattening out at around 0.30 weight %.

As for the effect of the concentration of the biodegradable polymer, if the concentration of the biodegradable polymer is less than 5 weight %, it results in microspheres not being formed. If the concentration exceeds 30 weight %, it results in microspheres formed having non-spherical shape, and for those concentrations between 5% and 30%, there is a strong correlation, i.e., for example, roughly a linear relationship, existing between the concentration of the biodegradable polymer in the biodegradable polymer-phase solution and the microsphere diameter, as defined by the following relationship:

Microsphere Diameter=−0.408*(Biodegradable Polymer Concentration)+57.1 with a standard deviation of 0.8048.

Based on the experimental results, the biodegradable polymer concentration is between 5 weight % and 30 weight %, and the relationship developed can be used to fine tune the microsphere diameter, if not for all biodegradable polymers, at least for the PCL based system.

Of the remaining variables, i.e., the channel dimension and the flow rate of the incoming flows, it has been determined that the microchannel dimension has the most immediate/direct/controllable effects on the diameter/size of the microspheres formed than the flow rate of the incoming flows. It has been experimentally determined that there is a strong correlation, i.e., usually a linear relationship or close thereto, between the channel dimension of the microchannel and the microsphere diameter: An increase in channel dimension results in a corresponding increase in microsphere diameter. Ideally speaking, the cross-section of the microchannel should be a circle, i.e., similar to the cross-section of the microsphere to be formed, which is an extremely difficult task, and accordingly, the next best solution thereto would be formation of microchannels having a cross-section thereof being a square, i.e., the depth (d) and the width (w) of the cross-section of the microchannels being identical. It has been experimentally determined that in order to expedite an efficient formation of monodisperse microspheres, the dimension of the microchannel, i.e., the width (w) and the depth (d), should be within 30% of the desired diameter of the microspheres to be produced, i.e., the cross-sectional area of the microchannels, should be within 30% of the cross-sectional area of the microspheres desired. Should this task of forming microchannels whose cross-section is a square is found to be difficult, it has been experimentally further determined that at least either one of the depth (d) or the width (w) of the cross section of the microchannels should be within 30% of the desired diameter of the microspheres to be formed.

According to the results obtained, of the two flow rates, i.e., the flow rate of the water-phase solution including therein the surfactant and that of the biodegradable polymer-phase solution including therein the biodegradable polymer, the flow rate of the water-phase solution is more critical than that of the biodegradable polymer-phase solution in affecting the diameter of the microspheres being formed, for the flow of the water-phase solution, and hence the rate thereof, is the flow providing the force for segmenting the biodegradable polymer-phase solution to the desired size of microspheres, i.e., the microspheres having the desired diameter, for the diameter of the microspheres is generally inversely linearly proportional to the flow rate of the water-phase solution, i.e., an increase in the flow rate results in a corresponding decrease in the diameter of the microspheres, and this relationship only is applicable only in a certain range of the flow rate.

Although not as critical as the flow rate of the water-phase solution in affecting the microsphere diameter, there is a strong correlation between the flow rate of the biodegradable polymer-phase solution and the microsphere diameter, i.e., usually a linear relationship, in a specific range of flow rates and hence, can be used as a controlling parameter for fine-tuning the diameter of the microspheres to be formed after using the channel dimension and the flow rate of the water-phase solution to initially fix the diameter of the microspheres obtained.

It has been experimentally determined that the ratio of the flow rate of the biodegradable polymer-phase solution to the flow rate of the water-phase solution ranges between 1:2 to 1 to 100, preferably between 1:2 to 1:50.

Further, to obtain microspherical droplets with a narrow size distribution, i.e., monodisperse microspherical droplets, the angle at which the flows of the water-phase solution merge with the flow of the biodegradable polymer-phase solution should be set between 30° and 90°.

Mass Production

Figure 14:
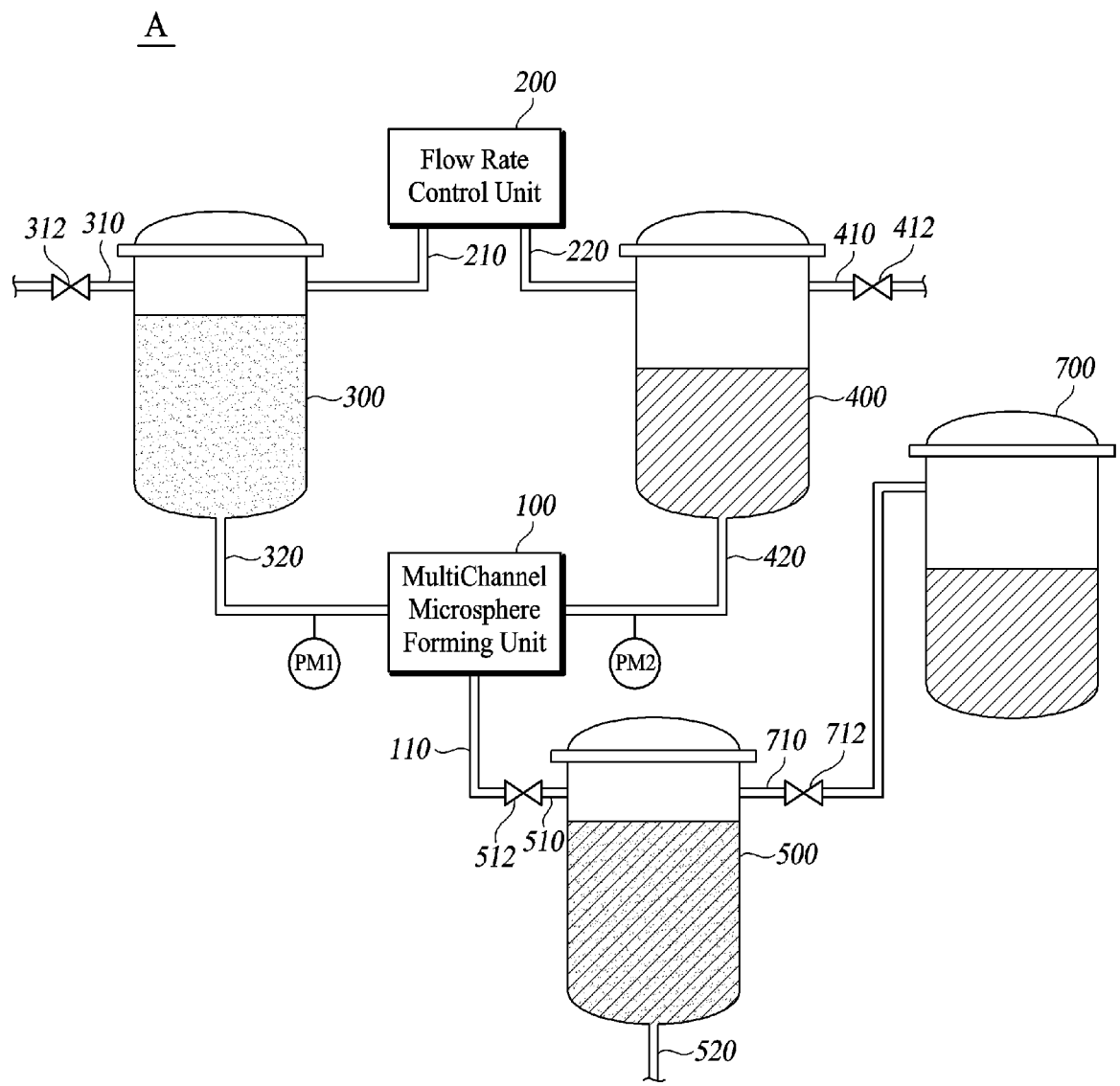
FIG. 14 is a block diagram of the Mass Production Apparatus for Microspheres according to an embodiment of the present Invention.
Figure 15A:
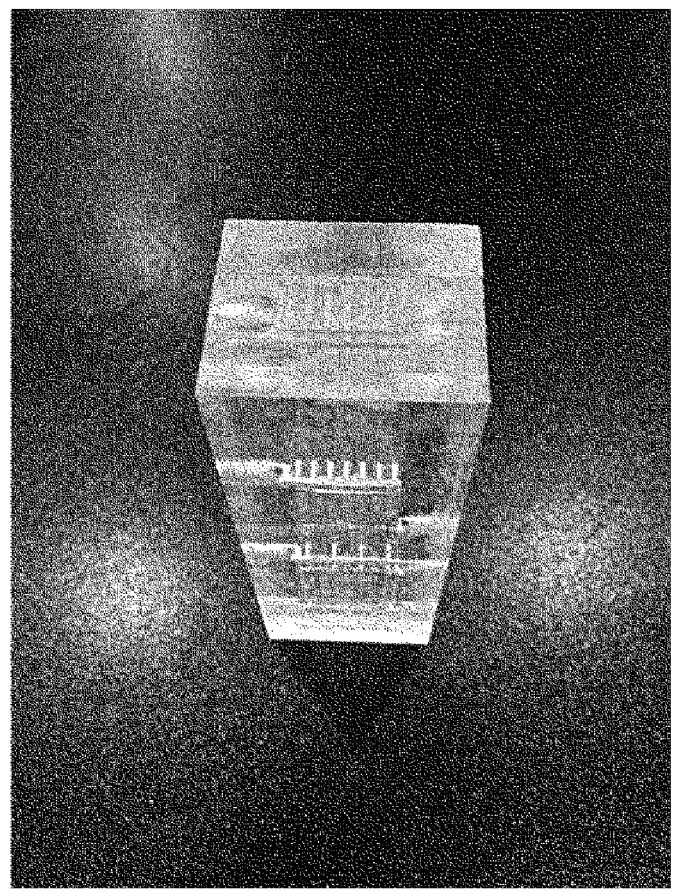
FIG. 15A is a photo of a Prototype Microchip Developed for Mass Production of Microspheres (Top View).
Figure 15B:
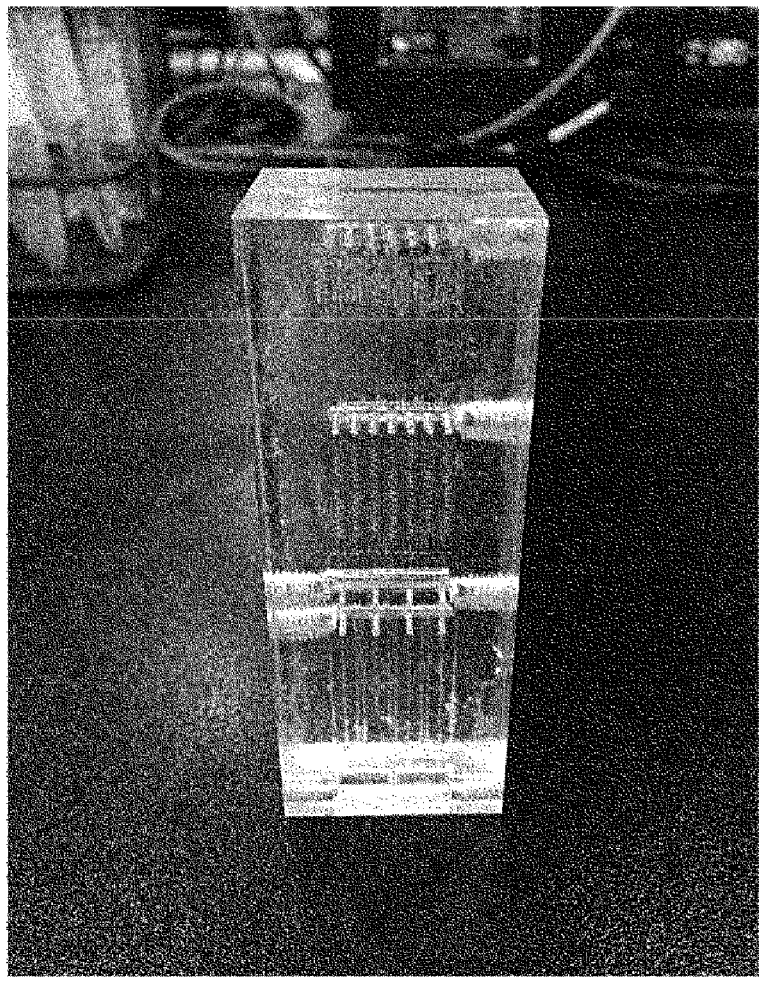
FIG. 15B is a photo of a Prototype Microchip Developed for the Mass Production of Microspheres (Side View).
Figure 15C:
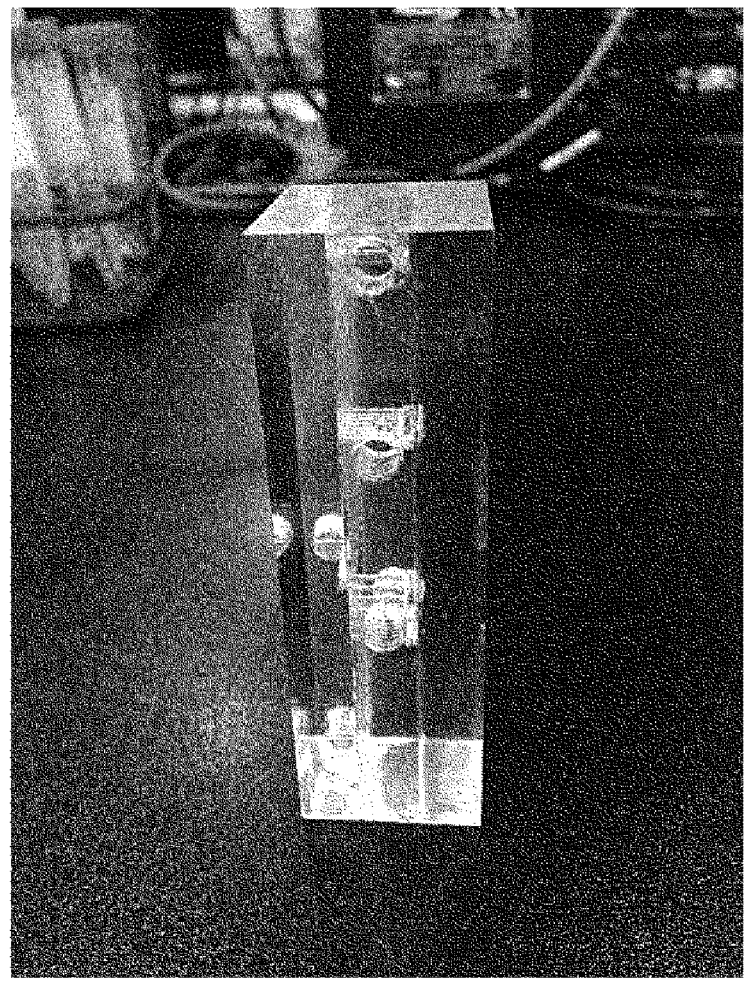
FIG. 15C is a photo of a Prototype Microchip Developed for the Mass Production of Microspheres (Side View).

An optimized apparatus and process for a mass production of monodisperse microsperes has been realized based on the results obtained and described hereinabove. There are illustrated in FIG. 14 and FIGS. 15 A to C the lay-out of the apparatus for mass production and the photos of a prototype microchip to be incorporated into Multi-Channel Microsphere Forming Unit 100 in FIG. 14. Theoretically, the easiest way to develop an apparatus for mass production of microspheres is to develop microchips incorporating therein a plurality of single microsphere production units shown in FIG. 5 in parrallel and, in turn, arrange those microchips in parrallel. As an example of such a microchip, there are shown in FIGS. 15A through 15C photos of a prototype microchip developed for the mass production of microspheres incorporating therein seven such microsphere production units shown in FIG. 5 in a single microchip. To achieve a mass production of microspheres using the microchips shown in FIGS. 15A to C, they are arranged in parrallel, the total number of microchips needed depending on the mass production requirement.

In the microchip shown in FIGS. 15A to C, a plurality of microsphere production units are formed on hydrophobic polymer wafer, such as PDMS, for the advantages of using these particular polymer surfaces are several. They are completely bio-inert and antifouling, making them ideally suited to biopharmaceutical processing and manufacturing. The wafer chips themselves are relatively inexpensive and completely disposable. What is most important, the polymers enable establishment of segmented flow conditions with a high level of stability and reliability, making the mass production of biodegradable polymer-based microspheres possible.

However, the use of such a large number of microsphere productions units in the Multichannel Microsphere forming Unit, and hence the corresponding number of microchannels associated therewith, necessitate a need for the supply of corresponding controlled amount of fluid flowing thereinto and this is an extremely difficult task using conventional lab-scale fluid supply units, e.g., a fluid pump, for the conventional lab-scale fluid supply units, in general, have a pressure fluctuation corresponding to the operating cycle thereof. Accordingly, a solution is found capable of providing a constant flow condition within each microchannel with a constant pressure therewithin, i.e., consistency in the flow rate between the microchannels.

In addition, an increased number of microchannels in the microchip, i.e., an increased in microchannel density within the microchip, results in the microchannel structure therein becoming very complicated/complex, resulting in flow paths therein becoming inconsistent, which, in turn, causing the flow resistance within each microchannel becoming inconsistent with respect to one another, and if the flow resistances are different for each microchannel, the flow within each microchannel will end up being different. Accordingly, in order for the microchip described hereinabove to be used in mass production of microspheres, a means capable of providing a consistent flow condition, and hence, an even flow rate, in each of the microchannels are determined, prior to the microchip being used in mass production of microspheres.

In order to solve the above-mentioned problems, new concepts capable of providing and maintaining a constant and equal flow within each of the microchannels have been proposed and developed. This concept may be implemented as an exemplary embodiment, and some of the exemplary embodiments thereof are described below.

Referring to FIG. 14, the mass producing apparatus for microspheres according to an embodiment of the present invention comprises a first material reservoir 300, a second material reservoir 400, a flow rate control unit 200, a multichannel microsphere forming unit 100, a product reservoir 500 and a dispersion reservoir 700.

The first material reservoir 300 comprises a first raw material in the form of a water-phase solution comprising pure water dissolved therein a surfactant, for example, 0.25% by weight of polyvinyl alcohol (PVA) having a molecular weight of 8500 to 124000 as the surfactant dissolved in pure water.

The first raw material is sterilized through a sterilization process, for example, by being passed through a sterilization filtration filter. The filtered first raw material is then introduced into the first material reservoir 300 through a first material inlet 310. After the sterilized first raw material is sufficiently or completely introduced into the first material reservoir 300, the first material inlet valve 312 mounted in the first material inlet 310 is shut off, thereby isolating the first material reservoir 300 from the outside and the sterilization state to be maintained therewithin.

The second material reservoir 400 comprises a second raw material that is an oil-phase solution comprising an organic solvent and a biodegradable polymer dissolved therein. For example, the organic solvent of the second raw material may be dichloromethane (solvent, melting point 39.6° C.), and the biodegradable polymer may be polycaprolactone (PCL) with Mn of about 45,000 or less in dichloromethane at a concentration of 15 wt %, wherein Mn is the number average molecular weight obtained by dividing the molecular weight of the molecular species comprising polymeric compounds with molecular weight distribution by the number or mole fraction.

The second raw material is sterilized through a sterilization process, for example, by being passed through a sterilization filtration filter. The sterilized second raw material is introduced into the second material reservoir 400 through a second material inlet 410. After the sterilized second raw material is sufficiently or completely introduced into the second material reservoir 400, the second material inlet valve 412 installed in the second material inlet 410 is shut off, thereby isolating the second material reservoir 400 from the outside and the sterilization state to be maintained therewithin.

The first raw material stored in the first material reservoir 300 and the second raw material stored in the second material reservoir 400 are then transferred to the multichannel microsphere forming unit 100 through the first material outlet 320 and the second raw material outlet 420, respectively.

The flow rate control unit 200 is in fluid communication with the first material reservoir 300 through the first flow control line 210 and in fluid communication with the second material reservoir 400 through the second flow control line 220, respectively, the flow control unit 200 introducing a first gas having a first raw material flow rate into the first material reservoir 300 and a second gas having a second raw material flow rate into the second material reservoir 400. The first gas and the second gas may be of substantially the same kind of gas, for example, clean air or an inert gas.

The first raw material stored in the first material reservoir 300 is delivered to the multichannel microsphere forming unit 100 in an amount corresponding to the first raw material flow rate of the introduced first gas. Similarly, the second raw material stored in the second material reservoir 400 may be delivered to the multichannel microsphere forming unit 100 in an amount corresponding to the second raw material flow rate.

FIG. 14 is Block Diagram of a Mass Production Apparatus for Microspheres according to an Embodiment of the Present Invention. FIG. 15 A is Photo of a Prototype Microchip Developed for Mass Production of Microspheres (Top View). FIG. 15B is Photo of a Prototype Microchip Developed for Mass Production of Microspheres (Side View). FIG. 15C is Photo of a Prototype Microchip Developed for Mass Production of Microspheres (Side View).

Figure 16:
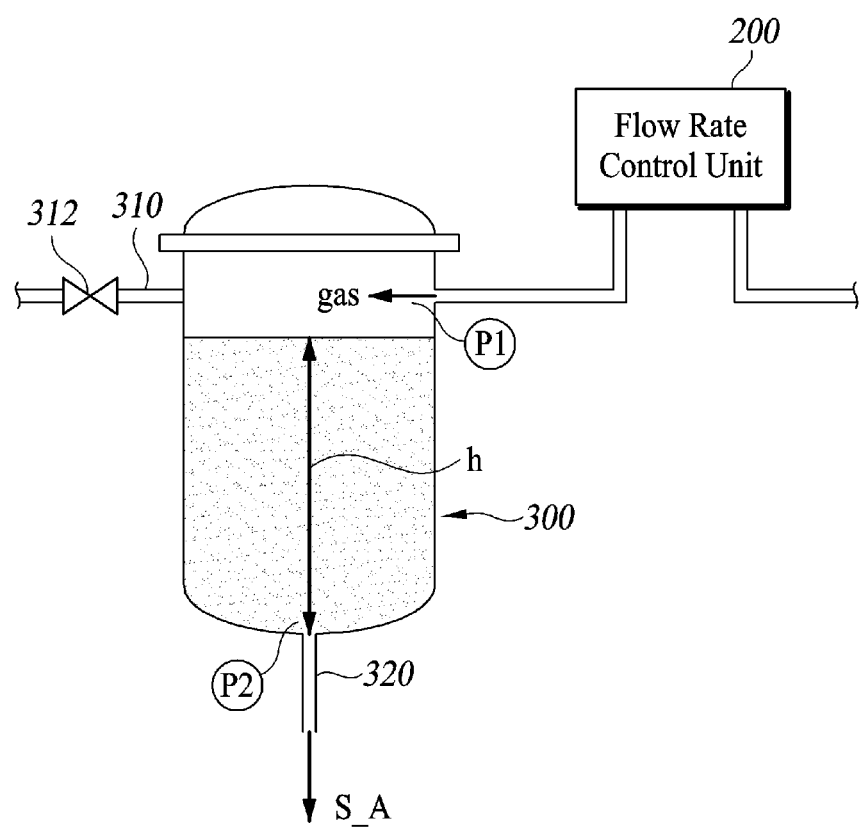
FIG. 16 is a block diagram for describing the Flow Control Principle of the Flow Control Unit of the Mass Production Apparatus.
Figure 17:
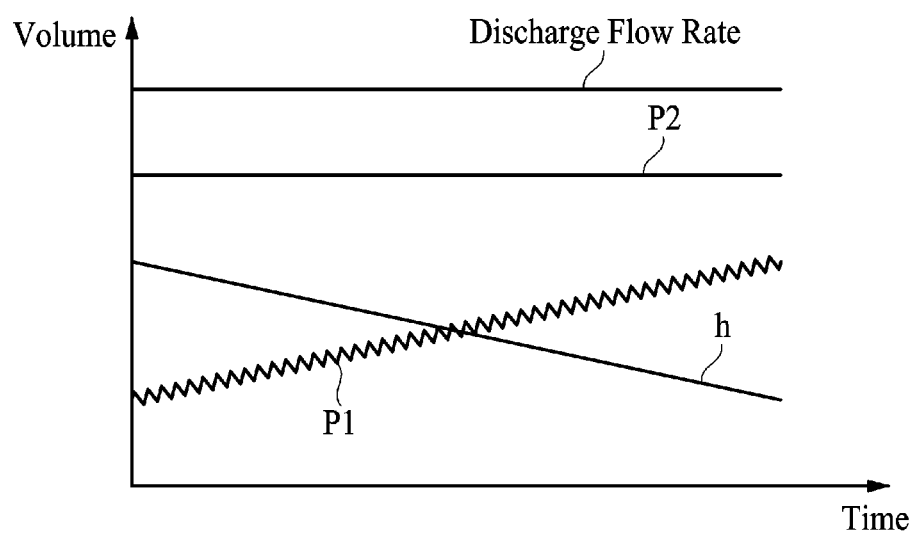
FIG. 17 is a graph illustrating the Flow Rate Control Principle of the Flow Rate Control Unit of the Mass Production Apparatus.

There are shown in FIG. 16 and FIG. 17 a block diagram for describing the flow control principle of the flow control unit of the mass production apparatus in accordance with an embodiment of the present invention and a graph illustrating a flow rate control principle of the flow control unit of the mass production apparatus according to another embodiment of the present invention, respectively.

FIG. 16 is Block Diagram for describing a Flow Control Principle of the Flow Rate Control Unit of the Mass Production Apparatus. FIG. 17: Graph illustrating the Flow Rate Control Principle of the Flow Rate Control Unit of the Mass Production Apparatus.

In FIGS. 16 and 17, the pressure P2 of the first material outlet 320 of the first material reservoir 300 can be expressed by the following equation:

$$P2=P1+pgh$$

wherein P1 is the first gas pressure introduced into the first material reservoir 300, p, the density of the first raw material, g, the gravitational acceleration, and h, the height from the first material outlet 320 to the top surface of the first raw material. That is, the pressure P2 of the first material outlet 320 can be represented by the sum of the pressure of the gas layer above the first material reservoir 300 or the first gas pressure P1 to be introduced and the hydrostatic pressure (pgh) of the first raw material at the first material outlet 320.

In closed systems of incompressible fluids, for example, for liquid such as water or organic solvents, the flow rate introduced and the flow rate discharged are known to be the same. The flow rate inside the closed system depends on the pressure difference or pressure gradient at the inlet and outlet of the closed system.

In an embodiment of the present invention, since a complete airtightness can be maintained at the multichannel microsphere forming unit 100 except for at the inlet and the outlet, the multichannel forming unit 100 can be considered as a closed system. Further, in an embodiment of the present invention, a constant pressure, for example, an atmospheric pressure level, can be maintained at the outlet of the multichannel forming unit 100. Accordingly, if both pressure P2 of the first material outlet 320 delivering the raw material to the multichannel microsphere forming unit 100 and pressure of the second material outlet 420 are kept constant, the flow rate of the fluids running through the multichannel microsphere forming unit 100 can be held constant.

During the production of the microspheres using the apparatus according to an embodiment of the present invention, the first material inlet 310 is to be closed using the first material inlet valve 312, allowing the first material reservoir 300 to be in fluid communication only with the first flow control line 210 and the first material outlet 320, resulting in the flow rate of the first raw material flowing through the first material outlet 320 corresponding to that of the first gas introduced into the first material reservoir 300.

In the graph of FIG. 17, the first gas flow rate is illustrated as being equal to the flow rate of the first raw material discharged to the first material outlet 320. Further, in the graph of FIG. 17, the discharge flow rate of the first gas and the pressure P1 of the first gas introduced are shown as fluctuations having a relatively small amplitude. The flow rate and the pressure P1 of the first inlet gas will fluctuate at a frequency corresponding to the cycle of the flow rate control unit 200 as a consequence of the flow rate control unit 200 may be being, for example, a mechanical pump operating at a constant frequency or cycle, and the first gas is compressible.

If the pressure P2 of the first material outlet 320 fluctuates according to the pressure P1 of the first gas introduced, it results in both the flow rate discharged through the first material outlet 320 and the flow rate delivered to the multichannel microsphere forming unit 100 fluctuating accordingly.

In an embodiment of the present invention, the first gas is introduced into the gas layer above the first flow reservoir through the first flow control line of the flow rate control unit 200. As a consequence of the gas layer above the first flow reservoir, however, having a volume greater than the flow rate of the first gas introduced, the pressure fluctuation of the introduced first gas can be leveled off or attenuated in the entire gas layer above the first flow reservoir, allowing the upper gas layer to press down the surface of the first raw material at a uniform pressure without fluctuation, allowing the pressure P2 and flow rate of the first material outlet 320 to be kept constant, i.e., without fluctuation.

Further, as the microspheres get formed in the apparatus in accordance with an embodiment of the present invention, the fluid level h of the first raw material stored in the first material reservoir 300 will gradually decrease, resulting in a corresponding decrease in the hydrostatic pressure pgh due to the weight of the first raw material, which, in turn, as a consequence of the reduced fluid level h and the hydrostatic pressure pgh, results in a corresponding increase in the pressure of the introduced first gas which was initially introduced into the multichannel microsphere forming unit 100 from the flow control unit 200 at a constant flow rate.

In order for the microspheres formed in the multichannel microsphere forming unit 100 to have a narrow size distribution or monodispersed, the process parameters of the multichannel microsphere forming unit 100 is strictly controlled, in particular, the flow rates therewithin. If the flow rate of the raw materials introduced into the multichannel microsphere forming unit 100 is not constant or fluctuates in a short period, i.e., fluctuates rapidly, it results in the microsphere forming conditions varying accordingly and the microspheres formed having a broad size distribution.

For a mass production of microspheres involving a multichannel microsphere forming unit 100 incorporating therein, for example, more than hundred microchannels, a relatively large amount of raw materials, for example, the first and second raw materials in the present embodiment, need to be introduced thereinto, as compared to laboratory-scale production equipment involving a multichannel forming unit 100 incorporating therein only a few microchannels. In addition, the frequency of process interruptions due to a raw material replacement should be minimized in mass production.

Further, in an embodiment of the present invention, in order for the microsphere forming process to be maintained for an extended period of time, a significant amount of the first raw material that have been sterilized is stored in the first material reservoir 300. By keeping the flow rate of the first gas supplied to the first material reservoir 300 constant, it is possible to keep constant the flow rate of the first raw material discharged from the first material reservoir 300, that is, the first raw material delivered to the multichannel microsphere forming unit 100, using the flow rate control unit 200. In addition, the flow rate can be smoothly maintained, i.e., without fluctuation, by forming a gas layer, for example, a gas buffer layer, on the upper portion of the first material reservoir 300 and by supplying the first gas to the gas layer through the flow rate control unit 200 and the first flow control line 210.

The flow rate control unit 200 and the mass production apparatus for microspheres according to an embodiment of the present invention are described using the first material reservoir 300 shown in FIGS. 16 and 17. The flow control of the second material reservoir 400 may be identical to the one for the first material reservoir 300.

Referring again to FIG. 14, the multichannel forming unit 100 of the apparatus according to an embodiment of the present invention receives the first raw material from the first material reservoir 300 and receive the second raw material from the second material reservoir 400. The multichannel microsphere forming unit 100 includes a plurality of microchannels through which the first raw material and the second raw material flow respectively. Using the principle as described above in FIGS. 2 through 5, microspheres are formed by the interaction of the first raw material and the second raw materials flowing through the respective microchannels and merging at the merging point thereof.

Formed microspheres are transferred to the product reservoir 500 through the product outlet 110, the product reservoir 500 including therein a solution that is similar or identical to the first raw material stored in the first material reservoir 300 such as, for example, PVA dissolved purified water. The dispersion solution reservoir 700 comprising a dispersion solution introduces the dispersion solution to the product reservoir through the dispersion solution inlet valve 712 and the dispersion solution inlet 710. After the dispersion solution contained in the dispersion solution reservoir 700 is sufficiently introduced into the product reservoir 500, the dispersion solution inlet valve 712 mounted in the product reservoir 500 is closed. Thereafter, the product inlet valve 512 is opened, connecting the product inlet 510 of the product reservoir 500 to the product outlet 110 of the multichannel microsphere forming unit 100. The microspheres formed in the multichannel microsphere forming unit 100 are introduced into the dispersion solution stored in the product reservoir 500, the dispersion solution preventing the newly produced microspheres from being aggregated. The product inlet valve 512 is to be closed after the completion of the microsphere manufacturing process. Thereafter, the dispersion solution containing the produced microspheres are to be discharged through the outlet 520 to be further processed or treated, such as sieving and filtering, depending on the final product requirements.

Figure 18:
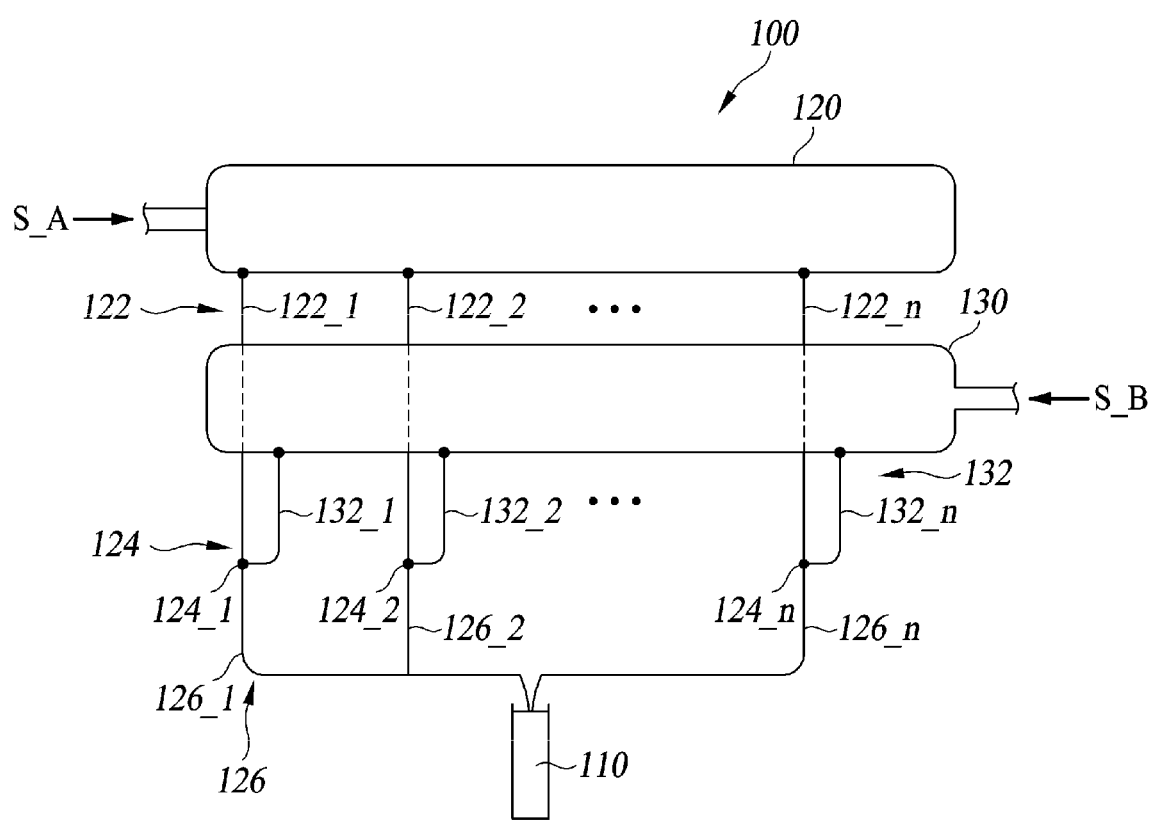
FIG. 18 is a block diagram illustrating the Channel-to-Channel Fluidic Connection Relationship in the Multichannel Microsphere Forming Unit of the Mass Production Apparatus according to an exemplary embodiment of the present invention.

FIG. 18 is Block Diagram illustrating a Channel-to-Channel Fluidic Connection Relationship in the Multichannel Microsphere Forming Unit of the Mass Production Apparatus according to an exemplary embodiment of the present invention.

There is shown in FIG. 18 a multichannel microsphere forming unit 100 of the mass production apparatus according to an embodiment of the present invention comprising a first inlet manifold 120, a second inlet manifold 130, a plurality of first microchannels, a plurality of second microchannels and a plurality of third microchannels.

Detailed specifications of individual microchannels and principles of microsphere formation have been described above with reference to FIGS. 3 to 5. For the sake of brevity, repeated descriptions relating thereto are omitted.

In the embodiment, the first inlet manifold 120 for receiving the first raw material delivered from the first material reservoir 300 is in fluid communication with the first material outlet 320 of the first material reservoir 300. The first inlet manifold 120 is also in fluid communication with the plurality of first microchannels 122;122_1-122_n and supplies the received first raw material to each of the first microchannels. The second inlet manifold 130 for receiving the second material from the second material reservoir 400 is in fluid communication with the second material outlet 420 of the second material reservoir 400. The second inlet manifold 130 is also in fluid communication with the plurality of second microchannels 132;132_1-132_n and supplies the received second raw material to each of the second microchannels. The second inlet manifold 130 is not directly connected to the plurality of the first microchannels 122;122_1-122_n. In this regard, a plurality of first microchannels 122;122_1-122_n which pass under the second inlet manifold 130 is depicted with dotted lines in FIG. 18.

Respective first microchannel and second microchannel are merged at a plurality of merging points 124;124_1-124_n. A plurality of third microchannels 126;126_1-126_n are connected to a plurality of merging points 124;124_1-124_n, respectively, the plurality of third microchannels 126;126_1-126_n extending from the plurality of merge points 124;124_1-124_n to the product outlet 110. The first raw material flowing through the plurality of first microchannels 122;122_1-122_n and the second raw material flowing through the plurality of second microchannels 132;132_1-132_n are to be merged at the plurality of merging points 124;124_1-124_n, resulting in the formation of microspheres thereat. The mixed solution of the first raw material and the second raw material including therein the formed microspheres flow through the plurality of third microchannels 126;126_1-126_n to be collected at the product outlet 110.

For a mass production, the multichannel microsphere forming unit 100 of the apparatus according to an embodiment of the present invention may need to incorporate therein a large number of microchannels, for example, over a hundred microchannels. In order for the microspheres formed in each of the microchannels to be of an even sized, that is, microspheres having a narrow size distribution or monodispersed, important parameters in microsphere formation in each microchannel, in particular, the flow rate of the materials therein and the dimension thereof, should be strictly controlled.

As described above, the size and the size distribution of the microspheres formed are mainly determined by few parameters, for example, the polymer concentration in each of the solutions, the flow rate of the materials and the consistency thereof in the microchannels and the dimension of the microchannels.

In an embodiment of the present invention, the concentration and the viscosity of the respective raw materials entering each of the dedicated microchannels are substantially the same for the first raw material and the second raw material because the first and second raw materials flowing into the plurality of first or second microchannels 122;122_1-122_n, 132;132_1-132_n are supplied from the first or second material reservoirs 300, 400 after being stirred enough therein to be uniformly mixed. Further, in an embodiment of the present invention, the multichannel microsphere forming unit 100 can be formed with high dimensional accuracy on a rigid material such as silicon wafer, glass or PDMS through semiconductor processes. As is known, current semiconductor processes are capable of providing ultra-fine microchannel structures much smaller than 50 μm. Since the microchannels of the multichannel microsphere forming unit 100 are formed of the same semiconductor material using ultra-fine processes, the microchannels therein have the uniform channel dimensions and wall wettability.

Once the diameter of the microspheres desired is set, the first step in optimizing the mass production of microspheres is to design the multichannel microsphere forming unit 100, based on the results disclosed hereinabove, to be incorporated in the mass production apparatus, and the first step in designing the multichannel forming unit 100 is to fix the material constituting the multichannel microsphere forming unit 100, for this will fix the wall wettability. As the next step, the microchannel dimension needed should get fixed, for and the microchannel dimension is the next easiest parameter to control, and the microchannel dimension must meet, according to the results obtained and described herein above, one of the following criteria: (1) the cross sectional area of the microchannel should be within 30% of the cross sectional area of the microsphere to be formed; (2) in case that cross section of the microchannel is a square, i.e., the width and the depth are the same, the width and the depth of the microchannel should be within 30% of the diameter of the microsphere to be formed; or (3) in case that the cross sectional of the microchannel is not square, ie., a rectangle, at least one of the side thereof should be within within 30% of half of the diameter of the microsphere to be formed.

In order to obtain microspheres with uniform size and narrow size distribution, i.e., monodisperse, strict control of the flow rate in each of the microchannels in the multichannel microsphere forming unit 100 should be tightly controlled. If the introduction pressure of the first or second raw material is different for each microchannel at the point where the first or second raw material is introduced into each of the plurality of first or second microchannels 122;122_1-122_n, 132;132_1-132_n, it results in the flow rate through the channel varying from microchannel to microchannel. In addition, if the inlet pressure changes or fluctuates over time, it results in the flow rate in the microchannels varying at the plurality of merging points 124;124_1-124_n, where the microspheres are formed, leading a wide size distribution in the microspheres formed.

In an embodiment of the present invention, the first and second manifold 120, 130 has a volume that is considerably larger than the size and the flow rate of the plurality of first and second microchannels 122;122_1-122_n, 132;132_1-132_n, respectively. More specifically, in an embodiment of the present invention, the first inlet manifold 120 has a volume sufficiently large enough to provide substantially the same flow rate to the plurality of first microchannels 122; 122_1-122_n, and the second inlet manifold 130, a volume large enough to provide substantially the same flow rate to the plurality of second microchannels 132;132_1-132_n.

As can be seen in FIG. 18, the path for the flow of the first raw material at the leftmost microchannel is shorter than the same at the rightmost microchannel as the latter path includes an additional path for the flow inside the first inlet manifold 120, wherein the leftmost microchannel path is from the first path of the first microchannel and the first path of the third microchannel to the product outlet 110, and the rightmost channel path is from the nth path of the first microchannel and the nth path of the third microchannel to the product outlet 110. Unless the first and the second inlet manifold 120, 130 have sufficiently large volume, the pressure gradient along the length of the first or the second inlet manifold 120, 130 could occur, resulting the inlet pressure at each microchannel being different from one another.

However, inside pressure of each manifold according to an embodiment of the present invention is constant overall. The first or the second inlet manifold 120, 130 has considerably larger volume compared to the sizes and the flow rates of the plurality of first or second microchannels 122; 122_1-122_n, 132;132_1-132_n. The pressures within each manifold could be considered constant by averaging effect over the entire volume of the manifold, resulting in the first and the second inlet manifold 120, 130 functioning as a pressurized source for each dedicated microchannels, the plurality of first microchannels 122;122_1-122_n and the plurality of second microchannels 132;132_1-132_n, respectively. That is, the inlet pressure of the first raw materials from the first inlet manifold 120 to each of the first microchannels 122;122_1-122_n are substantially the same, and the same applies to the second inlet manifold 130. Such a manifold having considerably larger volume provides a constant pressure of the first or second raw material introduced into the first or second microchannels 122;122_1-122_n, 132;132_1-132_n, respectively, without fluctuation during the whole process.

Thus, in an embodiment of the present invention, each pressure gradients along the plurality of first microchannels 122;122_1-122_n or the plurality of second microchannels 132;132_1-132_n are substantially identical and are constant during the process, resulting in the flow rates being substantially the same throughout the process.

Figure 19:
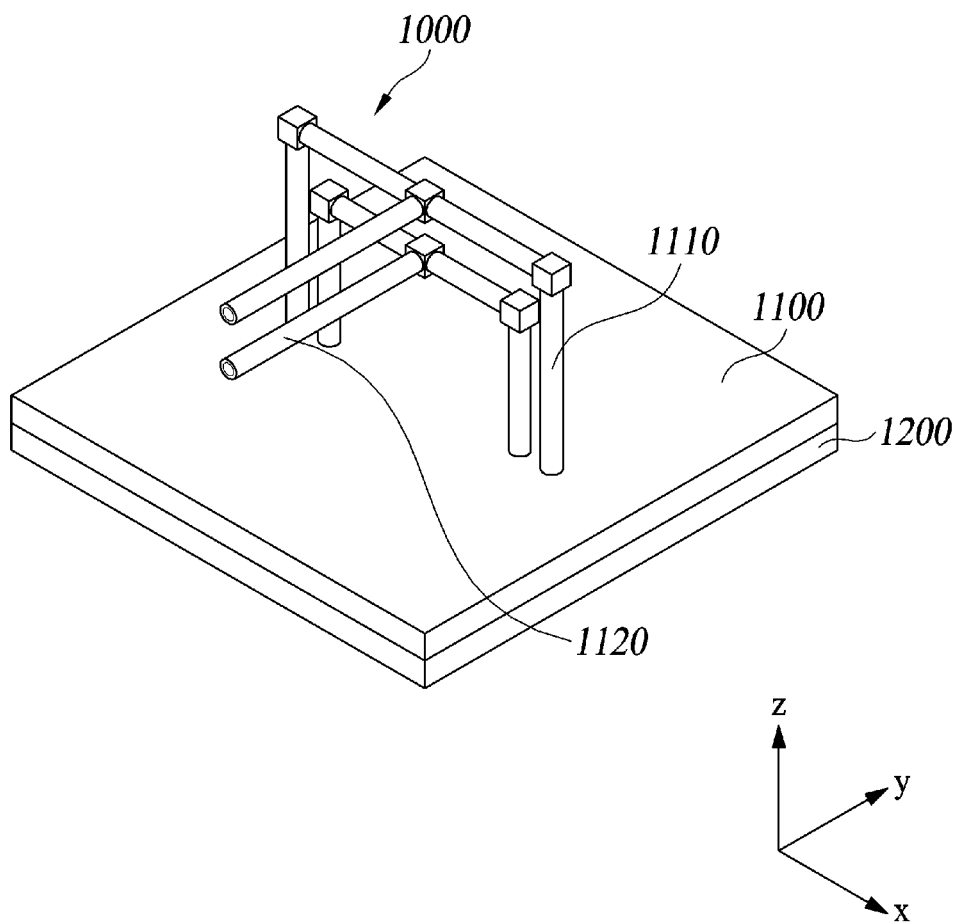
FIG. 19 is an assembled perspective view of the Multichannel Microsphere forming Unit of the Mass Production Apparatus according to an embodiment of the present invention.
Figure 20:
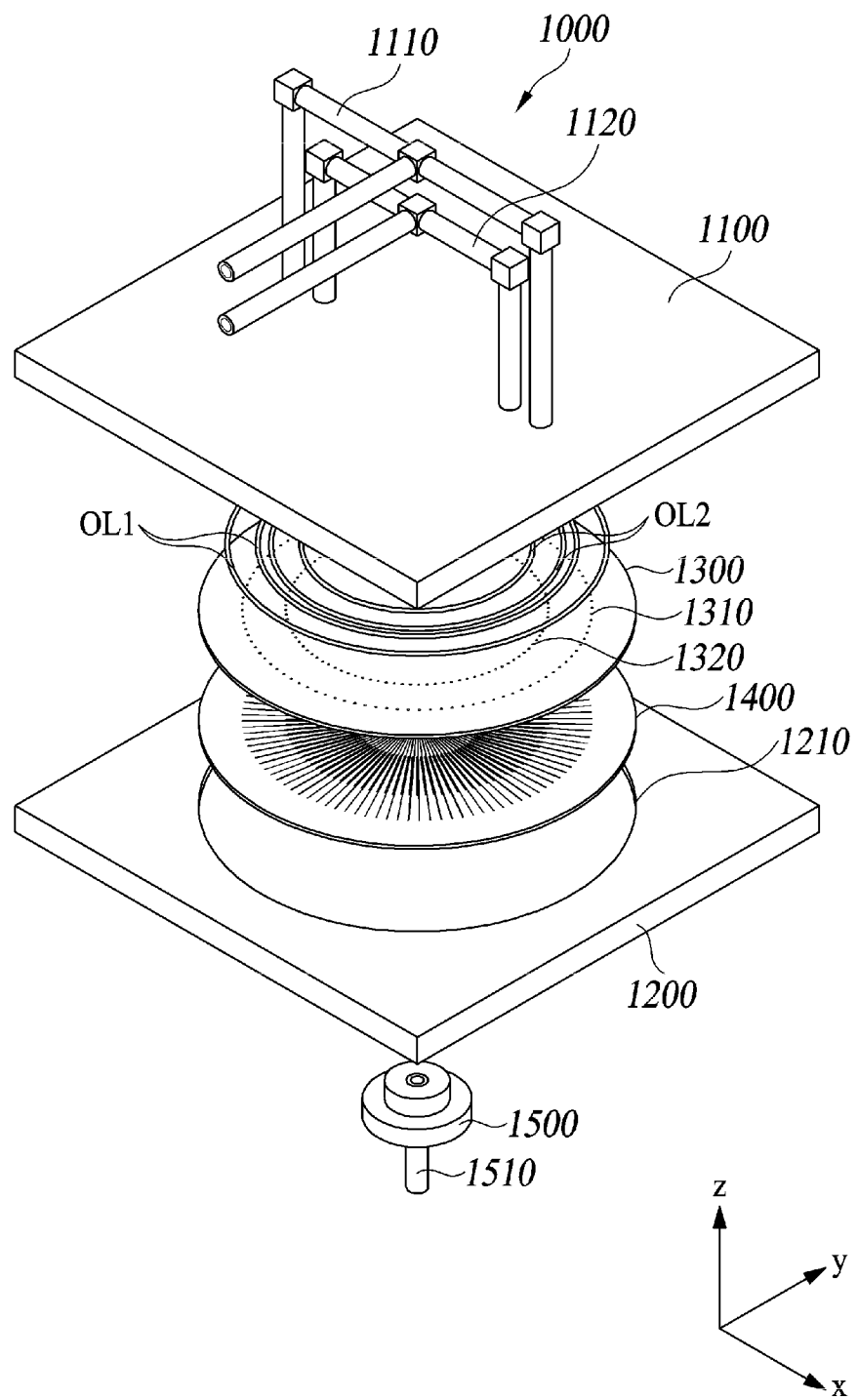
FIG. 20 is an exploded perspective view of the Multichannel Microsphere Forming Unit of FIG. 19.
Figure 21:
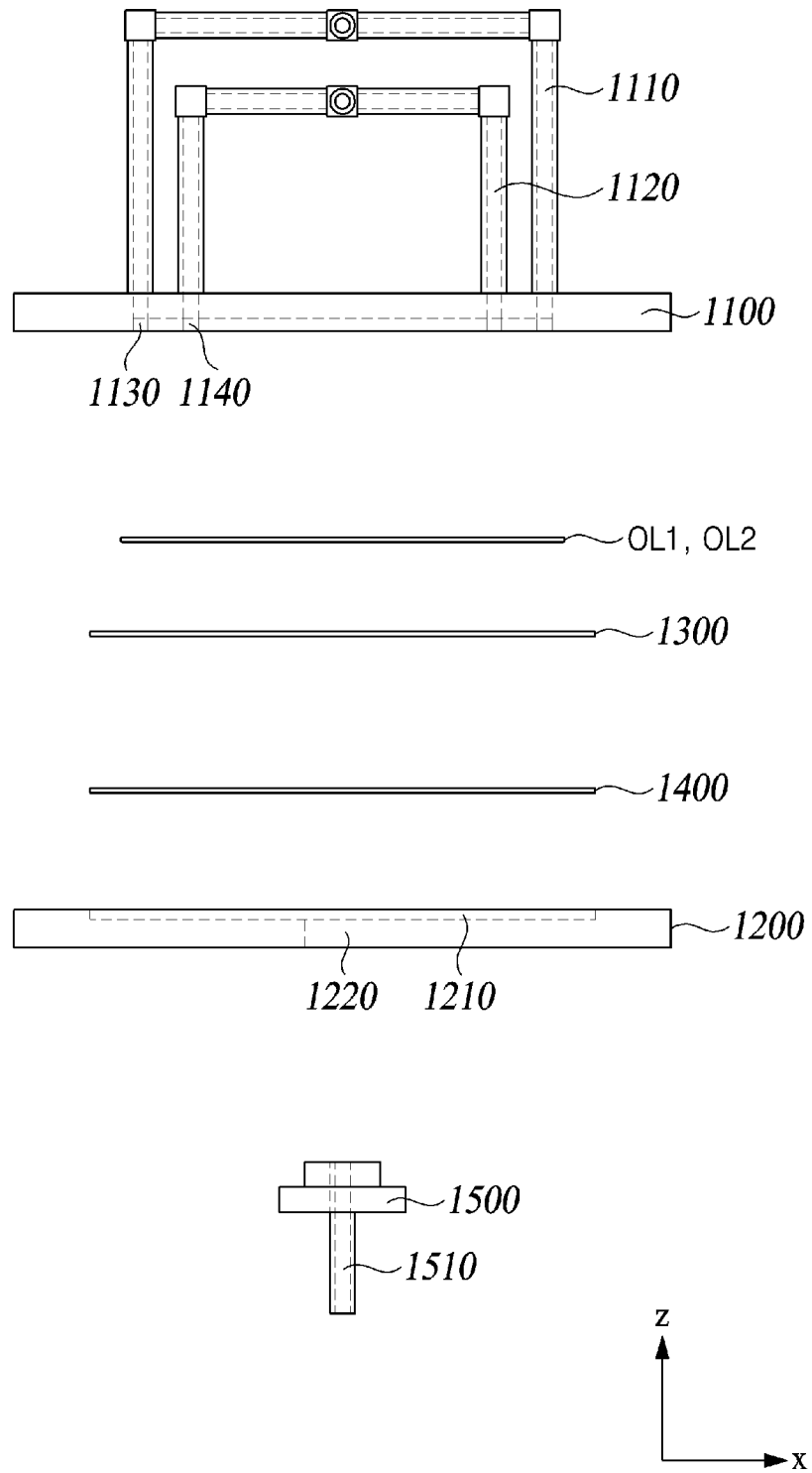
FIG. 21 is an exploded perspective view of the Multichannel Microsphere forming Unit of FIG. 19.

There are shown in FIGS. 19 to 24 an assembled perspective view of a multichannel microsphere forming unit of the mass production apparatus for microspheres according to an embodiment of the present invention, an exploded perspective view of the multichannel microsphere forming unit of FIG. 19, an exploded perspective front view of the multichannel microsphere forming unit of FIG. 19, an assembled perspective front view of the multichannel microsphere forming unit of FIG. 19, a bottom view of the upper case of FIG. 19 and a top view of the lower case of FIG. 21, respectively.

Figure 22:
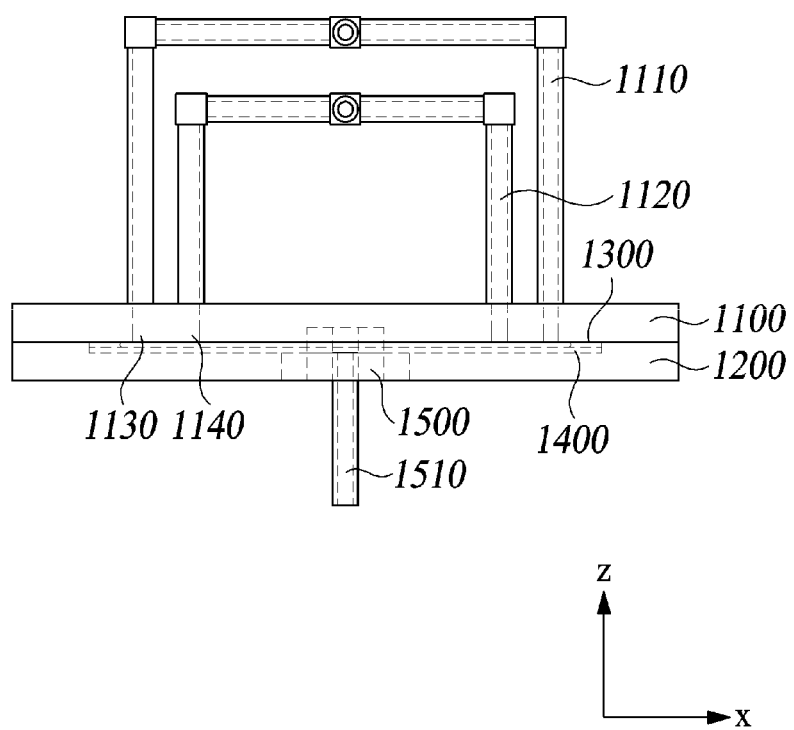
FIG. 22 is an assembled perspective front view of the Multichannel Microsphere Forming Unit of FIG. 19.
Figure 23:
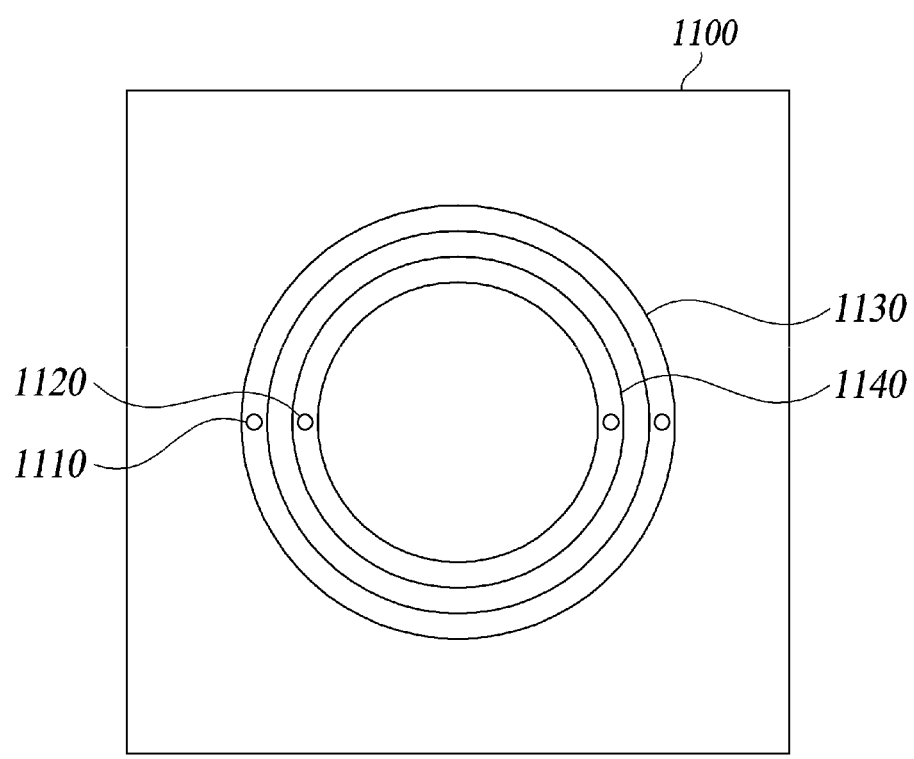
FIG. 23 is a bottom view of the Upper Case of FIG. 19.
Figure 24:
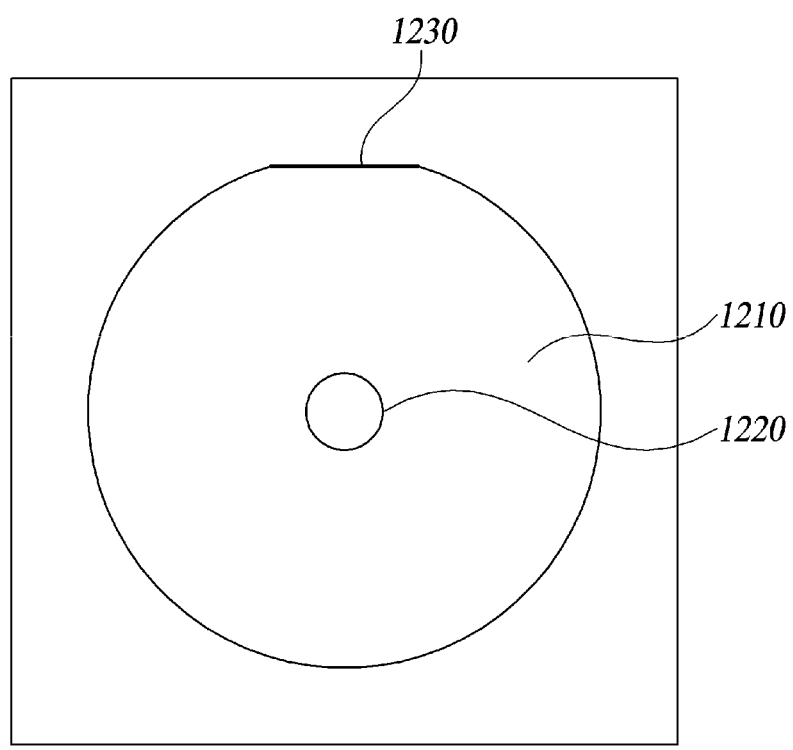
FIG. 24 is a top view of the Lower Case of FIG. 21

FIG. 19 is Assembled perspective view of the Multichannel Microsphere Forming Unit of the Mass Production Apparatus according to an embodiment of the present invention. FIG. 20 is Exploded perspective view of the Multichannel Microsphere Forming Unit of FIG. 19. FIG. 21 is Exploded perspective front view of the Multichannel Microsphere Forming Unit shown in FIG. 19. FIG. 22 is Assembled perspective front view of the Multichannel Microsphere Forming Unit shown in FIG. 19. FIG. 23 is Bottom view of the Upper Case shown in FIG. 19. FIG. 24 is Top view of the Lower Case shown in FIG. 21.

Referring FIGS. 17 to 22, the multichannel microsphere forming unit 100 of the mass production apparatus for microspheres according to an embodiment of the present invention comprises an upper case 1100, a lower case 1200, a plurality of O-rings OL1, OL2, an upper multichannel plate 1300, a lower multichannel plate 1400 and product outlets 1500, 1510. In assembly, the upper case 1100 and the lower case 1200 are fastened to each other. The plurality of O-rings OL1, OL2, the upper multichannel plate 1300 and the lower multichannel plate 1400 are disposed between the upper case 1100 and the lower case 1200. The upper case 1100 and the lower case 1200 are made of a corrosion-resistant material such as stainless steel or a rigid plastic. Although not shown, the upper case 1100 and the lower case 1200 are fastened to each other by fastening means such as bolts. However, the present invention is not limited thereto. In some embodiments, the upper case 1100 and the lower case 1200 are fastened to each other by tightening means such as a clamp or adhesive means such as an adhesive or through welding.

The upper case 1100 and the lower case 1200 have the same shape. In the illustrated embodiment, the upper case 1100 and the lower case 1200 are rectangular plates. However, the present invention is not limited thereto. The upper case 1100 and the lower case 1200 can be in any shape such as discs capable of properly positioning the upper multichannel plate 1300 and the lower multichannel plate 1400 therebetween.

The upper case 1100 comprises a first inlet pipe 1110, a second inlet pipe 1120, a first annular manifold 1130 and a second annular manifold 1140. The first inlet pipe 1110 and the second inlet pipe 1120 are disposed on the upper surface of the upper case 1100. The first annular manifold 1130 and the second annular manifold 1140 are formed on the lower surface of the upper case 1100.

The first inlet pipe 1110 is in fluid connection with the first material outlet 320 of the first material reservoir 300 and the other end is in fluid connection with the first annular manifold 1130 passing through the upper case 1100. The first raw material is supplied from the outside of the multichannel microsphere forming unit 100 through the first inlet pipe 1110 and is delivered to the first annular manifold 1130 at the lower surface of the upper case 1100.

The second inlet pipe 1120 is in fluid connection with the second material outlet 420 of the second material reservoir 400, and the other end, in fluid connection with the second annular manifold 1140 passing through the upper case 1100. The second raw material is supplied from the outside of the multichannel microsphere forming unit 100 through the second inlet pipe 1120 and is delivered to the second annular manifold 1140 at the lower surface of the upper case 1100.

In one embodiment of the invention shown, the first inlet pipe 1110 and the second inlet pipe 1120 are branched at the upper portion of the upper case 1100, allowing the first annular manifold 1130 or the second annular manifold 1140 to be connected with two branched pipes, respectively. However, the present invention is not limited thereto. In other embodiments, the first annular manifold 1130 or the second annular manifold 1140 can be connected with a single inlet pipe or branched inlet pipes having more than three branches.

The first annular manifold 1130 and the second annular manifold 1140 are an annular recess formed in the lower surface of the upper case 1100. The first annular manifold 1130 is disposed radially outward of the second annular manifold 1140. In the illustrated embodiment, the radial cross-sections of the first annular manifold 1130 and the second annular manifold 1140 are substantially the same. However, the present invention is not limited thereto. For example, the second annular manifold 1140 can have a larger radial cross-section than the first annular manifold 1130, resulting in the volumes of both manifolds being the same or close to each other.

The upper case 1100 is disposed on the upper portion of the upper multichannel plate 1300 and the plurality of O-rings OL1, OL2 are disposed between the upper case 1100 and the upper multichannel plate 1300. The plurality of O-rings OL1, OL2 comprise the first O-rings OL1 placed radially adjacent to the first annular manifold 1130 inwardly or outwardly and the second O-rings OL2 placed radially adjacent to the second annular manifold 1140 inwardly or outwardly. The plurality of O-rings OL1, OL2 prevent the fluids from leaking along the boundary layers between the upper case 1100 and the upper multichannel plate 1300, the fluids containing the first raw material or the second raw material. In the illustrated embodiment of the present invention, two first O-rings OL1 and two second O-rings OL2 are arranged. However, the present invention is not limited thereto. There may be less or more number of first O-rings OL1 and second O-rings OL2 provided a proper sealing is ensured.

The lower case 1200 includes a plate seating groove 1210 formed on the upper surface of the lower case 1200 and a product-exhausting hole 1220 passing through the lower case 1200 from the center of the lower case 1200.

The plate seating groove 1210 is formed on the upper surface of the lower case 1200 and is a recess having a shape corresponding to the outer shape of the upper multichannel plate 1300 and the lower multichannel plate 1400. The plate seating groove 1210 has a disk-like shape and includes a case alignment portion 1230 formed on one side of the circumferential region. The case alignment portion 1230 has a shape in which a part of the circumference of the circle is cut off. The upper multichannel plate 1300 and the lower multichannel plate 1400 also have a shape corresponding to the shape of the plate seating groove 1210 including the case alignment portion 1230, allowing the upper multichannel plate 1300 and the lower multichannel plate 1400 to be aligned with each other when placed inside the plate seating groove 1210.

The product-exhausting hole 1220 is disposed at the center of the lower case 1200, for example, at the center of the plate seating groove 1210. The microspheres formed inside the multichannel microsphere forming unit are collected at the product-exhausting hole 1220. The product-exhausting hole 1220 may form a common exhausting path for the plurality of microchannels in the multichannel microsphere forming unit 100. The product-exhausting hole 1220 is connected to the product-exhausting ports 1550, 1510 attached to the lower surface of the lower case 1200.

The product-exhausting ports 1500, 1510 comprise a coupling body 1500 and a product-exhausting pipe 1510. The product-exhausting pipe 1510 is fixed to the coupling body 1500 and the coupling body 1500 is fastened to the lower surface of the lower case 1200. The product-exhausting pipe 1510 is in fluid communication with the product-exhausting hole 1220 of the lower case 1200. The product-exhausting pipe 1510 extends to the product reservoir 500 and is used for collecting the microspheres formed in the multichannel microsphere forming unit 100 and for transferring them to the product reservoir 500.

Figure 25:
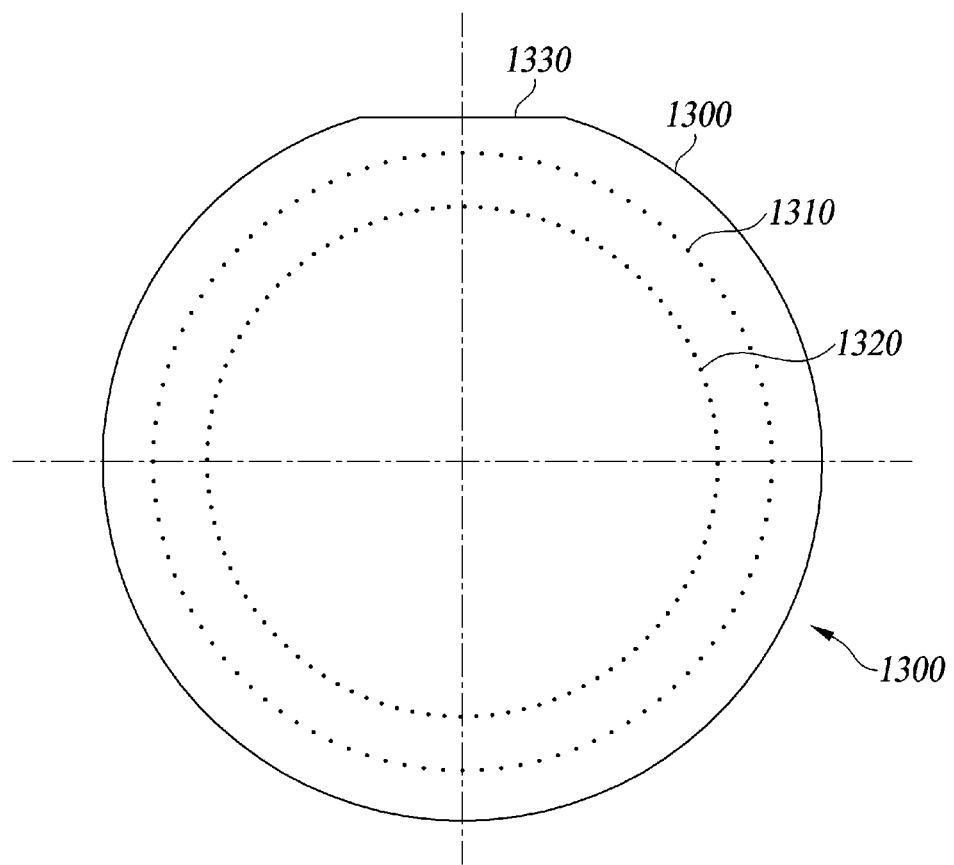
FIG. 25 is a top view of the Upper Multichannel Plate of the Multichannel Microsphere Forming Unit according to an embodiment of the present invention.

FIG. 25 is Top view of the Upper Multichannel Plate of the Multichannel Microsphere Forming Unit according to an embodiment of the present invention.

Referring FIGS. 19 to 20 and 25, the upper multichannel plate 1300 comprises a plurality of first channel connection holes 1310, a plurality of second channel connection holes 1320 and a plate alignment portion for the upper plate.

The plurality of first channel connection holes 1310 are arranged along a first circle having a first diameter. The plurality of second channel connection holes 1320 are arranged along a second circle having a second diameter smaller than the same of the first diameter. In an embodiment of the present invention, the plurality of first channel connection holes 1310 are disposed radially outward of the plurality of second connection holes, and the plurality of first channel connection holes 1310 and the plurality of second channel connection holes 1320 are disposed of coaxially.

The outer shape and dimensions of the upper multichannel plate 1300 correspond to the outer shape and dimensions of the plate seating groove 1210 of the lower case 1200 to be mounted. In an embodiment of the present invention, the upper multichannel plate alignment portion 1330 of the upper multichannel plate 1200 are fitted to the case alignment portion 1230 of the lower case 1200.

The upper multichannel plate 1300 is made of a rigid material capable of being formed with a high dimensional accuracy, such as a silicon wafer, a glass wafer, PDMS, or the like. In particular, in one embodiment of the present invention, the upper multichannel plate 1300 is made of a glass wafer. In an embodiment of the present invention, the plurality of first channel connection holes 1310 and the plurality of second channel connection holes 1320 have a relatively simple structure and are formed on the glass substrate having a higher toughness than a silicon wafer.

Figure 26:
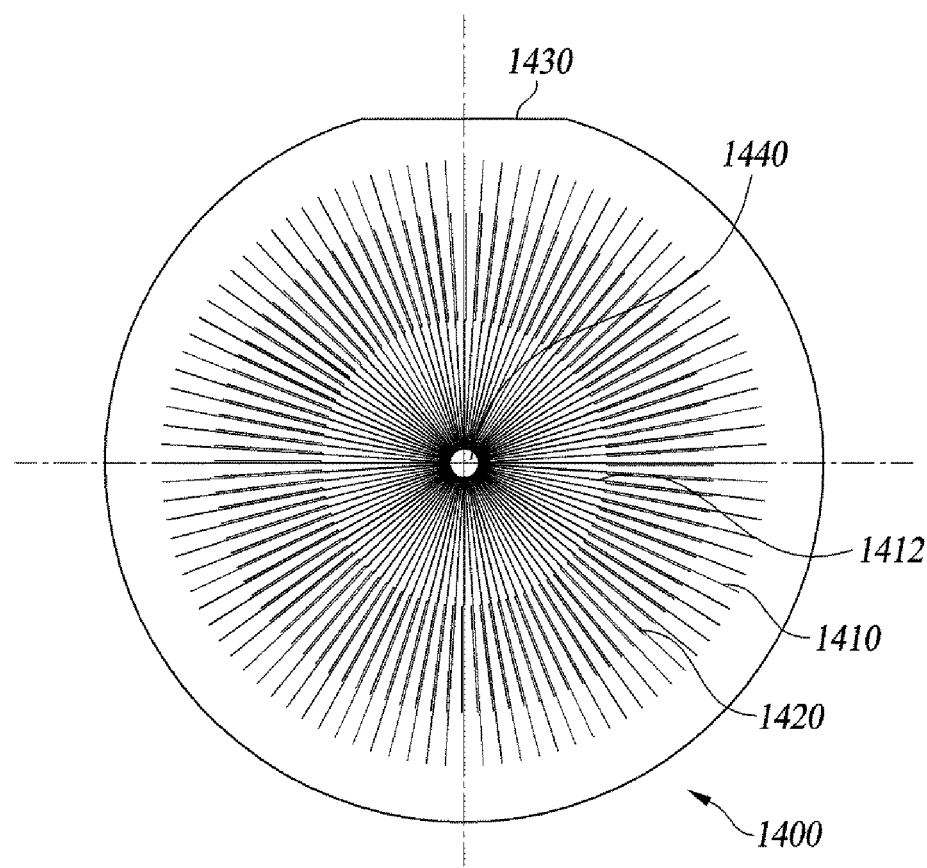
FIG. 26 is a top view of the Lower Multichannel Plate of the Multichannel Microsphere Forming Unit according to an embodiment of the present invention.

FIG. 26 is a top view of the lower multichannel plate of the multichannel microsphere forming unit according to an embodiment of the present invention. FIG. 26 is Top view of the Lower Multichannel Plate of the Multichannel Microsphere Forming Unit according to an embodiment of the present invention.

Referring FIGS. 19 to 22 and 26, the lower multichannel plate 1400 includes the plurality of first microchannels 1410, the plurality of second microchannels 1420, the plurality of third microchannels 1412 and a center through-hole 1440. Further, the lower multichannel plate 1400 is disposed between the upper multichannel plate 1300 and the lower case 1200.

The plurality of first microchannels 1410, the plurality of second microchannels 1420, and the plurality of third microchannels 1412 have a trench structure formed on the upper surface of the lower plate.

The plurality of first microchannels 1410 are arranged radially on the upper surface of the upper multichannel plate 1300. Each of the first microchannel 1410 is arranged radially from the center through-hole 1440. The plurality of second microchannels 1420 are arranged radially in parallel with the first microchannel 1410. The plurality of first microchannels 1410 and the plurality of second microchannels 1420 are merged at the merging point 1414. The plurality of third microchannels 1412 are arranged radially inward of the plurality of first microchannels 1410. One end of the third microchannel 1412 is connected to the merging point 1414 and the other end thereof is connected to the center through-hole 1440.

The outer shape and dimensions of the lower multichannel plate 1400 correspond to the outer shape and dimensions of the plate seating groove 1210 of the lower case 1200 to be mounted. In an embodiment of the present invention, the lower multichannel plate alignment portion of the lower multichannel plate 1400 is fitted to the case alignment portion 1230 of the lower case 1200.

The lower multichannel plate 1400 is made of a rigid material capable of being formed with a high dimensional accuracy, such as a silicon wafer, a glass wafer, PDMS, or the like. In particular, in an embodiment of the present invention, the lower multichannel plate 1400 is made of a crystalline or amorphous silicon wafer. In an embodiment of the present invention, microchannels having a high dimensional accuracy are appropriately formed on a silicon wafer as a consequence thereof having a high dimensional stability.

Figure 27:
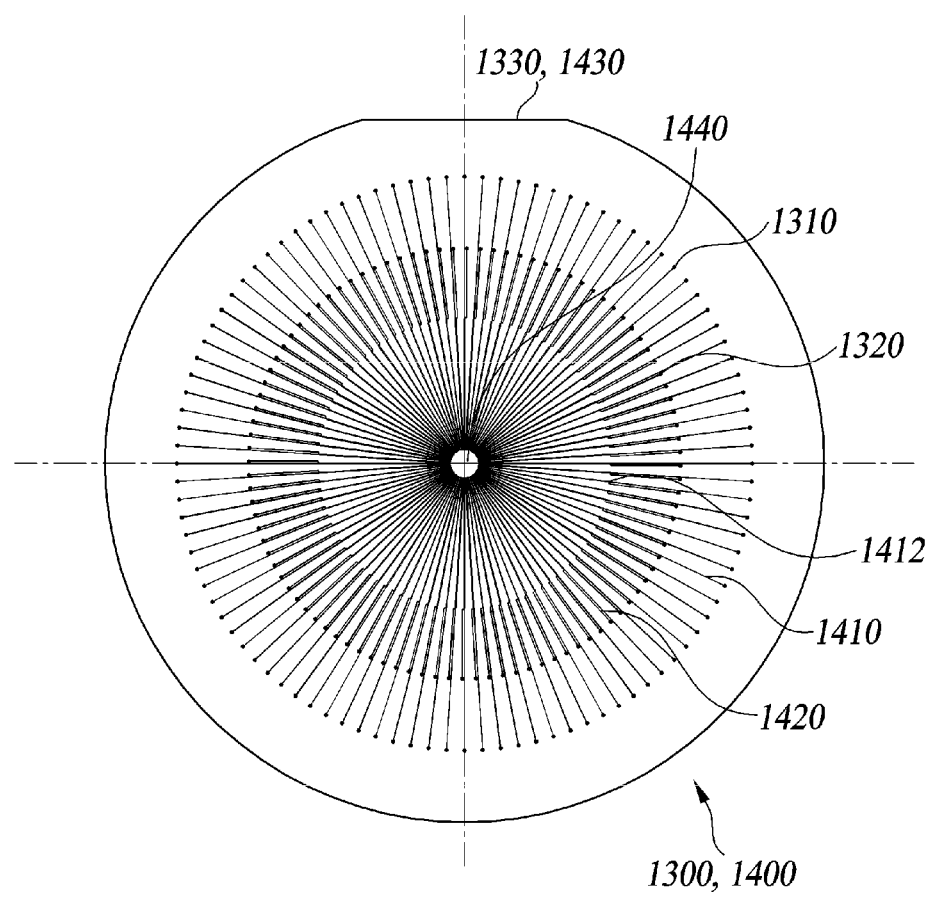
FIG. 27 is a top view showing the Upper Multichannel Plate overlapped with the Lower Multichannel Plate of the Multichannel Microsphere Forming Unit according to an embodiment of the present invention.
Figure 28:
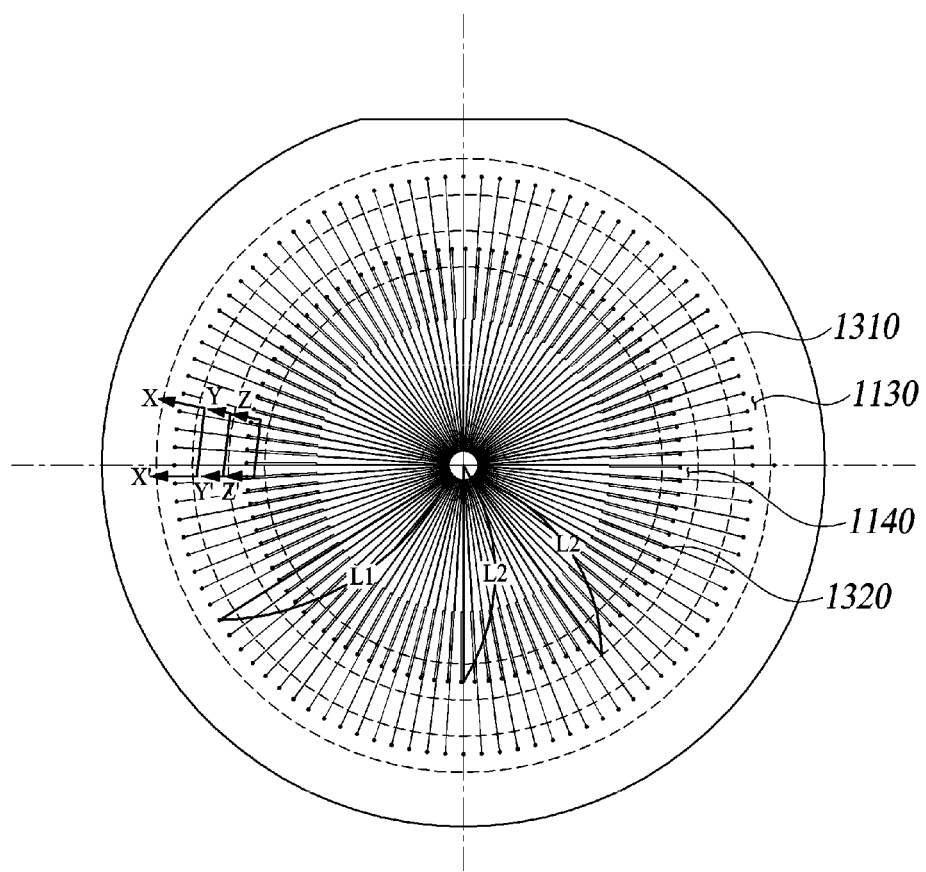
FIG. 28 is a top surface translucent diagram showing FIG. 27 with the First Annular Manifold and the Second Annular Manifold of the Upper Case in hidden line.

There are illustrated in FIGS. 27 to 31 a top view showing the upper multichannel plate overlapped with the lower multichannel plate of the multichannel microsphere forming unit according to an embodiment of the present invention, a top surface translucent diagram showing FIG. 27 with the first annular manifold and the second annular manifold of the upper case in hidden lines, a cross-sectional view of the upper case, the upper multichannel plate, and the lower multichannel plate taken along line X-X' in FIG. 28, a cross-sectional view of the upper case, the upper multichannel plate and the lower multichannel plate along the line Y-Y' in FIG. 28 and a cross-sectional view of the upper case, the upper multichannel plate, and the lower multichannel plate along the line Z-Z' in FIG. 28, respectively.

FIG. 27 is Top view showing the Upper Multichannel Plate overlapped with the Lower Multichannel Plate of the Multichannel Microsphere Forming Unit according to an embodiment of the present invention.

FIG. 28 is Top surface translucent diagram showing FIG. 27 with the First Annular Manifold and the Second Annular Manifold of the Upper Case in hidden lines.

Figure 29:
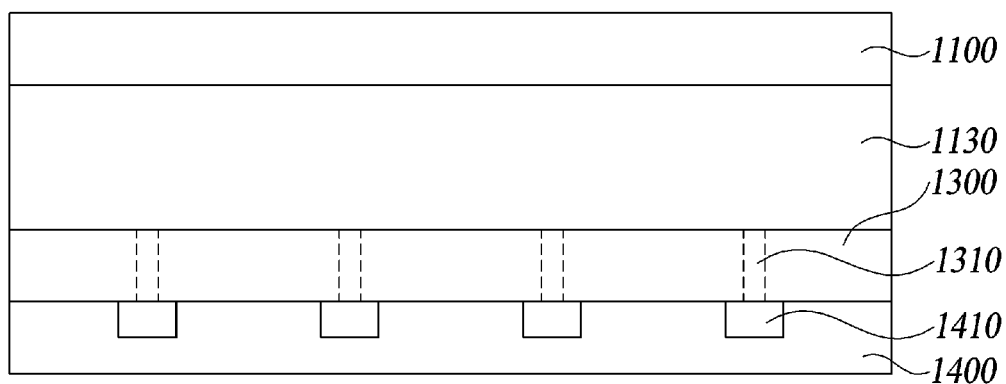
FIG. 29 is a cross-sectional view of the Upper Case, the Upper Multichannel Plate and the Lower Multichannel Plate taken along the line X-X' in FIG. 28.

FIG. 29 is Cross-sectional view of the Upper Case, the Upper Multichannel Plate and the Lower Multichannel Plate taken along line X-X' in FIG. 28.

Figure 30:
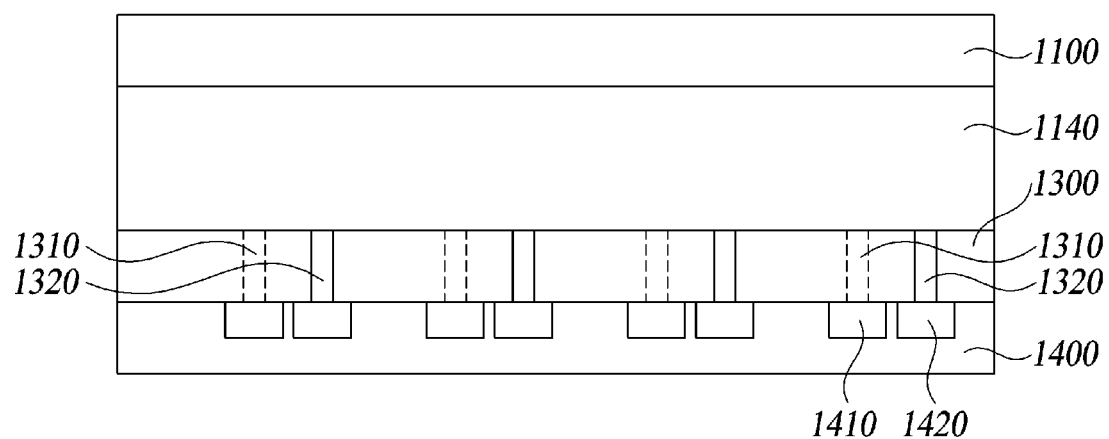
FIG. 30 is a cross-sectional view of the Upper Case, the Upper Multichannel Plate and the Lower Multichannel Plate taken along the line Y-Y' in FIG. 28.

FIG. 30 is Cross-sectional view of the Upper Case, the Upper Multichannel Plate and the Lower Multichannel Plate along the line Y-Y' in FIG. 28.

Figure 31:
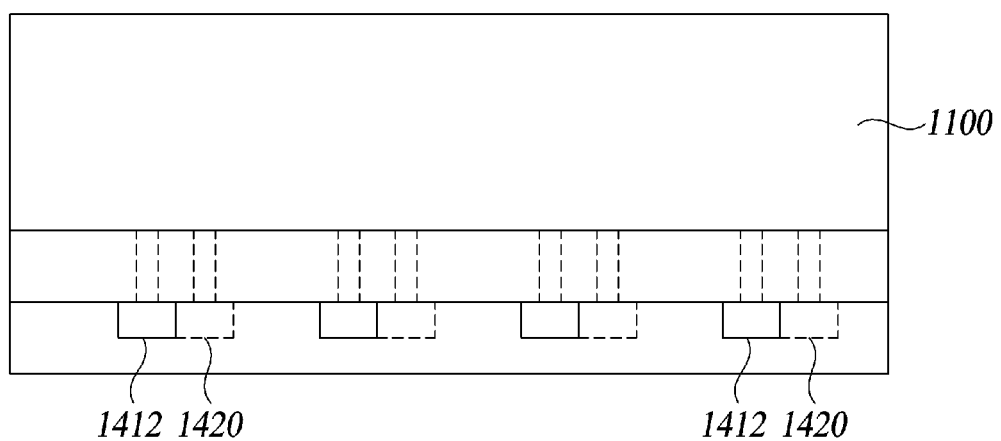
FIG. 31 is a cross-sectional view of the Upper Case, the Upper Multichannel Plate and the Lower Multichannel Plate taken along the line Z-Z' in FIG. 28.

FIG. 31 is Cross-sectional view of the Upper Case, the Upper Multichannel Plate and the Lower Multichannel Plate along the line Z-Z' in FIG. 28.

Referring FIGS. 27 to 31, the upper multichannel plate 1300 and the lower multichannel plate 1400 should be completely in contact and aligned when the multichannel forming portion 100 has been assembled. The open upper portion of the microchannels of the lower multichannel plate 1400 having a trench structure is closed off from the outside by the lower surface of the upper multichannel plate 1300. Thus, as described above, the microchannels for forming the microspheres are located between the upper multichannel plate 1300 and the lower multichannel plate 1400.

In an embodiment of the present invention, the plurality of first channel connection holes 1310 of the upper multichannel plate 1300 are disposed on the plurality of first microchannels 1410 (see FIG. 29). In addition, the plurality of second channel connection holes 1320 of the upper multichannel plate 1400 are disposed on the plurality of second microchannels 1420 (see FIG. 30).

The plurality of first microchannels 1410 are in fluid connection with the first annular manifold 1130 through the respective first microchannels 1410 and the plurality of second microchannels 1420 are in fluid connection with the second annular manifold 1140 through the respective second microchannel 1420. The plurality of first microchannels 1410 and the plurality of second microchannels 1420 are respectively merged at the plurality of merging points 1414. The plurality of third microchannels 1412 are respectively joined at the plurality of merging points 1414 and extend to the center through-hole 1440 (see FIG. 30).

The first annular manifold 1130 and the second annular manifold 1140 are provided with a significantly larger volume relative to the size and flow rate of the plurality of first microchannels 1410 and the plurality of second microchannels 1420. The pressure inside the first annular manifold 1130 and the second annular manifold 1140 are averaged over the entire volume and are constant during the process. Thus, the pressure of fluids introduced respectively from the plurality of first channel connection holes 1310 or the plurality of second channel connection holes 1320 to the plurality of first microchannels 1410 or the plurality of second microchannels 1420 are kept uniform over the relevant portions and during the process.

In addition, in an embodiment of the present invention, the plurality of first microchannels 1410 and the plurality of second microchannels 1420 are arranged radially in a plane, that is point-symmetrically with respect to the center point of the lower multichannel plate 1400. Accordingly, in an embodiment of the present invention, a plurality of flow paths from the plurality of first channel connection holes 1310 to the center through-hole 1440 through the plurality of first microchannels 1410 and a plurality of third microchannels 1412 are of the same first length L1. In addition, a plurality of flow paths from the plurality of second channel connection holes 1320 to the center through-hole 1440 through the plurality of second microchannels 1420 and the plurality of third microchannels 1412 are of the same second length L2. That is, the lengths of the corresponding flow paths formed by the microchannels are of substantially the same length with respect to each other. As described above, the first annular manifold 1130 or the second annular manifold 1140 which are in fluid connection with the plurality of first microchannel connection holes 1310 or the plurality of second microchannel connection holes 1320 are under a constant pressure without a pressure gradient along the position and are under an uniform pressure during the process. In addition, since all of the flow paths formed by microchannels are commonly connected to the center through-hole 1440 at which one same pressure applies, the pressure differences across the corresponding flow paths formed by the microchannels are substantially the same, that is, the pressure gradient of the flowing fluid in the corresponding flow path is constant for the corresponding channel. In an embodiment of the present invention, the first microchannel connection hole, the second microchannel connection hole, the first microchannel, the second microchannel and the third microchannel may each be several tens or more, for example, 100 or more in numbers. Since the flow conditions in the respective microchannels are substantially the same, the microspheres formed will be of the same size, leading to a narrow size distribution, i.e., monodispersed.

Figure 32:
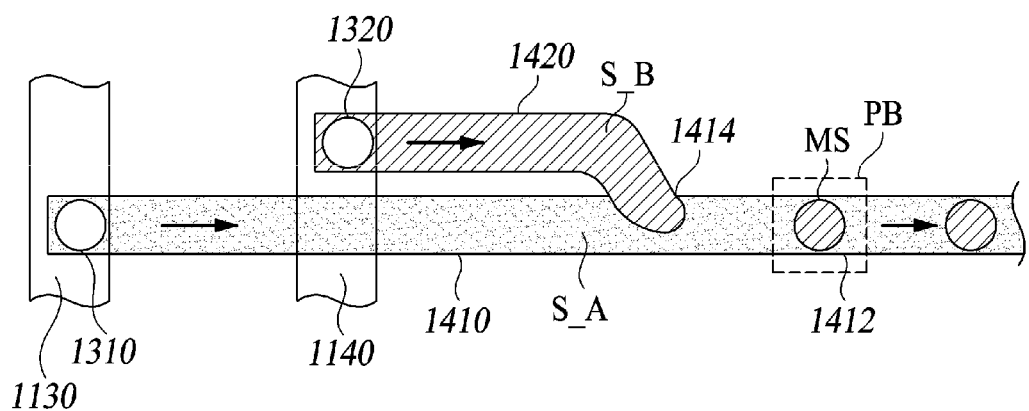
FIG. 32 is an exemplary schematic diagram illustrating the forming of microsphere in the Mass Production Apparatus according to an embodiment of the present invention.

There is shown in FIG. 32 an exemplary schematic diagram illustrating a process for forming of microspheres in the mass production apparatus according to an embodiment of the present invention.

FIG. 32 is Exemplary schematic diagram illustrating the Forming of Microspheres in the Mass Production Apparatus according to an embodiment of the present invention.

There is shown in FIG. 32 an enlarged view of one microsphere forming path of FIG. 31 and for simplicity of explanation, the size of each of the configurations is exaggeratively depicted.

In an embodiment of the present invention, the first annular manifold 1130 is connected to the first microchannel 1410 through a first microchannel connection hole 1310. An aqueous solution comprising the first raw material, for example, PVA, a surfactant, dissolved in pure water, is supplied to the first microchannels 1410 through the first annular manifold 1130. The second annular manifold 1140 is connected to the second microchannels 1420 through a second channel connection hole 1320. An aqueous solution comprising the second raw material, for example, PCL, a biodegradable polymer, dissolved in an oil, is supplied to the second microchannels 1420 through the second annular manifold 1140. At the merge point 1414, the second raw material having a hydrophobic surface is introduced from the second microchannels 1420 into the first raw material having a hydrophilic surface. As the amount of the second raw material introduced at the merging point 1414 increases, the flow pressure of the first raw material acting on the second introduced raw material correspondingly increases, resulting in, at the merging point 1414, the second raw material separating from the second microchannel 1420 and flow in a droplet form along with the first raw material having a relatively large flow rate in the third microchannel 1412. An isotropic external force acts on the droplets of the hydrophobic second raw material in the hydrophilic first raw material, making it possible for the droplets of the second raw material to maintain a spherical shape. The droplets thus formed harden with time, resulting in the formation of the desired microspheres.

If the respective flow rates in the microchannels are maintained constant, the microsphere formation process described above can be continuously repeated, resulting in a constant production cycle, implicating the amount of the first raw material and the second raw materials involved in one production cycle to be identical to those in other production cycles, which, in turn, leading to the formation of microspheres that are similar, chemically and physically or monodisperse.

One of the most critical parameters to be controlled in the mass production of monodisperse microspheres is the flow rate of the solutions/fluids and the proposed arrangement provide a unique solution for a precise/tight control thereof, namely: (1) a radially arranged multichannel structure in the multichannel microsphere forming unit 100 capable of providing the same flow length for each corresponding flow paths for the plurality of microchannels, i.e., capable of ensuring the same flow length for each corresponding material flowing in the respective microchannel or the same flow rate for each corresponding material flowing in the respective microchannel; and (2) a flow rate control unit 200 capable of supplying the first raw material and the second raw material from the respective reservoirs, i.e., the first raw material reservoir 300 and the second raw material reservoir 400, at constant flow rates to the multichannel microsphere forming unit 100.

Hereinafter, a mass production apparatus of monodisperse microspheres according to other embodiments of the present invention will be described. In other embodiments, substantially the same or similar components as those of the technical constructions included in the above-described embodiment of the present invention are referred to by the same reference numeral, and repetitive explanations thereof are omitted. Other embodiments of the present invention are described based on the differences from the embodiments of the present invention. In other embodiments, the added or modified technical constructions are referenced with an appended code 'a,' 'b' and 'c' at the end.

Figure 33:
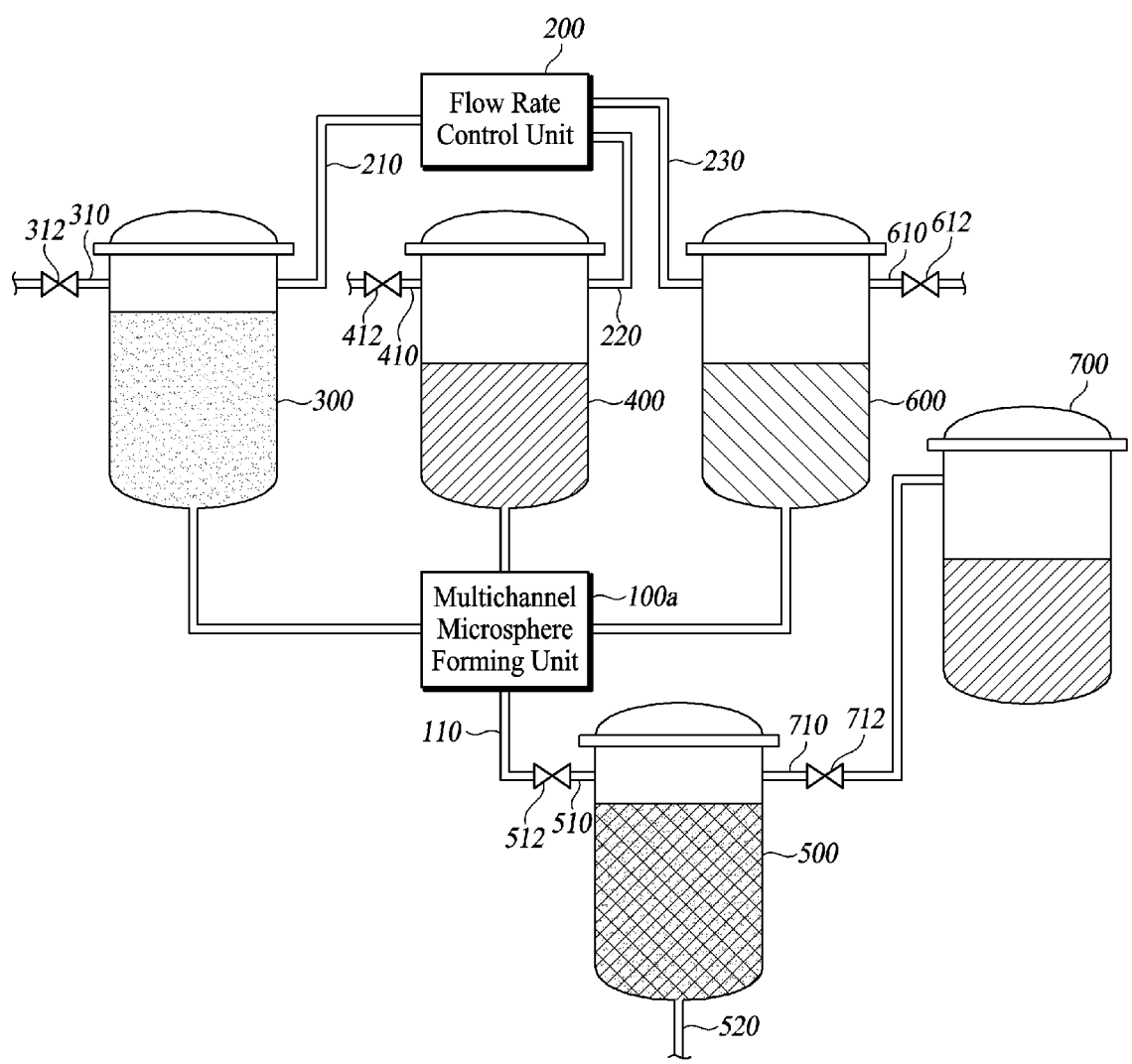
FIG. 33 is a block diagram of the Mass Production Apparatus according to another embodiment of the present invention.

FIG. 33 is a block diagram of the mass production apparatus for microspheres according to another embodiment of the present invention.

Referring to FIG. 33, the apparatus for mass-production of monodisperse microspheres according to another embodiment of the present invention further includes a third raw material reservoir 600 to the embodiment of the present invention shown in FIG. 14.

The third raw material reservoir 600 comprises an oil phase solution dissolved therein a third raw material, i.e., an organic solvent and a biodegradable polymer dissolved therein. For example, the third material may be polyglycolic acid (PGA) with Mn of about 45,000 or less, i.e., the biodegradable polymer, dissolved in dichloromethane (solvent, melting point 39.6° C.), i.e, oil solvent, at a concentration of 15 wt %, wherein Mn is the number average molecular weight obtained by dividing the molecular weight of the molecular species comprising polymeric compounds with molecular weight distribution by the number or mole fraction.

The second raw material and the third raw material may comprise substantially the same or similar organic solvent. Illustratively, the second material and the third material may have different concentrations of the biodegradable polymer dissolved in the same organic solvent, or different types of the biodegradable polymer to be dissolved in different organic solvent. However, the present invention is not limited thereto, and the organic solvent of the second material and the third materials may be composed of other solvents suitable depending on the kind of the biodegradable polymer to be dissolved therein.

The third raw material is sterilized using an appropriate sterilization process, for example, passing thereof through a sterilization filtration filter. The sterilized third raw material is then introduced into the third material reservoir 600 through a third material inlet 610. After the sterilized third raw material is sufficiently or completely introduced into the third material reservoir 600, the third material inlet valve 612 installed in the third material inlet is shut off, isolating the third material reservoir 600 from the outside, allowing the sterilization state to be maintained.

The first raw material stored in the first material reservoir 300, the second raw material stored in the second material reservoir 400 and the third raw material stored in the third material reservoir 600 are transferred to the multichannel microsphere forming unit 100a through the first material outlet 320, the second material outlet 420 and the third material outlet 620, respectively.

The flow control unit 200a is respectively in fluid communication with the first material reservoir 300 through the first flow control line 210, with the second material reservoir 400 through the second flow control line 220 and with the third material reservoir 600 through the third flow control line 230. The flow control unit 200a introduces a first gas having a first raw material flow rate into the first material reservoir 300, a second gas having a second raw material flow rate into the second material reservoir 400 and a third gas having a third raw material flow rate into the third material reservoir 600. The first gas, the second gas and the third gas are substantially the same kind of gas, for example, clean air or an inert gas.

FIG. 33 is Block diagram of the Microsphere Mass Production Apparatus according to another embodiment of the present invention.

The first raw material stored in the first material reservoir 300 is delivered to the multichannel microsphere forming unit 100a in an amount corresponding to the first raw material flow rate of the introduced first gas. The second raw material stored in the second material reservoir 400 is delivered to the multichannel microsphere forming unit 100a in an amount corresponding to the second raw material flow rate of the introduced second gas. In addition, the third raw material stored in the third material reservoir 600 is delivered to the multichannel microsphere forming unit 100a in an amount corresponding to the third raw material flow rate.

The multichannel microsphere forming unit 100a The multichannel forming unit 100a, receiving the first raw material from the first material reservoir 300, the second raw material from the second material reservoir 400 and the third raw material from the third raw material reservoir, includes a plurality of microchannels through which the first raw material, the second raw material, and the third raw material flow respectively. In this embodiment, after the initial microspheres are formed through the interaction of the first and the second raw materials as described above in FIGS. 4 and 5, the third raw material is then combined with the microspheres formed, for example, through mixing or encapsulation, to form multi-layered microspheres MS2. This known as a "Double Immersion".

Figure 34:
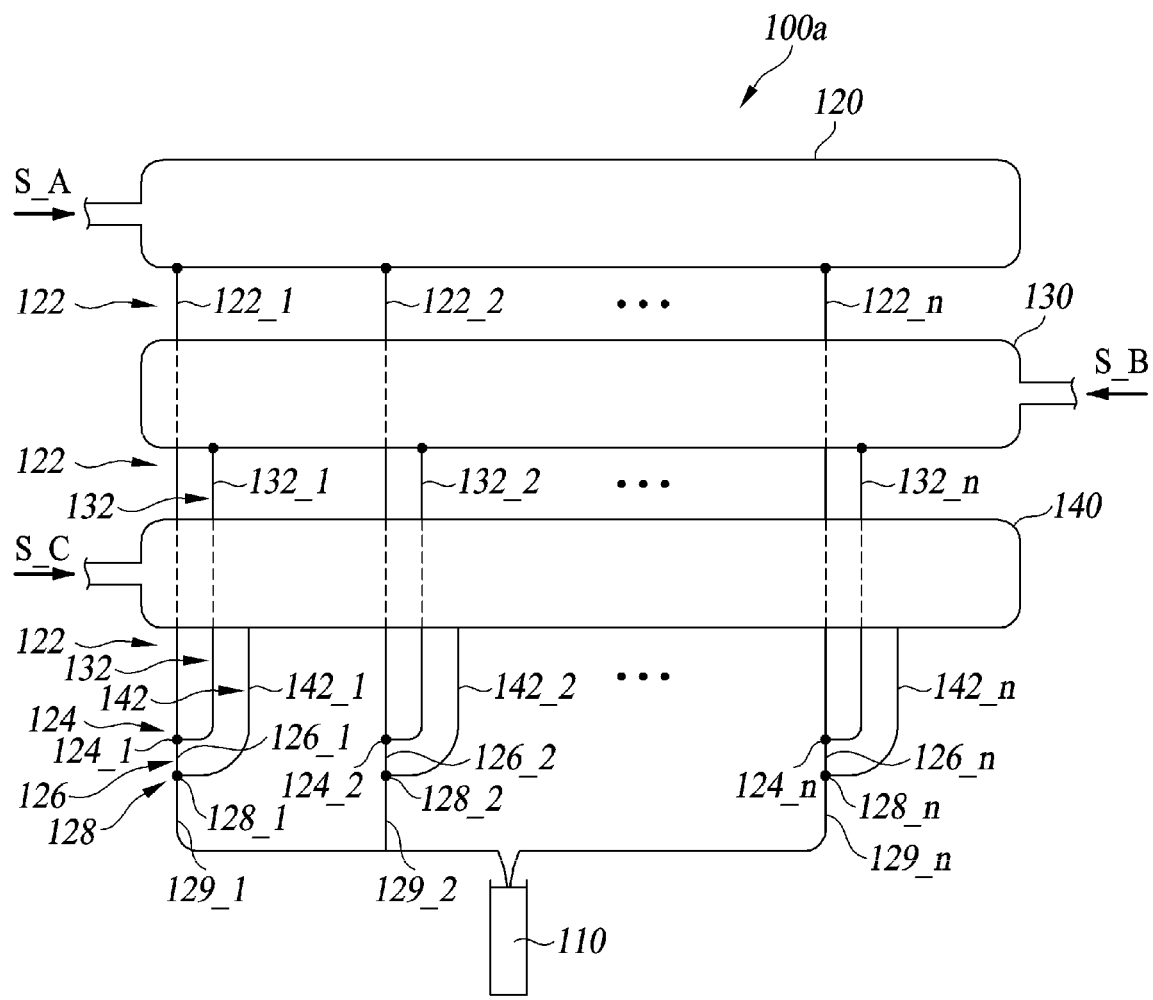
FIG. 34 is a block diagram illustrating a Channel-to-Channel Fluidic Connection Relationship of the Multichannel Microsphere Forming Unit of the Mass Production Apparatus according to another embodiment of the present invention.

FIG. 34 is Block diagram illustrating a Channel-to-Channel Fluidic Connection Relationship of the Multichannel Microsphere Forming Unit of the Mass Production Apparatus according to another embodiment of the present invention.

Referring to FIG. 34, the multichannel microsphere forming unit 100a of the mass production apparatus according to another embodiment of the present invention comprises a first inlet manifold 120, a second inlet manifold, a third inlet manifold, a plurality of first microchannels, a plurality of second microchannels, a plurality of third microchannels, a plurality of fourth microchannels and a plurality of fifth microchannels.

The first inlet manifold 120 is in fluid communication with the first material outlet 320 of the first material reservoir 300 and receives the first raw material delivered from the first material reservoir 300. The first inlet manifold 120 is also in fluid communication with the plurality of first microchannels 122;122_1-122_$n$ and supplies the received first raw material to each of the first microchannels.

The second inlet manifold 130 is in fluid communication with the second material outlet 420 of the second material reservoir 400 and receives the second raw material S B delivered from the second material reservoir 400. The second inlet manifold 130 is also in fluid communication with the plurality of second microchannels 132;132_1-132_$n$ and supplies the received second raw material to each of the second microchannels. The second inlet manifold 130 is not directly connected to the plurality of first microchannels 122;122_1-122_$n$. In FIG. 34, the plurality of first microchannels 122;122_1-122_$n$ which pass under the second inlet manifold 130 are depicted with dotted lines in FIG. 34.

The third inlet manifold 140 is in fluid communication with the third material outlet of the third material reservoir 600 and receives the third raw material S_C delivered from the third material reservoir 600. The third inlet manifold 140 is also in fluid communication with the plurality of fourth microchannels 142;142_1-142_$n$ and supplies the received third raw material to each of the fourth microchannels. The third inlet manifold 140 is not directly connected to the plurality of first and second microchannels 122;122_1-122_$n$ 132;132_1-132_$n$. In FIG. 34, the plurality of first and second microchannels 122;122_1-122_$n$ 132;132_1-132_$n$ which pass under the third inlet manifold 140 are depicted with dotted lines in FIG. 34.

Each of the first microchannels 122;122_1-122_$n$ and each of the second microchannels 132;132_1-132_$n$ join each other at the plurality of first merging points 124;124_1-124_$n$. The plurality of third microchannels 126;126_1-126_$n$ are joined to the plurality of first merging points 124;124_1-124_$n$, respectively. In addition, the plurality of third microchannels 126;126_1-126_$n$ extend from the plurality of first merging points 124;124_1-124_$n$ to the plurality of second merging points 128;128_1-128_$n$. The plurality of third microchannels 126;126_1-126_$n$ and the plurality of fourth microchannels 142;142_1-142_$n$ merge with each other at the plurality of second merging points

128;128_1-128_n. The core microspheres MS1 are formed at the the plurality of the first merging points as a consequence of the first raw material flowing in the first microchannels merging with the second raw material flowing in the plurality of the second microchannels and flow through the plurality of third microchannels. The multi-layered microspheres MS2 are formed at the plurality of second merging points 128;128_1-128_n as a consequence of the core microspheres flowing in the plurality of third microchannels merging with the third raw material flowing in the plurality of fourth microchannels at the plurality of second merging points 128;128_1-128_n. The multi-layered microspheres thus formed, i.e., MS2, then flow through the plurality of fifth microchannels 129:129_1-129_n to be collected at the product outlet 110.

In another embodiment of the present invention, the first inlet manifold 120, the second inlet manifold 130, and the third inlet manifold 140 are provided with a relatively large volume compared to the size of and the flow rate in the plurality of first microchannels n122;122_1-122_n, the plurality of second microchannels 132;132_1-132_n and the plurality of fourth microchannels 142;142_1-142_n. More specifically, in another embodiment of the present invention, each of the first inlet manifold 120, the second inlet manifold 130 and the third inlet manifold 140 specifically has a volume sufficiently large enough to provide substantially the same flow rate to the plurality of first microchannels 122; 122_1-122_n, the plurality of second microchannels 132; 132_1-132_n and the plurality of fourth microchannels 142;142_1-142_n, respectively.

Thus, in another embodiment of the present invention, the plurality of first microchannels 122;122_1-122_n, the plurality of second microchannels 132;132_1-132_n, or the plurality of fourth microchannels 142;142_1-142_n have substantially uniform and constant pressure and flow rate in the respective microchannels.

Figure 35:
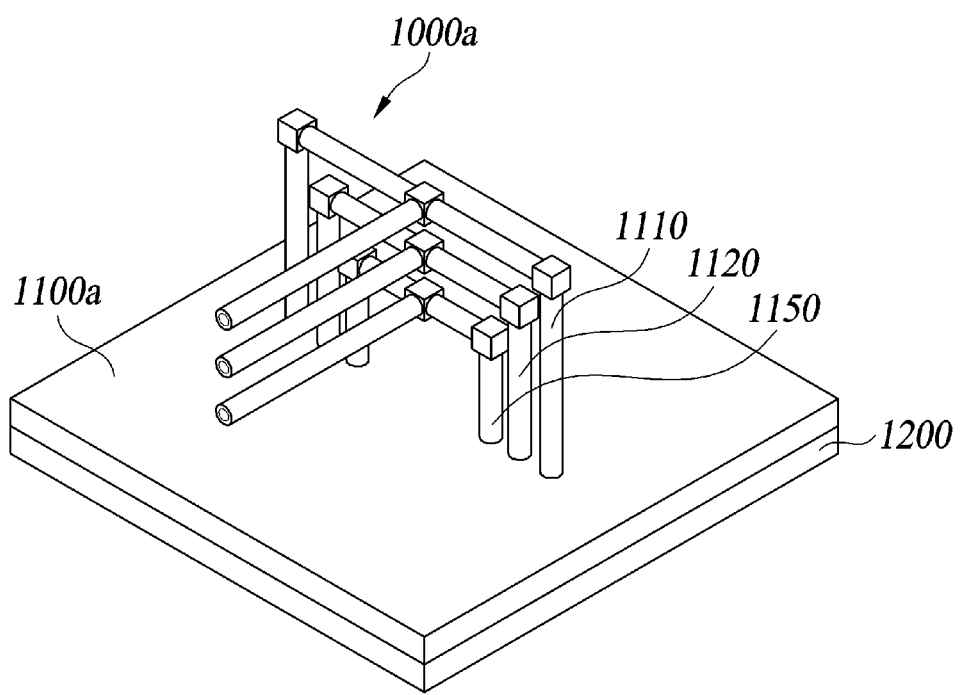
FIG. 35 is an assembled perspective view of the Multichannel Microsphere Forming Unit according to another embodiment of the present invention.
Figure 36:
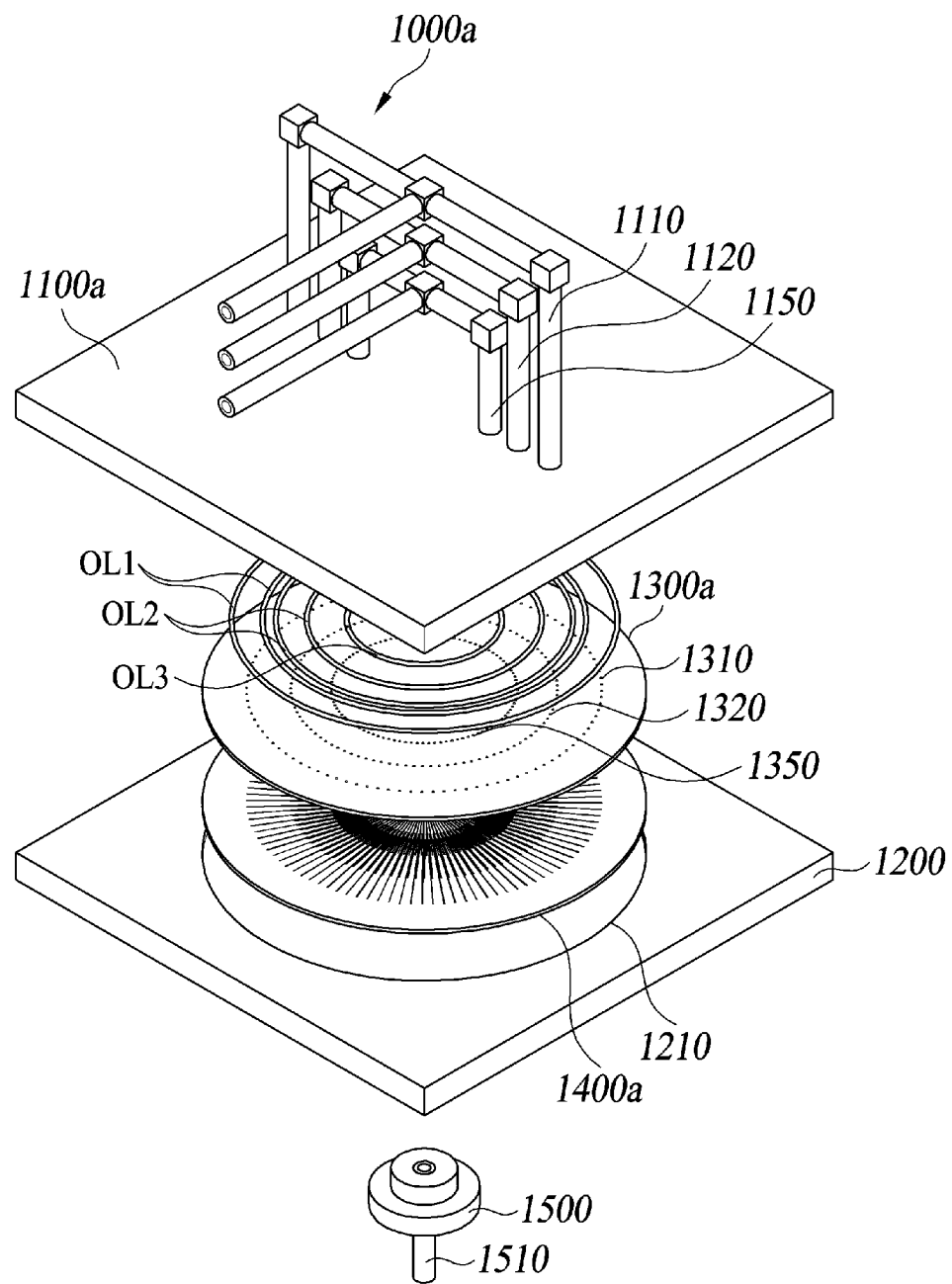
FIG. 36 is an exploded perspective view of the Multichannel Microsphere Forming Unit of FIG. 35.
Figure 37:
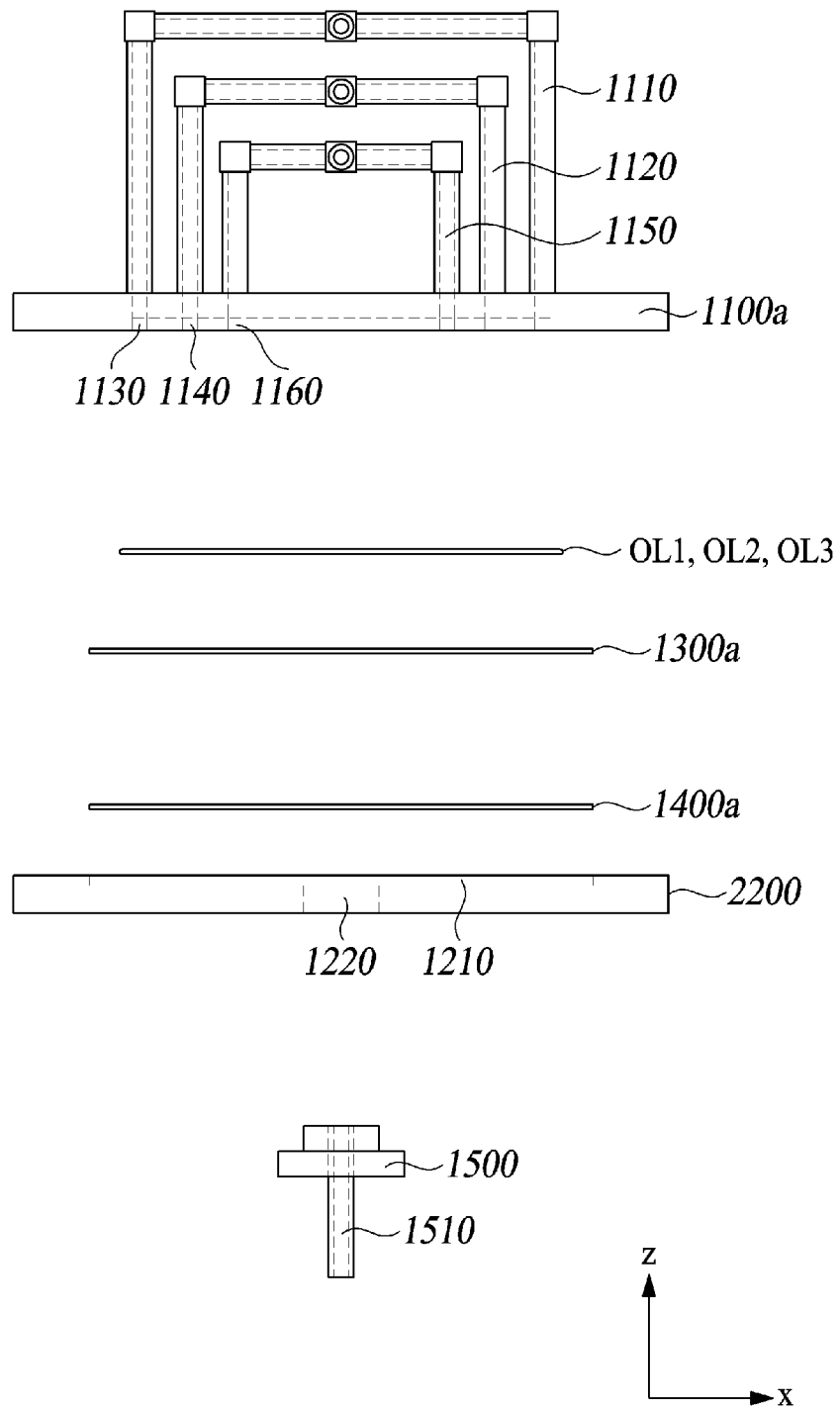
FIG. 37 is an exploded perspective view of the Multichannel Microsphere Forming Unit of FIG. 35.

There are shown in FIG. 35 to FIG. 38 an assembled perspective view of the multichannel microsphere forming unit according to another embodiment of the present invention, an exploded perspective view of the multichannel microsphere forming unit of FIG. 35, an exploded perspective front view of the multichannel microsphere forming unit of FIG. 35 and a bottom view of the upper case of FIG. 35, respectively.

Referring FIGS. 35 to 38, the multichannel microsphere forming unit 1000a of the mass production apparatus according to another embodiment of the present invention comprises an upper case 1100a, a lower case 1200, a plurality of O-rings OL1, OL2, OL3, an upper multichannel plate 1300a, a lower multichannel plate 1400a, and a product exhausting port 1500.

In another embodiment of the present invention, the upper case 1100a comprises a first inlet pipe 1110, a second inlet pipe 1120, a third inlet pipe 1150, a first annular manifold 1130, a second annular manifold 1140, and a third annular manifold 1160. The first inlet pipe 1110, the second inlet pipe 1120, and the third inlet pipe 1150 are disposed on the upper surface of the upper case 1100a. The first annular manifold 1130, the second annular manifold 1140, and the third annular manifold 1160 are formed on the lower surface of the upper case 1100a.

The first inlet pipe 1110 is in fluid connection with the first material outlet 320 of the first material reservoir 300 and the other end is in fluid connection with the first annular manifold 1130 passing through the upper case 1100a. The first raw material is supplied from the outside of the multichannel forming unit 100 through the first inlet pipe 1110 and is delivered to the first annular manifold 1130 at the lower surface of the upper case 1100a.

The second inlet pipe 1120 is in fluid connection with the second material outlet 420 of the second material reservoir 400, and the other end is in fluid connection with the second annular manifold 1140 passing through the upper case 1100a. The second raw material is supplied from the outside of the multichannel forming unit through the second inlet pipe 1120 and is delivered to the second annular manifold 1140 at the lower surface of the upper case 1100a.

The third inlet pipe 1150 is in fluid connection with the third material outlet of the third material reservoir 600, and the other end is in fluid connection with the third annular manifold 1160 passing through the upper case 1100a. The third raw material is supplied from the outside of the multichannel microsphere forming unit 1000a through the third inlet pipe 1150 and is delivered to the third annular manifold 1160 at the lower surface of the upper case 1100a.

Figure 38:
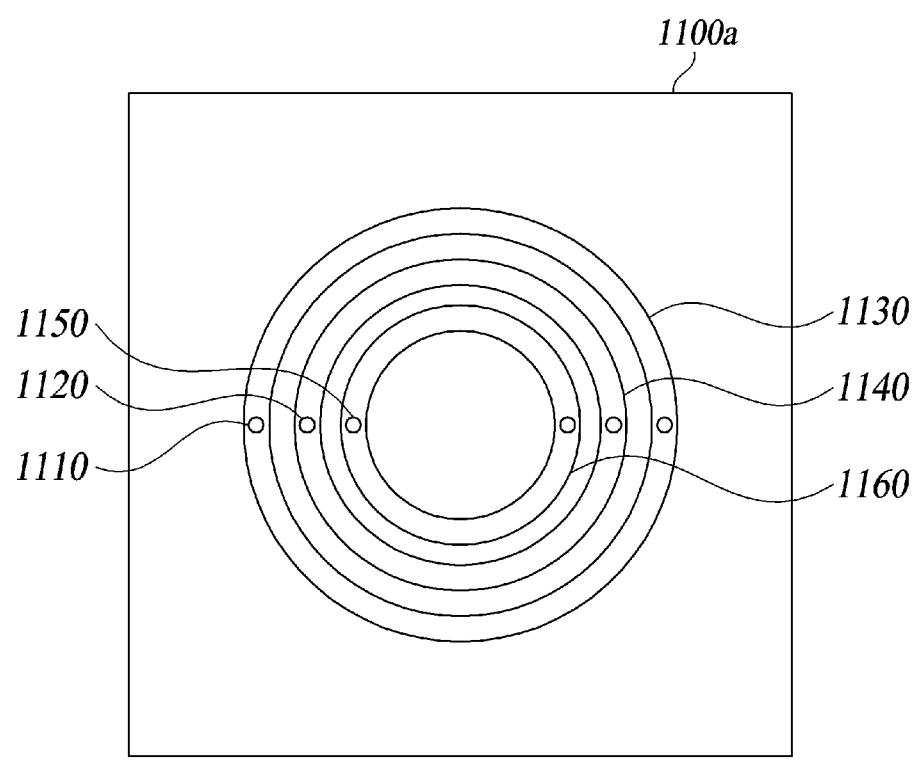
FIG. 38 is a bottom view of the Upper Case of the Multichannel Microsphere Forming Unit of FIG. 35.

In FIG. 38, it is depicted that although the first inlet pipe 1110, the second inlet pipe 1120 and the third inlet pipe 1150 are branched at an upper portion of the upper case 1100a so that two lines are respectively connected to the first annular manifold 1130, the second annular manifold 1140 or the third annular manifold 1160, the present invention is not limited thereto. In other embodiments, the first inlet pipe 1110, the second inlet pipe 1120, and the third inlet pipe 1150 may not be branched or branched into three or more lines to form a connection to the first annular manifold 1130, the second annular manifold 1140 or the third annular manifold 1160.

The first annular manifold 1130, the second annular manifold 1140 and the third annular manifold 1160 are annular recesses formed on the bottom surface of the upper case 1100a. The first annular manifold 1130 is disposed radially outward of the second annular manifold 1140 and the second annular manifold 1140 is disposed radially outward of the third annular manifold 1160. In the illustrated embodiment, the radial cross-sections of the first annular manifold 1130, the second annular manifold 1140, and the third annular manifold 1160 are shown as being substantially the same. However, the present invention is not limited thereto. For example, the size of the radial cross-sections or the width of the channels may be different with each other so that the first annular manifold 1130, the second annular manifold 1140, and the third annular manifold 1160 have the same or comparably close sized volume.

The upper case 1100a is disposed on the upper portion of the upper multichannel plate 1300a, and a plurality of O-rings OL1, OL2, OL3 are disposed between the upper case 1100a and the upper multichannel plate 1300a. The plurality of O-rings OL1, OL2, OL3 comprise a first O-ring OL1 radially disposed inwardly or outwardly adjacent to the first annular manifold 1130, a second O-ring OL2 radially disposed inwardly or outwardly adjacent to the second annular manifold 1140 and a third O-ring OL3 radially disposed inwardly or outwardly adjacent to the third annular manifold 1160. The plurality of O-rings OL1, OL2, OL3 prevent the leakage of fluids including the first raw material, the second raw material or the third raw material inside the first annular manifold 1130, the second annular manifold 1140 or the third annular manifold 1160 along the interface between the upper case 1100a and the upper multichannel plate 1300a. In the illustrated embodiment of the present invention, a pair of first O-rings OL1, a pair of second O-rings OL2, and a third O-ring OL3 are depicted. However, the present invention is not limited thereto, for the number of O-rings OL1, OL2, OL3 can be increased or decreased as long as an appropriate sealing can be assured therewith.

Figure 39:
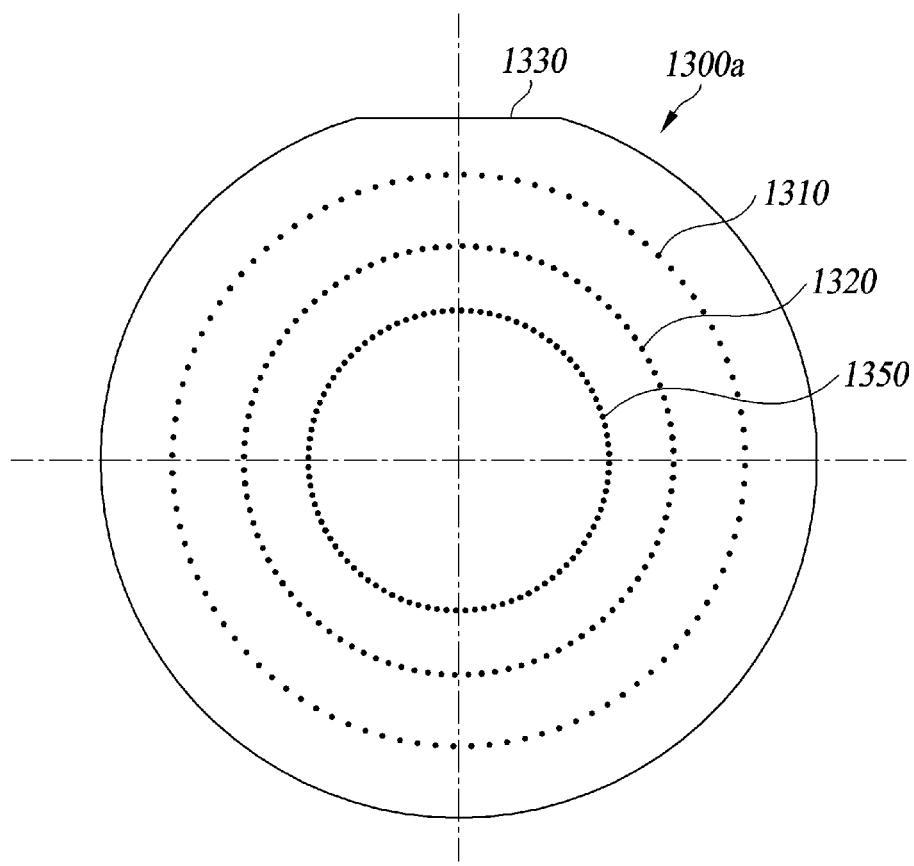
FIG. 39 is a top view of the Upper Multichannel Plate of the Multichannel Microsphere Forming Unit according to another embodiment of the present invention.

FIG. 39 is a top view of an upper multichannel plate of the multichannel microsphere forming unit according to another embodiment of the present invention.

Referring to FIG. 39, the upper multichannel plate 1300a includes a plurality of first channel connection holes 1310, a plurality of second channel connection holes 1320, a plurality of third channel connection holes 1350 and a plate alignment portion 1330 for the upper plate.

The plurality of first channel connection holes 1310 are disposed along a first circle having a first diameter. The plurality of second channel connection holes 1320 are disposed along a second circle having a second diameter smaller than the first diameter. The plurality of third channel connection holes 1350 are disposed along a third circle having a third diameter smaller than the second diameter. In an embodiment of the present invention, the plurality of first channel connection holes 1310 are disposed radially outward of the plurality of second channel connection holes 1320, and the plurality of second channel connection holes 1320 are disposed radially outward of the third channel connection holes 1350. Further, the plurality of first channel connection holes 1310, the plurality of second channel connection holes 1320 and the plurality of third channel connection holes 1350 are disposed of coaxially.

The outer shape and size of the upper multichannel plate 1300a correspond to the outer shape and size of the plate seating groove 1210 of the lower case to be mounted. In an embodiment of the present invention, the plate alignment portion of the upper multichannel plate are fitted to the case alignment portion of the lower case.

Figure 40:
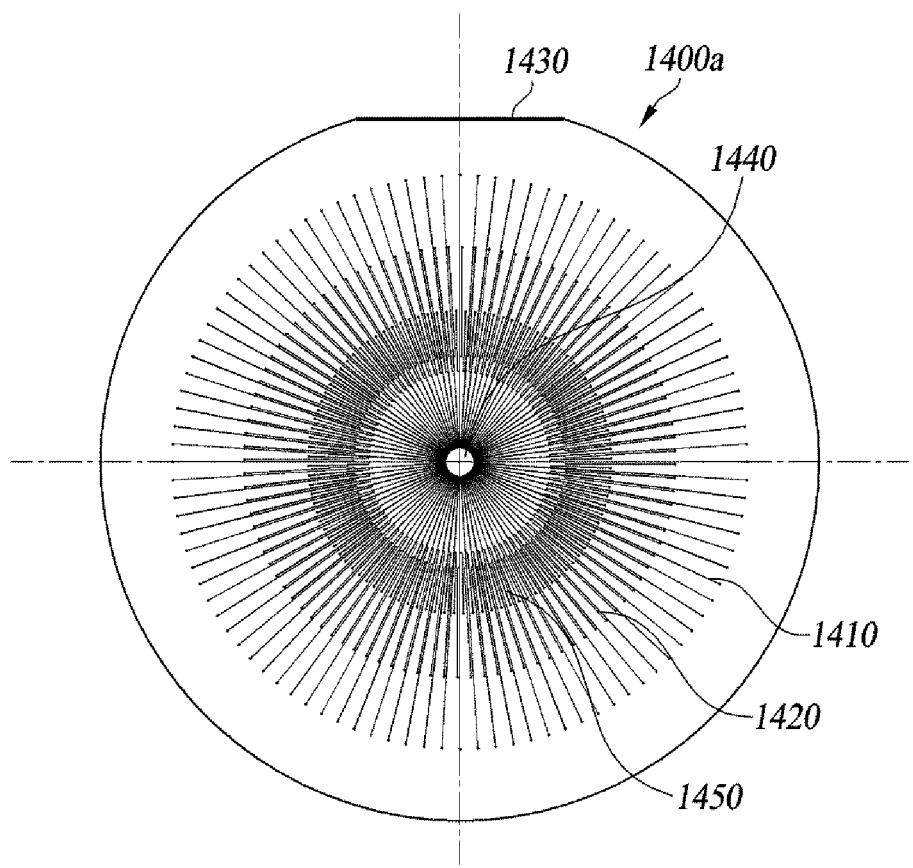
FIG. 40 is a top view showing the Upper Multichannel Plate overlapped with the Lower Multichannel Plate of the Multichannel Microsphere Forming Unit according to another embodiment of the present invention.
Figure 41:
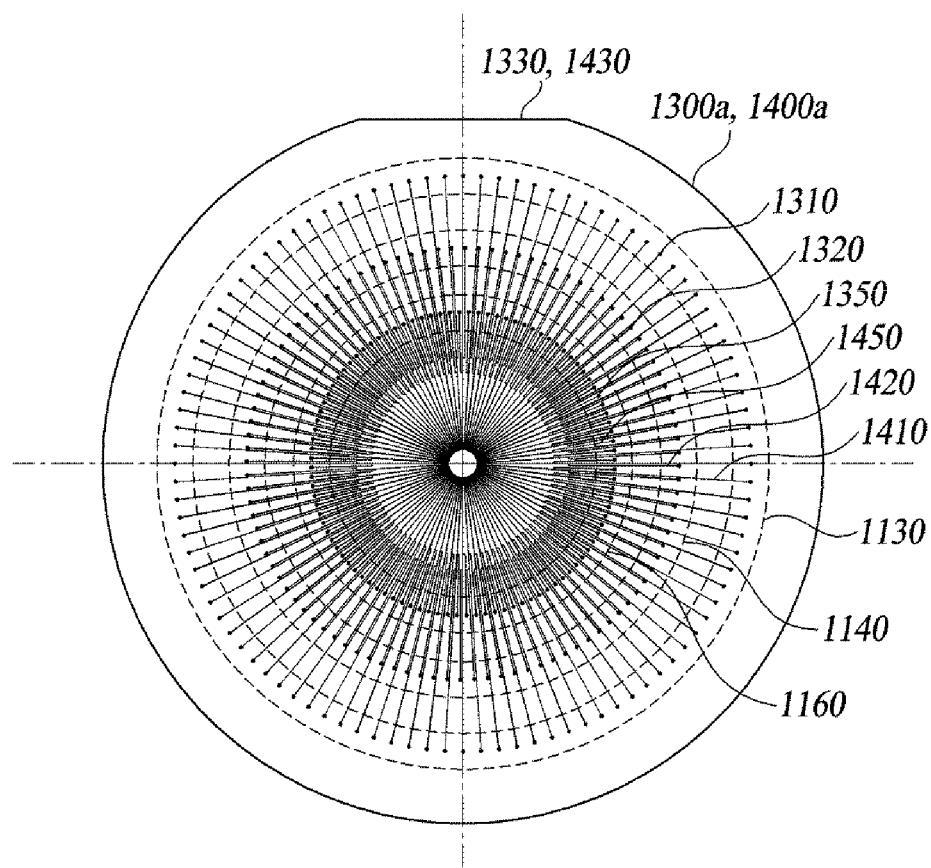
FIG. 41 is a top surface translucent diagram showing FIG. 40 with the First Annular Manifold, the Second Annular Manifold and the Third Annular Manifold of the Upper Case in hidden lines.

There are shown in FIGS. 40 and 41 a top view showing the upper multichannel plate overlapped with the lower multichannel plate of the multichannel microsphere forming unit 1000a according to an embodiment of the present invention and a top surface translucent diagram showing FIG. 40 with the first annular manifold, the second annular manifold and the third annular manifold of the upper case in hidden lines, respectively.

Referring to FIGS. 40 and 41, the lower multichannel plate 1400a comprises a plurality of first microchannels 1410, a plurality of second microchannels 1420, a plurality of third microchannels 1412, a plurality of fourth microchannels 1450, a plurality of fifth microchannels 1416 and a center through-hole 1440. The lower multichannel plate 1400a is disposed between the upper multichannel plate 1300a and the lower case 1200.

The plurality of first microchannels 1410, the plurality of second microchannels 1420, the plurality of third microchannels 1412, the plurality of fourth microchannels 1450 and the plurality of fifth microchannels 1416 have a trench structure formed on the upper surface of the lower multichannel plate 1400a.

The plurality of first microchannels 1410 are radially disposed on the upper surface of the upper multichannel plate 1300a. Each of the first microchannels 1410 is disposed radially from the center through-hole 1440. The plurality of second microchannels 1420 are radially disposed in parallel with the first microchannels 1410. The plurality of first microchannels 1410 and the plurality of second microchannels 1420 merge with one another at the first merging points 1414, respectively. The plurality of third microchannels 1412 are radially disposed inward of the plurality of first microchannels 1410. One end of each of the third microchannels 1412 is connected to the first merging point 1414, and the other end thereof is connected to the second merging point 1418. The plurality of third microchannels 1412 and the plurality of fourth microchannels 1450 are merged at the second merging point 1418. The plurality of fifth microchannels 1416 are radially disposed inward of the plurality of third microchannels 1412. One end of the plurality of fifth microchannels 1416 is connected to the second merging point 1418 and the other end, to the center through-hole 1440.

The outer shape and size of the lower multichannel plate 1400a correspond to the outer shape and size of the plate seating groove 1210 of the lower case 1200 to be mounted. In an embodiment of the present invention, the plate alignment portion of the lower multichannel plate 1440a is fitted to the case alignment portion 1230 of the lower case 1200.

The plurality of first channel connection holes 1310 of the upper multichannel plate 1300a are disposed on the plurality of first microchannels 1410. In addition, the plurality of second channel connection holes 1320 of the upper multichannel plate 1300a are disposed on the plurality of second microchannels 1420 and the plurality of third channel connection holes 1350 of the upper multichannel plate 1300a are disposed on the plurality of fourth microchannels 142; 142_1-142_n.

The plurality of first microchannels 1410 are respectively in fluid connection with the first annular manifold 1130 through the plurality of first channel connection holes 1310, the plurality of second microchannels 1420, respectively in fluid connection with the second annular manifold 1140 through the plurality of second channel connection holes 1320, and the plurality of fourth microchannels 1450, respectively in fluid connection with the third annular manifold 1160 through the fourth channel connection holes 1350.

Figure 42:
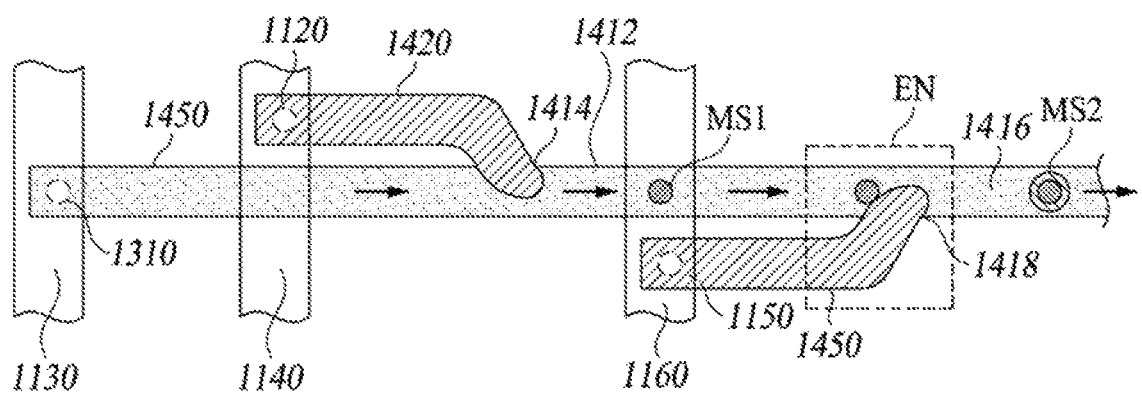
FIG. 42 is an exemplary schematic view showing the formation of the Multi-layered Microsphere MS2 in the Mass Production Apparatus according to another embodiment of the present invention.

FIG. 42 is an exemplary schematic view showing a process for the forming of the multi-layered microspheres MS2 in the mass production apparatus according to another embodiment of the present invention.

In FIG. 42, the microsphere forming path is shown in an enlarged form, each configurations being exaggerated in size, enlarged or reduced, for convenience of explanation.

In another embodiment of the present invention, the first annular manifold 1130 is connected to the first microchannel through the first channel connection hole 1310. The first annular manifold 1130 supplies the first raw material, for example, water-phase solution in which PVA, a surfactant, being dissolved in pure water, to the first microchannel 1410. The second annular manifold 1140 is connected to the second microchannel 1420 through the second channel connection hole 1320. The second annular manifold 1140 contains the second raw material, for example, PCL-dissolved oil-phase solution, wherein PCL is a biodegradable polymer. At the first merging point 1414, the second raw material having a hydrophobic surface is introduced from the second microchannel 1420 into the first raw material having a hydrophillic surface, resulting in a formation of droplets comprising the second raw material, flowing into the third microchannel 1412. As the amount of the second raw material introduced at the first merging point 1414 increases, the flow pressure of the first raw material acting on the second introduced raw material correspondingly increases, resulting in, at the first merging point 1414, the second raw material separating from the second microchannel 1420 and flow in a droplet form along with the first raw material having a relatively large flow rate in the third microchannel 1412. An isotropic external force acts on the droplets of the hydrophobic second raw material in the hydrophillic first raw material, making it possible for the droplets of the second raw material to maintain a spherical shape. The droplets thus formed harden with time as they flow in the third microchannels, resulting in the formation of the desired microspheres, ie. the core microspheres, i.e., MS1.

The third annular manifold 1160 is connected to the fourth microchannel 1450 through the third microchannel connection hole 1350. The third annular manifold 1160 may contain a third raw material, for example, an oily solution in which PGA, a biodegradable material, is dissolved in an oil. At the second merging point, the third raw material having a hydrophobic surface is introduced from the fourth microchannel into the first raw material having a hydrophilic surface, including therein the core microspheres, MS1, flowing in the third microchannels 1412. When the core microspheres, i.e., MS1, come in contact with the introduced third raw material at the second merging point 1418, the hydrophobic third raw material wets the core microspheres MS1 having a hydrophobic surface. As the flow pressure acting on the core microspheres MS1 and the introduced third raw material increases, the core microspheres MS1 and the introduced third raw material will be separated from the other third raw material in the fourth microchannel 1450. An isotropic external force acting on the hydrophobic third raw material in the hydrophilic first raw material spread the third raw material evenly around the core microspheres MS1, resulting in the formation of multi-layered microspheres MS2 and the multi-layered MS2 thus formed flow in the fifth microchannels 1416.

Figure 43A:
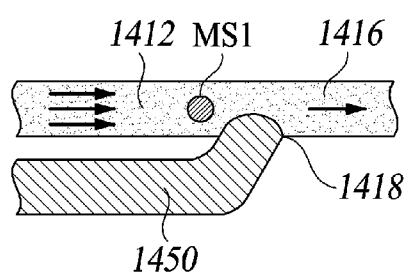
FIGS. 43A to 43C illustrate forming of the multi-layered microsphere MS2 as a consequence of MS1 coming in contact with the Third Material at the Second Merging Point in accordance with another embodiment of the present invention.
Figure 43B:
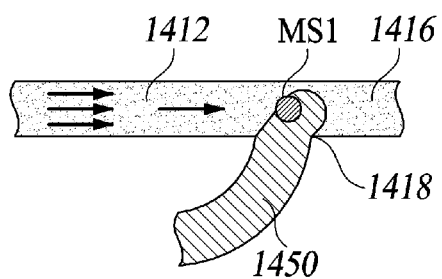
Figure 43C:
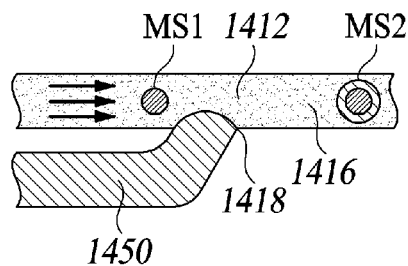
Figure 44A:
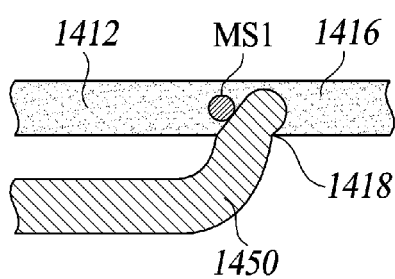
FIGS. 44A to 44C illustrate forming of the multi-layered microsphere MS2 as a consequence of MS1 coming in contact with the Third Material introduced relatively in large quantity at the Second Merging Point in accordance with yet another embodiment of the present invention.
Figure 44B:
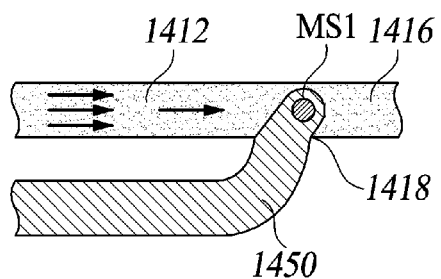
Figure 44C:
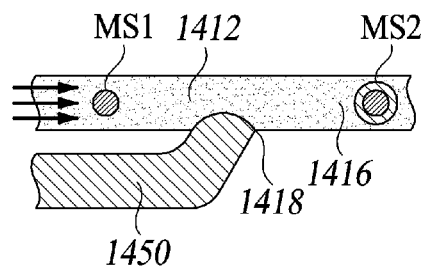

There are illustrated in FIGS. 43(*a*) to 43(*c*) the forming of a multi-layered microsphere MS2 as a consequence of MS1 coming in contact with the third raw material at the second merging point in accordance with another embodiment of the present invention and in FIGS. 44(*a*) to (*c*), the forming of a multi-layered microsphere as a consequence of the core microsphere coming in contact with the third raw material introduced in a relatively large quantity at a second merging point of the device according to yet another embodiment of the present invention.

Referring to FIGS. 43(*a*) and 44(*a*), at the second merging point 1418 where the core microsphere MS1 and the introduced third raw material come into contact, the extent to which the third raw material is introduced may be different. In FIG. 43(*a*), the third raw material introduced is shown to be being relatively small, and in FIG. 44(*a*), the opposite, i.e., relatively larger amount than shown in FIG. 43(*a*).

The thickness of the surrounding layer of the third raw material constituting the multi-layered microspheres MS2 depends on the amount of the third raw material introduced and then separated at the second merging point.

As shown in FIGS. 43(*a*) to 43(*c*), when the core microspheres MS1 come in contact with the introduced third raw material at the second merging point 1418, the introduced third raw material (FIG. 43(*b*)) get attached itself to the hydrophobic core microsphere MS1 even if the amount of the third raw material introduced is relatively small (FIG. 43(*a*)), and MS1 with the third raw material attached thereto separate from the second merging point 1418 to form the multi-layered microspheres MS2 (FIG. 43(*c*)) when the flow pressures of the first raw material acting thereon become sufficiently large.

In contrast, as shown in FIGS. 44(*a*) to 44(*c*), when the third raw material in a relatively larger amount than the one shown in FIG. 43(*a*) comes in contact with the core microspheres MS1, the core microspheres MS1 remains attached to the third raw material for a relatively shorter period of time compared to the case shown in FIG. 43(*b*) before being separated from the second merging point 1418 to form the multi-layered microsphere MS2 (FIG. 44(*c*)) due to the flow pressure of the first raw material.

In the illustrated examples, the amount or thickness of the third raw material forming on the core microsphere MS1 to form the multi-layered microspheres MS2 depends on the amount of the third raw material introduced to and separated from the second merging point 1418. Further, it also depends on the flow resistance acting on the third raw material and the core microsphere MS1 at the moment of separation.

Thus, according to another embodiment of the present invention, if the dimensions and the flow rates of the channels can be kept constant, the size, the distribution and the layer thickness of the multi-layered microspheres MS2 can be also made constant, independent of the amount of the third raw material.

As described above, as a consequence of the present invention capable of providing, controlling and maintaining a constant flow rate within the plurality of microchannels, it is possible to generate the multi-layered microspheres using therewith of a desired shape, size and dispersion.

Figure 45:
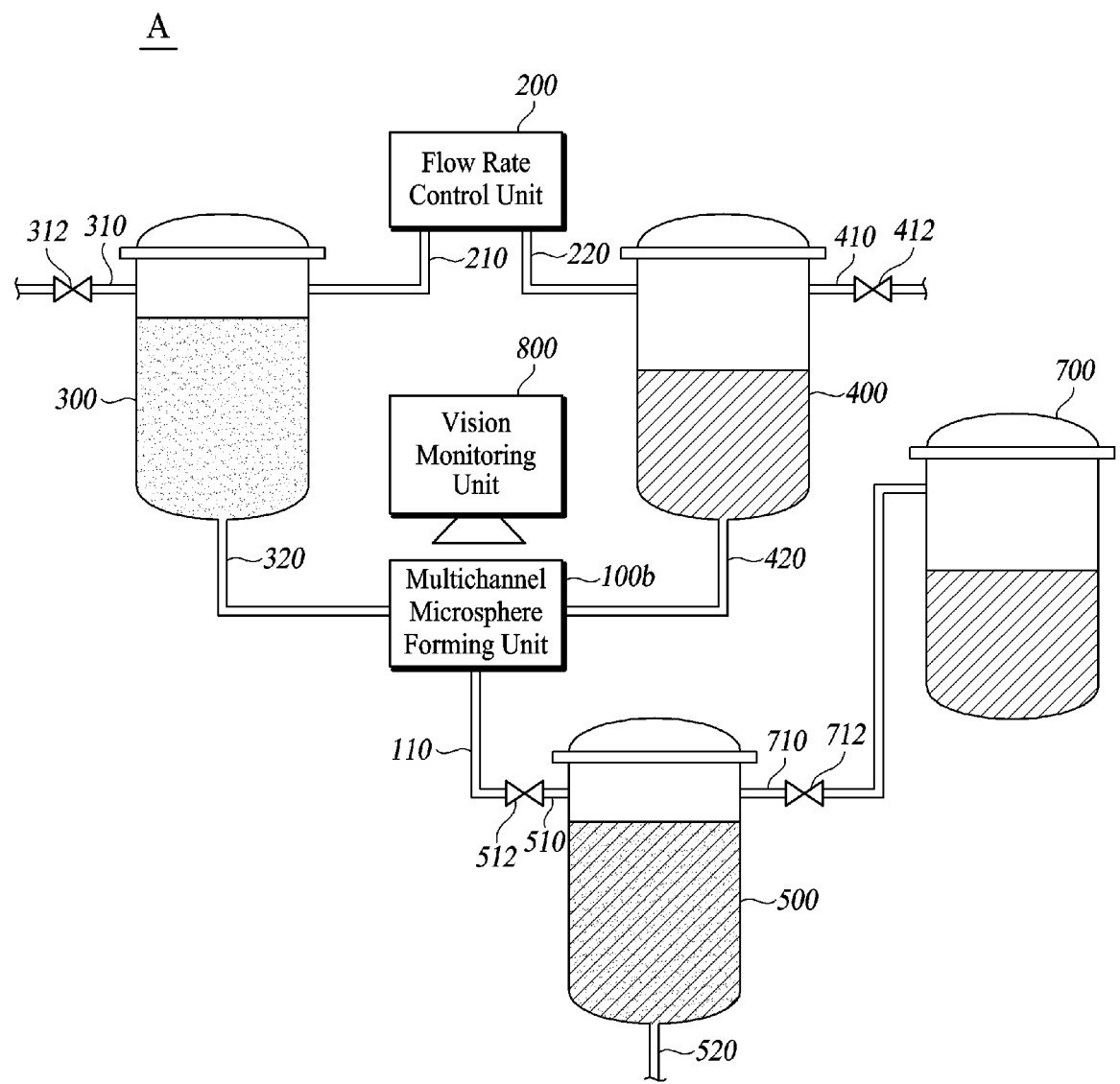
FIG. 45 is a block diagram of the Mass Production Apparatus according to yet another embodiment of the present invention.

FIG. 45 is a block diagram of the mass production apparatus for microspheres according to another embodiment of the present invention.

There is shown in FIG. 45, a mass production apparatus according to another embodiment of the present invention incorporating therein a vision monitoring unit 800 as compared with the embodiment of the present invention shown in FIG. 14.

The vision monitoring unit 800 for is disposed on at least one side of the multichannel microsphere forming unit 100*b*. The vision monitoring unit 800 comprises a camera, for example, a CCD camera, which observes the state of microsphere formation in the multichannel microsphere forming unit 100*b* in real time. The vision monitoring unit 800 transmits the visual information/data to an operator viewing unit (not shown). The operator viewing unit may further comprise, for example, a display for displaying the photographed images. The operator may analyze the image/data obtained by and through the vision monitoring unit 800 and control the operation of the entire apparatus accordingly based thereon.

However, the present invention is not limited thereto. In some embodiments, the visual information obtained by the vision monitoring unit 800 may be analyzed in real time using an automatic analyzing apparatus, and the apparatus may be automatically controlled or an alarm may be sent to the operator according to the analyzed results.

Figure 46:
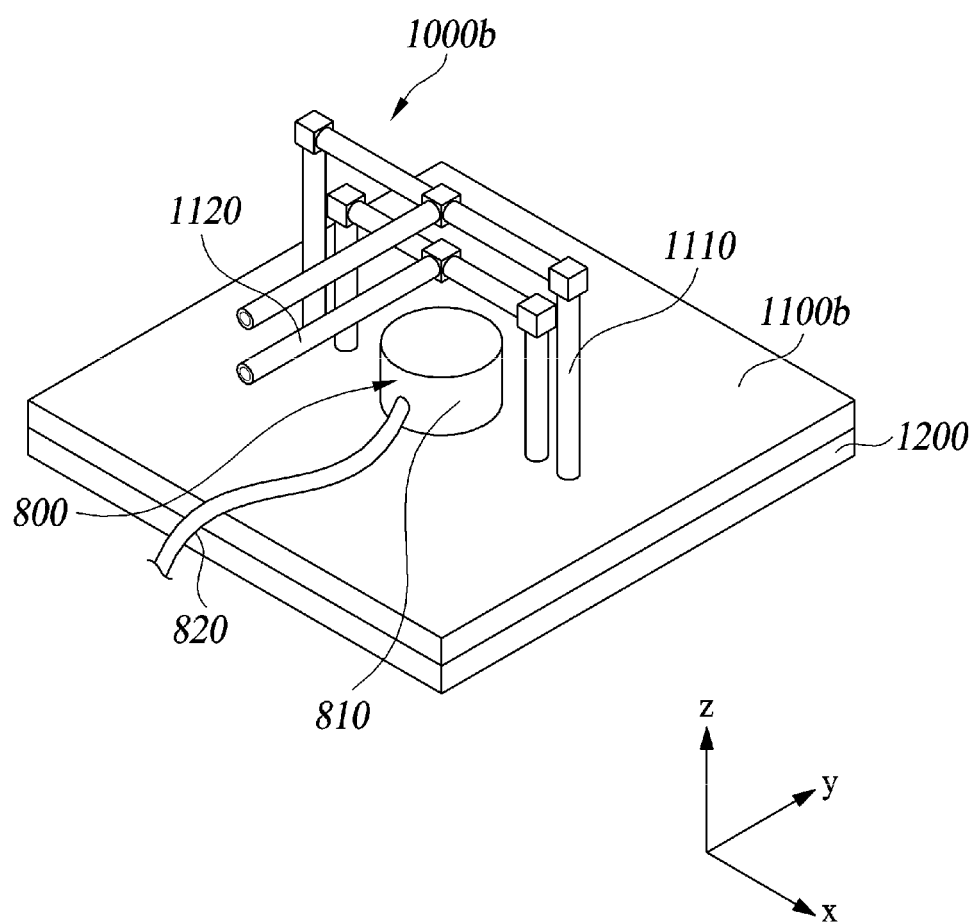
FIG. 46 is an assembled perspective view of the Multichannel Microsphere Forming Unit of the Mass Production Apparatus in accordance with yet another embodiment of the present invention.

There are shown in FIGS. 46 to 50 an assembled perspective view of the multichannel microsphere forming unit of the mass production apparatus according to another embodiment of the present invention, an exploded perspective view of the multichannel microsphere forming unit of FIG. 46, an exploded perspective front view of the multichannel microsphere forming unit of FIG. 46, an assembled perspective front view of the multichannel microsphere forming unit of FIG. 46 and a bottom view of the upper case of FIG. 46, respectively.

Figure 47:
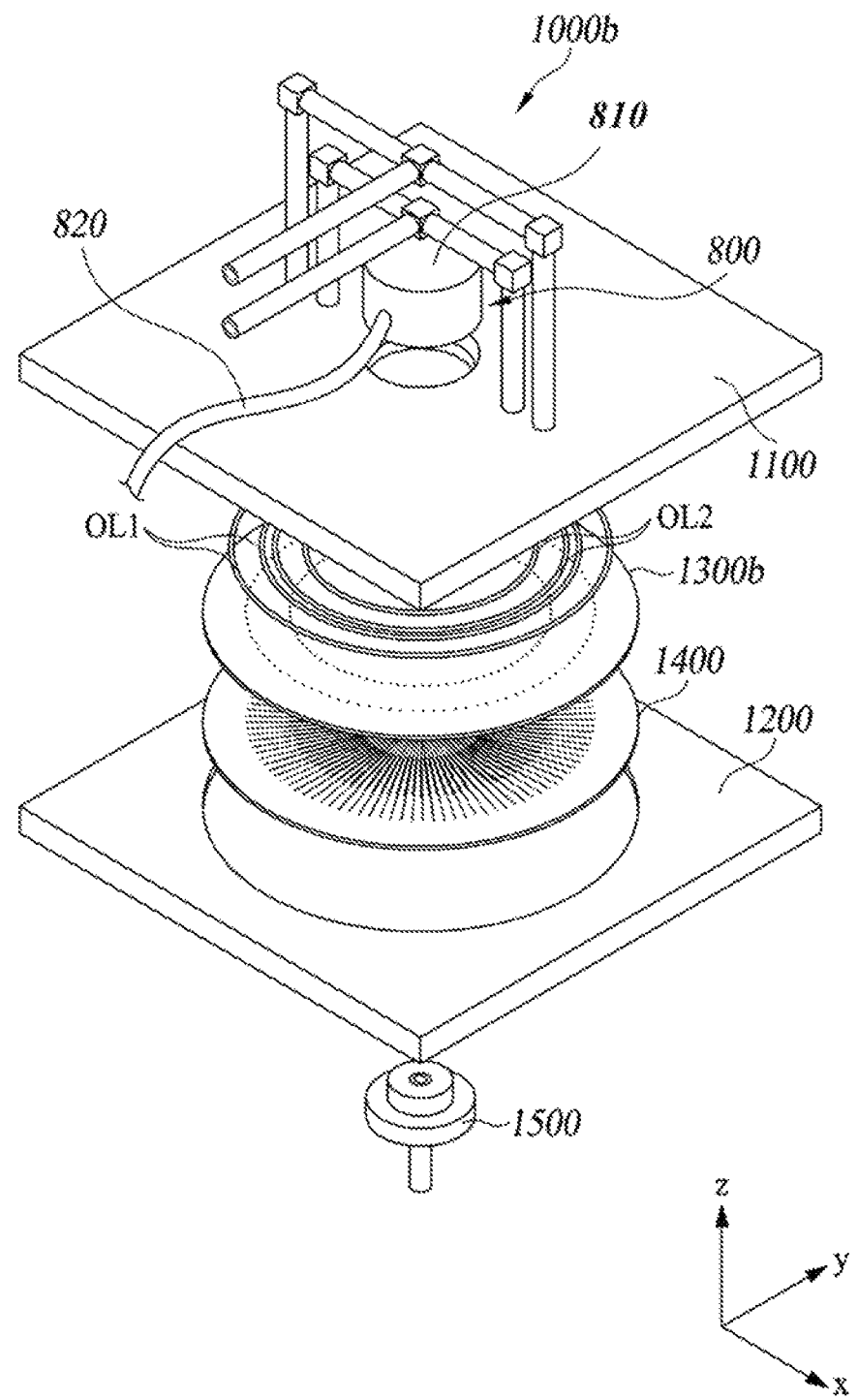
FIG. 47 is an exploded perspective view of the Multichannel Microsphere Forming Unit shown in FIG. 46.
Figure 48:
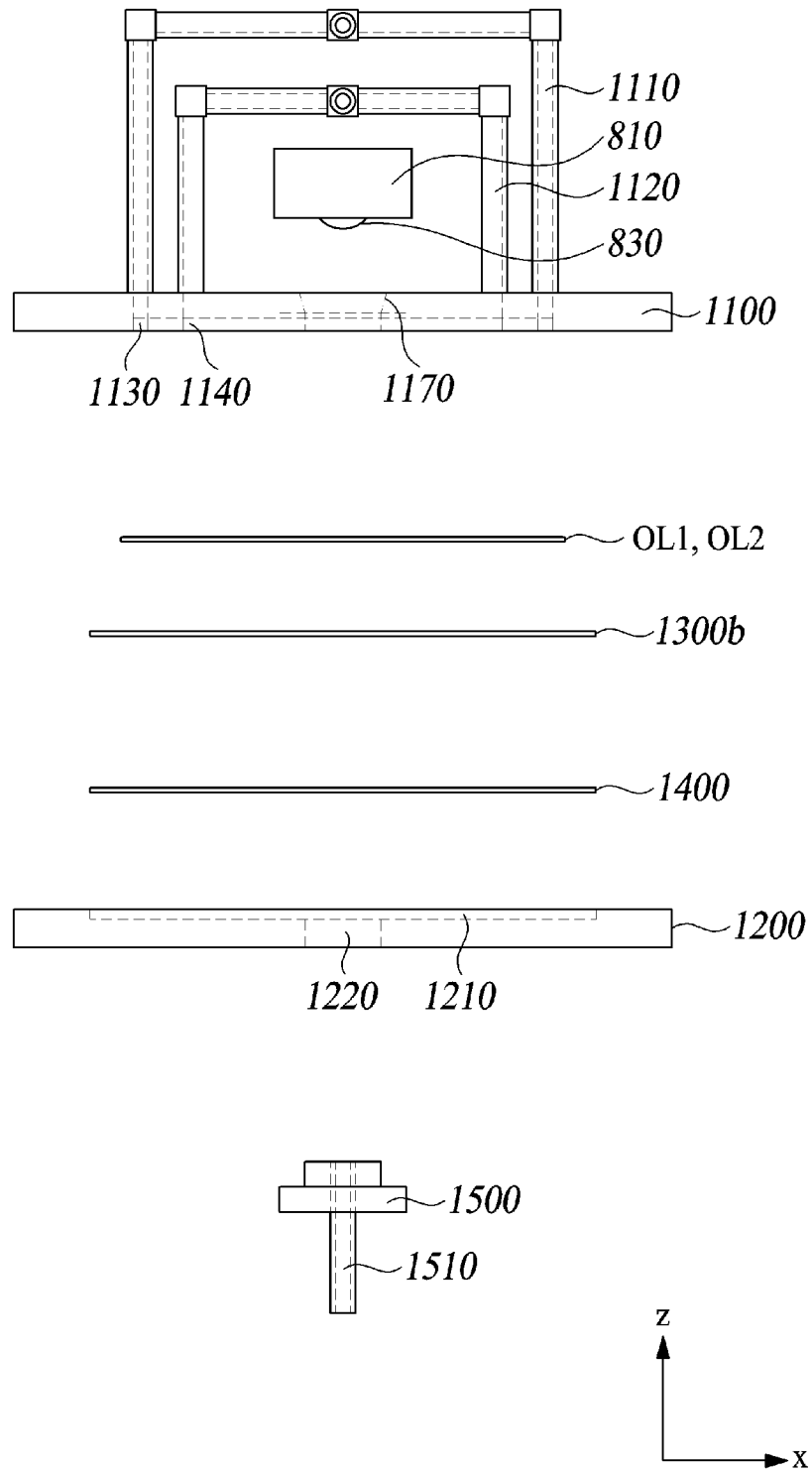
FIG. 48 is an exploded perspective front view of the Multichannel Microsphere Forming Unit shown in FIG. 46.
Figure 49:
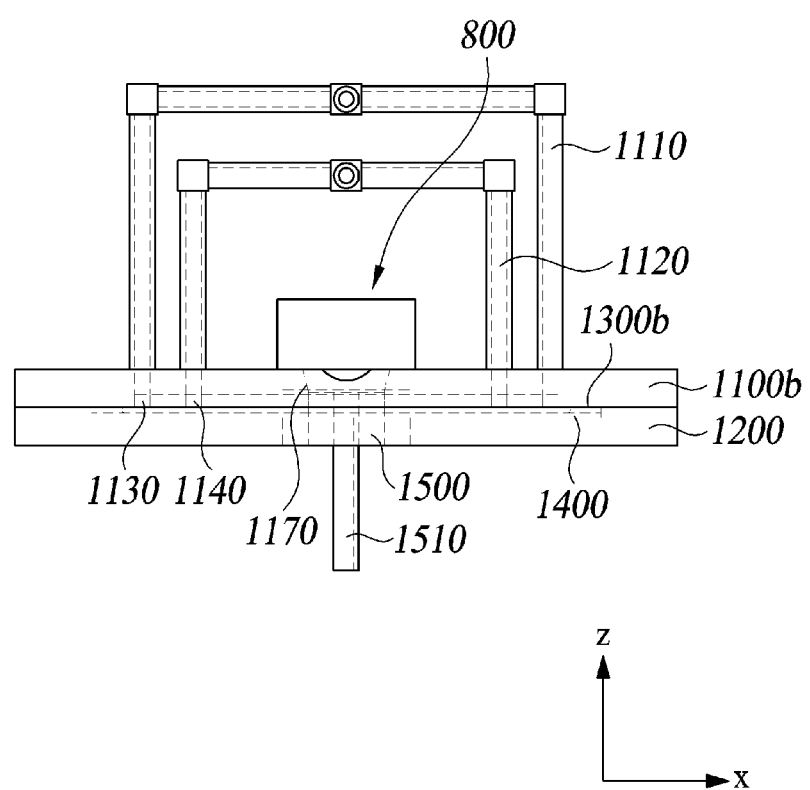
FIG. 49 is an assembled perspective view of the Multichannel Microsphere Forming Unit shown in FIG. 46.
Figure 50:
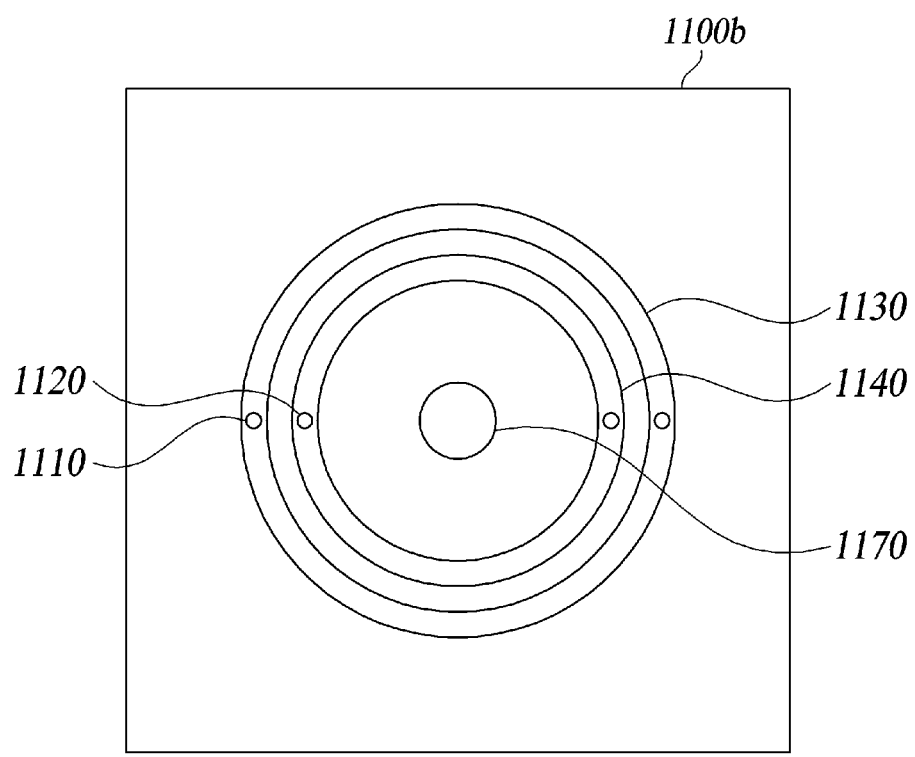
FIG. 50 is a bottom view of the Upper Case shown in FIG. 46.

Referring FIGS. 46 to 48, the multichannel forming unit 1000*b* of the mass production apparatus according to another embodiment of the present invention comprises an upper case 1100*b*, a lower case 1200, a plurality of O-rings OL1, OL2, an upper multichannel plate 1300*b*, a lower multichannel plate 1400, a product exhausting port 1500 and a vision monitoring unit 800.

In another embodiment of the present invention, the upper case 1100*b* comprises a first inlet pipe 1110, a second inlet pipe 1120, a first annular manifold 1130, a second annular manifold 1140 and a monitoring opening 1170. The monitoring opening 1170 is disposed at the center of the upper case 1100b. The monitoring opening 1170 may also be formed through the upper case 1100b.

The monitoring opening 1170 is of sufficient size to observe the microchannels in the central region of the lower multichannel plate 1400a, the diameter thereof being larger than the size of the product-exhausting hole 1220.

In another embodiment of the present invention, the upper multichannel plate 1300b is made of a transparent or translucent material. It is made of a material which is rigid and has a high dimensional accuracy, such as a silicon wafer, a glass wafer, a PDMS, or the like. In particular, in another embodiment of the present invention, the upper multichannel plate 1300b is made of a glass wafer. The plurality of first channel connection holes 1310 and the plurality of second channel connection holes 1320 are provided with a relatively simple structure so that they can be suitably formed of the glass having a higher toughness than a silicon wafer, allowing the observation of the microchannels formed in the lower multichannel plate 1400 through the monitoring opening 1170 and the upper multichannel plate 1300b possible.

The vision monitoring unit 800 comprise a camera body 810, a signal cable 820 and a viewing lens 830, the camera body 810 being attached to the monitoring opening 1170 on the upper surface of the upper case 1100a, wherein the camera body 810 is a camera, for example, a CCD camera and is used for observing the forming state of microspheres in real time.

The signal cable 820 is a signal transmission line for transmitting an image photographed by the camera body 810 to an external device. In some embodiments, the vision monitoring unit 800 may comprise a wireless communication unit (not shown) installed in the camera body 810, the wireless communication unit transmitting the visual information to an external monitoring device.

The viewing lens 830 is disposed below the camera body 810 wherein the viewing lens 830 is directed through the monitoring opening 1170 to the microchannels formed on the upper multichannel plate 1300b and the lower multichannel plate 1400.

Although not shown, the vision monitoring unit 800 may further comprise illumination unit. The illumination unit may be disposed adjacent to the viewing lens 830 and may provide reflected light that is reflected by the microchannels and is incident on the viewing lens 830.

Figure 51:
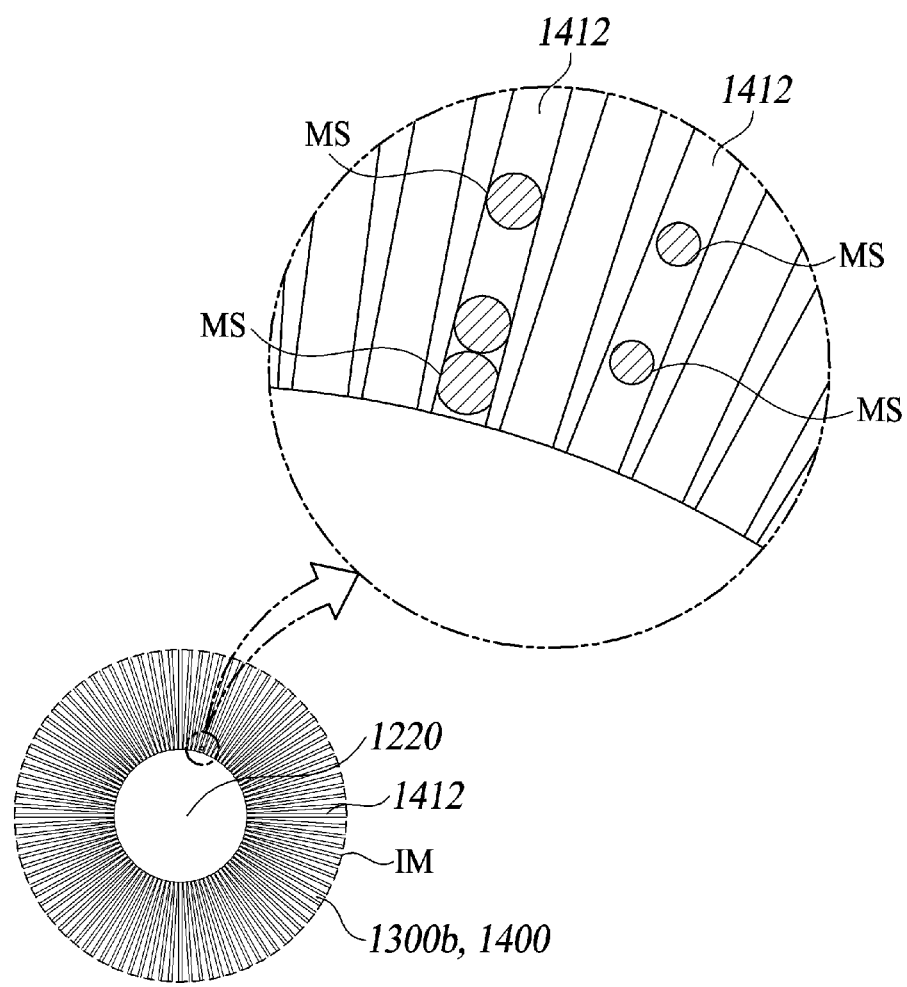
FIG. 51 is a photographed image of the Microchannels around the Product-exhausting Hole and an Enlarged exemplary partial view of the Microchannels.

FIG. 51 is a photographed image of the microchannels around the product-exhausting hole and an enlarged exemplary partial view of these channels.

Referring to FIG. 51, the vision monitoring unit 800 takes photographs of the microchannels disposed around the product exhausting port 1220. The shape, size, and size distribution of the microspheres formed in each microchannel can be identified through photographed images. In FIG. 51, some microchannels are shown enlarged. In this exemplary enlargement view, one microchannel is shown to be blocked by an abnormally large microsphere. If such microsphere clogs one channel, the total flow through that microchannel is expected to decrease. As the flow rate of the microchannel is reduced, the microspheres formed therein will have a different size than the target size, detrimentally affecting the microsphere size distribution in the overall product.

As the number of microchannels forming the oversized or undersized microspheres outside the target size increases, the size distribution of the microspheres in the final product will increase. This will not only degrade the quality of the entire product but will also increase the processing load in additional sieving.

According to another embodiment of the present invention, it is possible to monitor the microchannels as to whether or not the microspheres formed are abnormal in size. If the problematic microchannels exceed a certain critical ratio, the operator may perform actions such as wafer replacement, cleaning of the wafer or inspection of other related parts. Alternatively, the valve may be closed to block the flow at microchannels causing the problem. This is described below in detail as another embodiment of the present invention.

Figure 52:
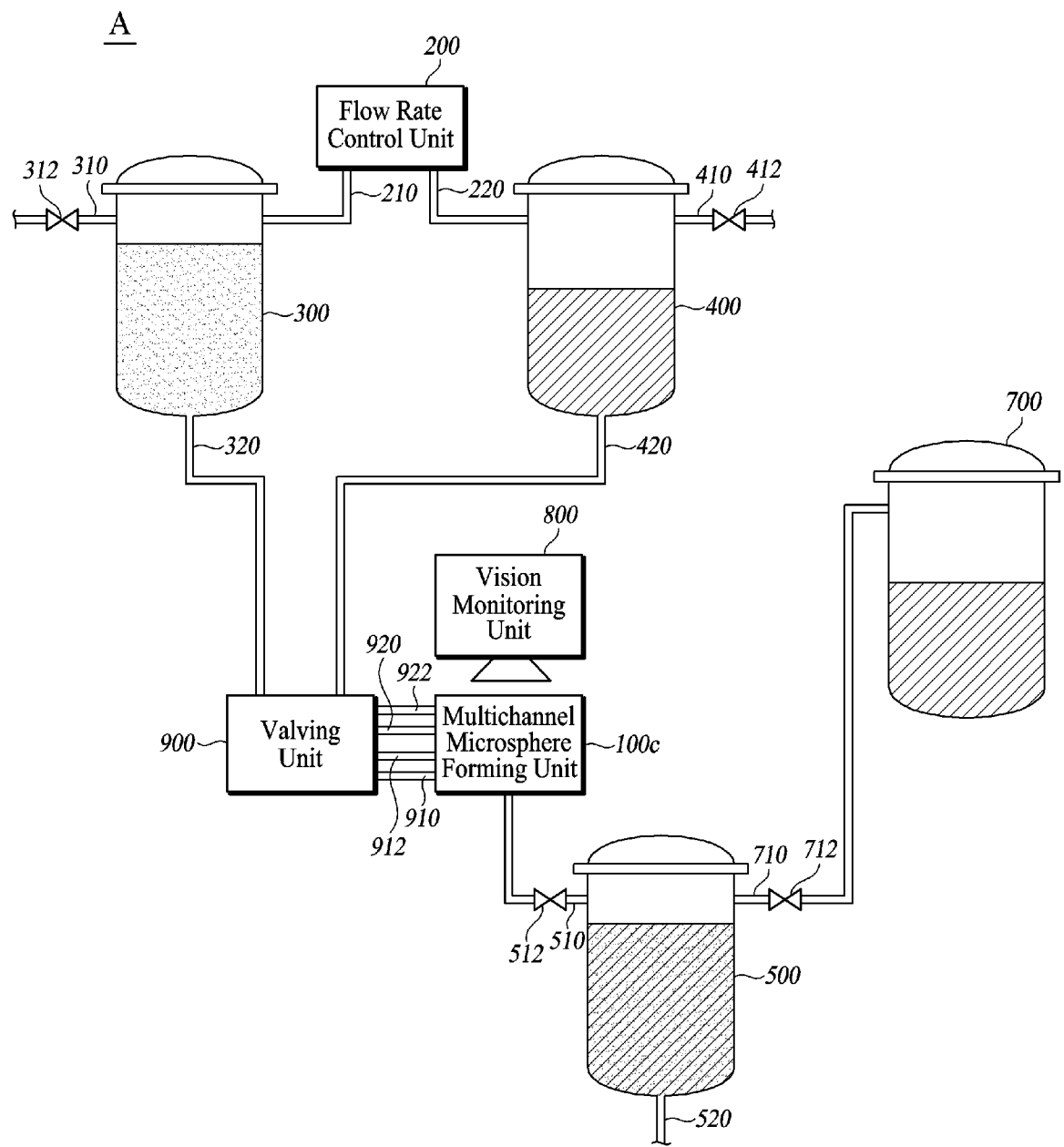
FIG. 52 is a lock diagram of the Mass Production apparatus incorporating therein a Channel-specific Valve Function according to yet another embodiment of the present invention.

FIG. 52 is a block diagram of the mass production apparatus including therein a channel-specific valving function according to still yet another embodiment of the present invention.

Referring to FIG. 52, the apparatus according to another embodiment of the present invention further comprises a valving portion 900 as compared to the embodiment shown in FIG. 45.

The valving portion 900 is connected to the first material outlet 320 of the first material reservoir 300 and the second material outlet 420 of the second material reservoir 400, respectively. The valving portion 900 receives the first raw material from the first material reservoir 300 and branch the supplied first raw material to the multichannel microsphere forming unit 100c through the plurality of first material transfer lines 910, 912. In addition, the valving portion 900 receive the second raw material from the second material reservoir 400 and branch the supplied second raw material to multichannel microsphere forming unit 100c through the plurality of second material transfer lines 920, 922.

The multichannel microsphere forming unit 100c comprises the microchannels connected to the respective transmission lines. If one of the transmission lines is closed or opened in the valving portion 900, the flow of the material to the microchannel connected thereto is also closed or opened.

That is, when it is determined that the microspheres formed in the specific microchannels are not of the desired quality according to the monitoring result of the vision monitoring unit 800, the supplies to the corresponding microchannels may be cut off using the valving portion 900 by the operator or the automatic analyzing apparatus, stopping the formation of the problematic microspheres in the related microchannels.

Figure 53:
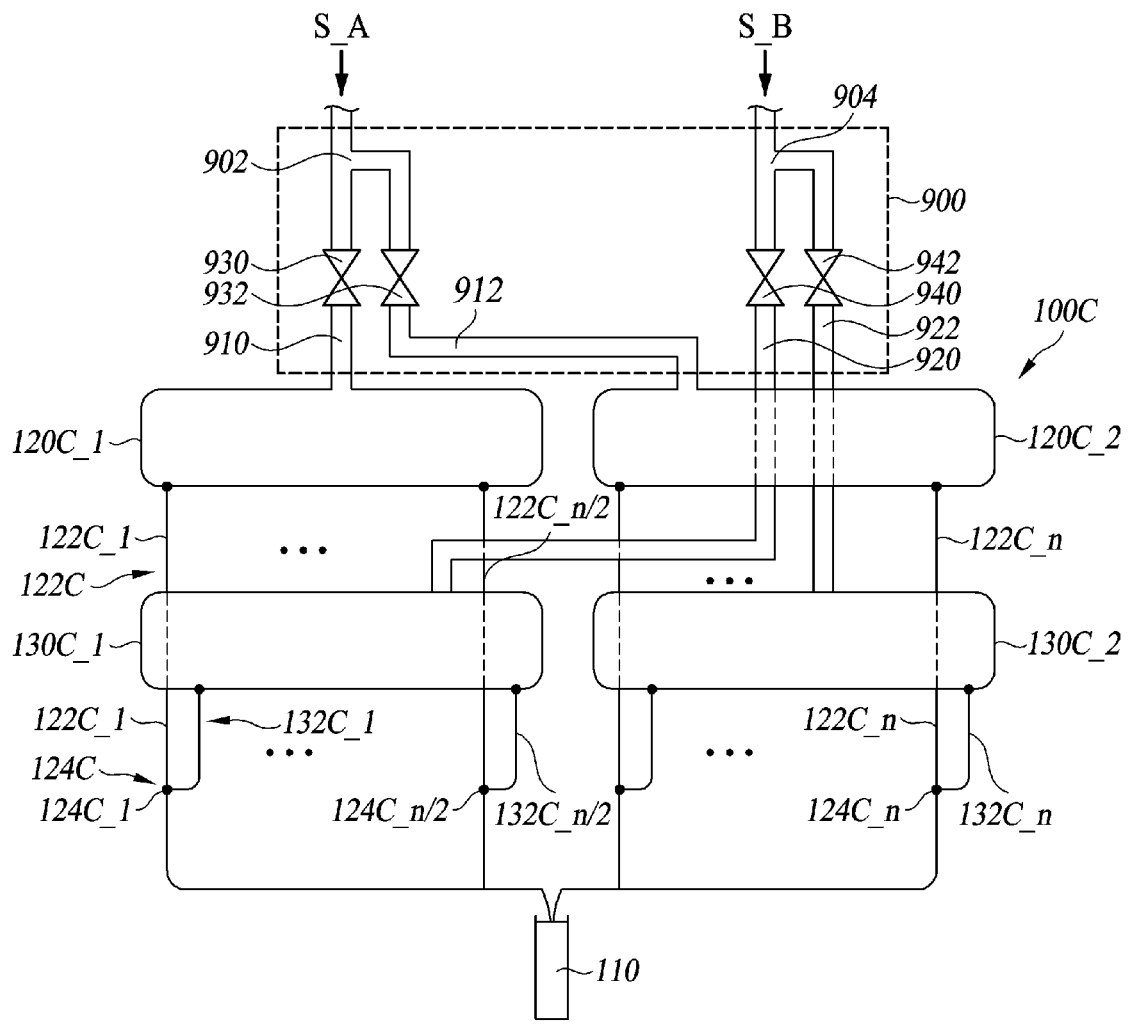
FIG. 53 is an exemplary block diagram showing a Channel-to-Channel Fluidic Connection Relationship of the Valve Portion and the Multichannel Microsphere Forming Unit shown in FIG. 52 in accordance with yet another embodiment of the present invention.

FIG. 53 is an exemplarily block diagram showing the channel-to-channel fluidic connection relationship of the valving portion and the multichannel microsphere forming unit in the embodiment shown in FIG. 52.

Referring to FIG. 53, the valving portion 900 comprises a plurality of first material transfer lines 910, 912, a branching unit 902 for branching the supplied first raw materials and transferring them to the plurality of first material transfer lines 910, 912, and a plurality of first material valves 930, 932 connected in series to each of the plurality of first material transfer lines 910, 912.

In addition, the valving portion 900 further comprise a plurality of second material transfer lines 920, 922, a branch unit for branching the supplied second raw materials and transferring them to the plurality of second material transfer lines 920, 922 and a plurality of second material valves 940, 942 connected in series to each of the plurality of second material transfer lines 920, 922.

In the illustrated embodiment, the valving portion 900 is illustrated as branching one feed line to two feed lines.

However, the number of material transfer lines to be branched is only exemplary. In some embodiments, the valving portion 900 may branch a single feed line to three or more delivery lines.

The multichannel microsphere forming unit 100c may comprise a plurality of first inlet manifold 120C_1, 120C_2 and a plurality of second inlet manifold 130C_1, 130C_2. In the illustrated embodiment, the plurality of first inlet manifold 120C_1, 120C_2 and the plurality of second inlet manifold 130C_1, 130C_2 are shown as being two, respectively. However, the present invention is not limited thereto. The number of manifolds constituting the first inlet manifold and the second inlet manifold may be varied corresponding to the number of the material transfer lines branched and connected at the valving portion 900.

One of the plurality of first inlet manifolds 120C_1 is in fluid communication with one of the first transfer lines 910 and others of the plurality of first inlet manifolds 120C_2 are in fluid communication with the respective others of the first material transfer lines 912.

One of the plurality of first inlet manifolds 120C_1 is connected to a n/2 number of the first microchannels 122C_1-122C_n/2 and the other one of the plurality of first inlet manifolds 120C_2 is also connected to a n/2 number of the respective first microchannels 122C_n/2+1-122C_n.

Similarly, one of the plurality of second inlet manifolds 130C_1 is in fluid connection with a second material transfer line 920 and the others of the plurality of second inlet manifolds 130C_2 are in fluid connection with the respective others of the second material transfer line 922.

One of the plurality of second inlet manifolds 130C_1 is connected to a n/2 number of second microchannels 132C_1-132C_n/2, and the other one of the plurality of second inlet manifolds 130C_2 is similarly connected to a n/2 number of other respective second microchannels 132C_n/2+1-132C_n.

Each first microchannel and each second microchannel are merged at a plurality of merging points 124C;124C_1-124C_n. The plurality of third microchannels 126C; 126C_1-126C_n are connected to the plurality of merging points 124X;124C_1-124C_n, respectively. The plurality of third microchannels 126C;126C_1-126C_n extend from the plurality of merging points 124C;124C_1-124C_n to the product outlet 110.

Figure 54:
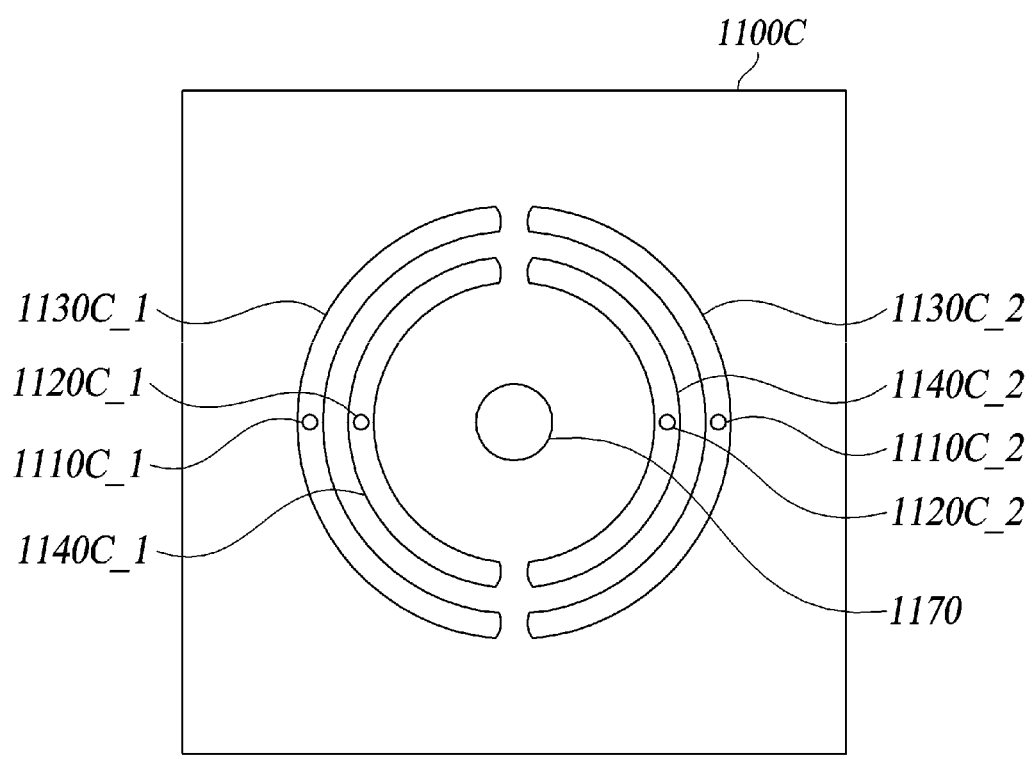
FIG. 54 is a bottom view of the Upper Case for implementing the Multichannel Microsphere Forming Unit shown in FIG. 53 according to yet another embodiment of the present invention.

There is shown in FIG. 54 a bottom view of an upper case for implementing a multichannel microsphere forming unit according to the embodiment shown in FIG. 53.

Referring to FIG. 54, the upper case 1100C comprises a plurality of first inlet manifolds 1130C_1, 1130C_2 and a plurality of second inlet manifolds 1140C_1, 1140C_2 formed on a lower surface thereof.

The plurality of first inlet manifolds 1130C_1, 1130C_2 are connected to the plurality of first inlet pipes 1110C_1, 1110C_2, respectively. The plurality of second inlet manifolds 1140C_1, 1140C_2 are connected to the plurality of second inlet pipes 1120C_1, 1120C_2, respectively. The plurality of first inlet manifolds 1130C_1, 1130C_2 and the plurality of second inlet manifolds 1140C_1, 1140C_2 are of semicircular trench structure formed on the lower surface of the upper case 1100C.

Figure 55:
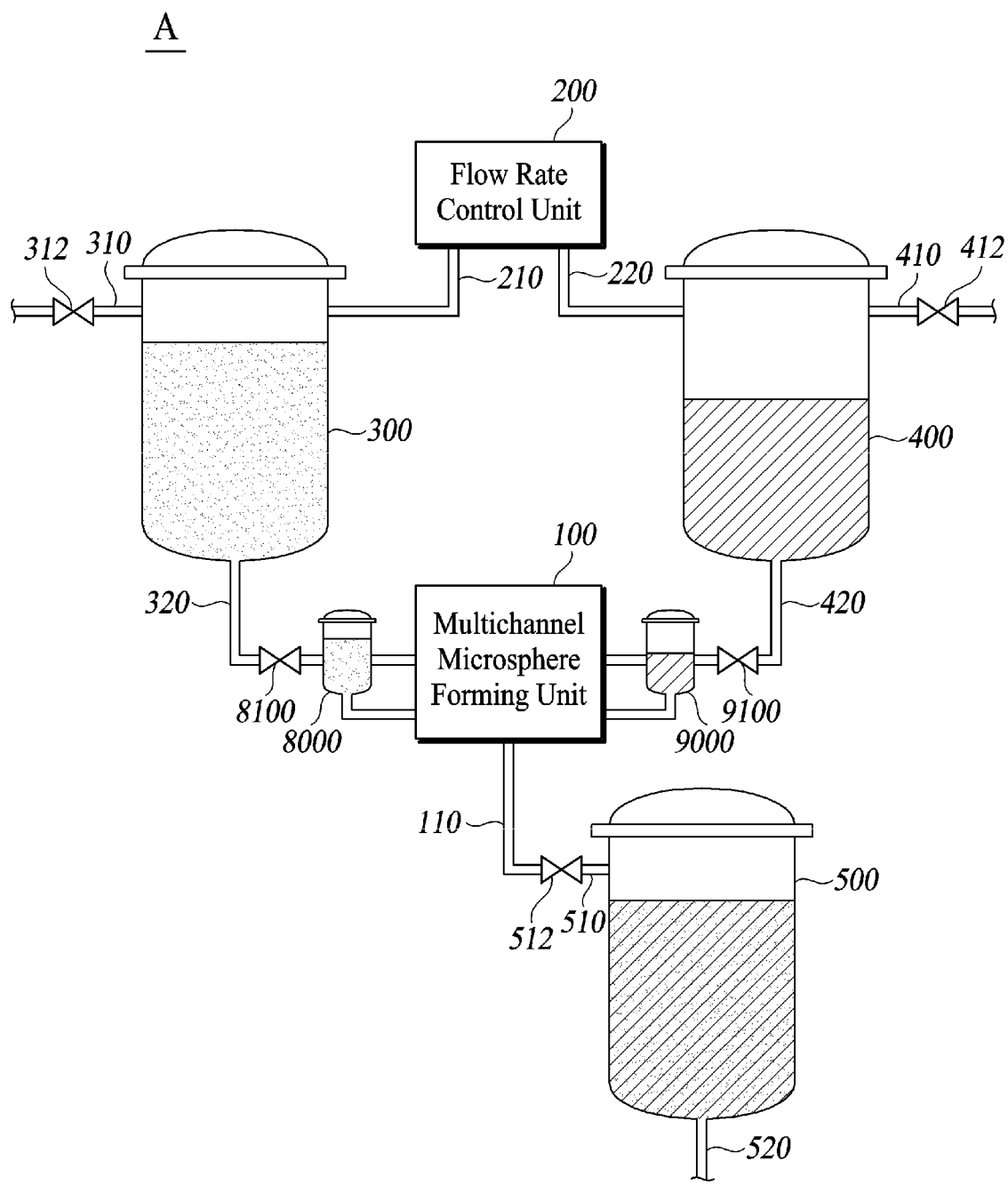
FIG. 55 is a block diagram of the Mass Production Apparatus incorporating therein a Buffer Tank according to still yet another embodiment of the present invention.

FIG. 55 is a block diagram of the mass production apparatus incorporating therein a buff tank according to still another embodiment of the present invention.

Referring to FIG. 55, the apparatus according to another embodiment of the present invention further includes a first buffer tank 8000 and a second buffer tank 9000 as compared to the embodiment shown in FIG. 14.

The first buffer tank 8000 is disposed between the first material reservoir 300 and the multichannel microsphere forming unit 100. The first buffer tank 8000 is connected to the first material outlet 320 of the first material reservoir 300 and receives the first raw material from the first material reservoir 300.

Likewise, the second buffer tank 9000 is disposed between the second material reservoir 400 and the multichannel microsphere forming unit 100. The second buffer tank 9000 is connected to the second material outlet 420 of the second material reservoir 400 and the second raw material is supplied thereto from the second material reservoir 400.

As described above, the flow pressures of the first raw material and the second raw material transferred through the first material exhausting port 320 and the second material exhausting port 420 are associated with the level of the first raw material or the second raw material in the first material reservoir 300 or the second material reservoir 400. The first buffer tank 8000 and the second buffer tank 9000 have a considerably smaller volume than the first and second material reservoirs 300, 400. The first buffer tank 8000 and the second buffer tank 9000 are installed to relieve the pressure components in accordance with the liquid level of the first raw material and the second raw material, making it possible to stabilize the flow rate supplied to the multichannel microsphere forming unit 100, i.e., to maintain the pressure thereto constant.

The first buffer tank 8000 further comprises a first material shut-off valve 8100 and the second buffer tank 9000 further comprises a second material shut-off valve 9100.

The first material shut-off valve 8100 or the second material shut-off valve 9100 shut off the first buffer tank 8000 or the second buffer tank 9000 from the first material reservoir 300 or the second material reservoir 400 when the first material reservoir 300 or the second material reservoir 400 need to be replaced or to be charged with raw materials, making it possible to maintain the continuous formation of microspheres until the raw materials in the first buffer tank 8000 or the second buffer tank 9000 are exhausted without supplying of the raw materials from the first material reservoir 300 or the second material reservoir 400. The presence of the shut-off valves facilitates the continuous forming of the microspheres during, for example, during the shut-off, the need for the first material reservoir 300 or the second material reservoir 400 to be replaced or filled.

In addition, the presence of the first buffer tank 8000 and the second buffer tank 9000 prevent the loss in cost due to the disposal of the raw materials in case of a failure or a maintenance which may occur during the manufacturing process.

Medical Products Developed Using the Proposed Principles and the Mass Production Apparatus Developed Based Thereon The inventors have developed the basic principles for optimizing the mass production of monodisperse biodegradable microspheres and have come up with an apparatus dedicated therefor based on the basic principles developed. The apparatus developed along with the basic principles can be easily be used for the mass production of a variety of medical products based on biodegradable polymer microspheres with the desired physiological functions/efficacies by mere addition and/or proper mixing of a substance having a desired physiological function or a pharmacological function to a biodegradable polymer phase solution formed by dissolving a biodegradable polymer in an organic solvent and forcing the flow of the biodegradable polymer solution incorporating therein the substance to come into a physical contact with the flow of a solution which is immiscible thereto, resulting in the formation of microspheres having the desired properties.

The inventors have applied the developed principles and the apparatus to fabricate three exemplary medical products, namely, medical filler, heartworm preventive and hair loss preventive, all of which are incorporate therein the biodegradable polymer-based microspheres formed using therewith The medical products developed all have two common features, namely, being able to be injected into the body and the medical products, or to be more specific, the biodegradable polymer therein degrades over time, i.e., during its biodegradation period. Further, excluding the medical filler, the heartworm preventive and the hair loss preventive, as a consequence of the substance having the desired physiological function or a pharmacological function being released into the body as the biodegradable polymer degrades during its degradation period, qualifying the products to be polymeric drug delivery systems (PDDS). In other word, the medical products developed based on biodegradable polymer-based microspheres serve as injectable implants in the body and may also function as polymeric drug delivery systems (PDDS) exposing the physiological or pharmacological function throughout the biodegradation period. To summarize, in order for medical products to be qualified as PDDS, they must fulfill the following requirements:

(1) They are injectable;
(2) They have an associated degradation period; and
(3) They have an associated drug delivery rate.

The biodegradation period is supposed to depend mainly upon the type and quantity of the biodegradable polymer being used in forming the microspheres. Thus, if the type is defined, for example, as PCL, the biodegradation period will be determined by the quantity of the biodegradable polymer used. As the quantity of biodegradable polymer is determined by the size of the microspheres if the concentration of the biodegradable polymer dissolved in the biodegradable polymer phase solution is set to be a specific value or a specific range, the microspheres can be designed to have a longer biodegradation period by making them to have a larger size. In other word, the size of the microspheres may be determined according to the desired biodegradation period. However, if the size of the microspheres is under 20 μm, macrophages may predate the microspheres and the biodegradation period may consequently be shortened. Therefore, the three exemplary medical products should have a target size greater than 20 μm and at the same time, should be small enough to be injected. The injectability issue will be discussed later.

The drug delivery rate, by definition, is the degree of absorption into the body per unit time of the drug dissolved in the biodegradable polymer making up the microspheres or the rate at which the drug dissolved in the biodegradable polymer making up the microspheres get absorbed into the body. The drug delivery rate corresponds to the surface occupancy area or surface occupancy ratio of the drug in the microspheres, the implication thereof being that it depends mainly on the concentration ratio between the biodegradable polymer and drug constituting the microspheres. That is, the size of the microspheres is related to the biodegradation period or the release period of the drug and the relevance thereof to the drug delivery rate is comparably small.

The injectability refers to the ease of dermal injection using the syringe and the presence of pain or foreign body sensation at the time of injection or after injection. Injectability is an especially important factor when the medical products incorporating therein the biodegradable polymer-based microspheres are used as injectable medical fillers or in injectable drug delivery systems.

The smaller the needle used for the infusion of microspherical products, the less pain the person feels. Therefore, the smaller the size of the microspheres, the smaller the inner diameter of the needle can be used, allowing the microspheres to pass through the needle without clogging and penetrate into the skin. As the size of the microspheres increases, it is necessary to use a needle having a larger inner diameter, and the person being injected may feel the pain or discomfort due to the injection and may also feel a greater foreign body sensation after the injection.

However, as described above, since the size of the microspheres is strongly related to the biodegradation period, the size of the microspheres should be appropriately selected depending on the subject to which these products are to be applied and the purpose of use thereof.

For example, if these medical products are injected into the human as medical fillers and hair loss preventives, usually multiple injections are required to be performed on the face or scalp. Therefore, when applying these products as medical fillers and hair loss preventives, injectability should be the primary consideration. For such applications requiring multiple injections into the human, the microspheres in these products should be of as small a size as possible with an adequate biodegradation period, and hence, for these applications, the diameter of the microspheres in the medical products ranges from 20 μm to 70 μm, for example, usually around 50 μm.

On the other hand, when these products are injected into animals as a drug delivery system (DDS), the frequency and the site of injection are not as critical. Such example includes Heartworm preventives, which is usually injected into the chest of a dog and the injectability may not be as critical as for the human. For such applications requiring injection into animal skins are desired, microspheres in the medical products may have a relatively large diameter with a view to obtaining as long a biodegradation period as possible. The diameter of the microspheres in such cases may range from 100 μm to 150 μm, for example, be around 130 μm.

Based on these considerations, the inventors have applied the basic principles for optimization of the mass production of microsphere and the apparatus based thereon in the production of three types of medical products incorporating therein biodegradable polymer-based microspheres in two size ranges, i.e., 20 μm to 70 μm and 80 μm to 130 μm. That is, the microchannels in the multichannel microsphere forming unit are designed to have one side thereof being 50 μm and 110 μm, respectively, wherein the multichannel microsphere forming units having microchannels with one side thereof being 50 μm used for the mass production of the microspheres having a diameter in 20 μm to 70 μm range and the other, i.e., the multichannel microsphere forming unit including therein microchannels with one side thereof being 110 μm for the mass production of microspheres having a diameter in 80 μm to 130 μm range, based on the 30% rule for the microchannel dimension required described hereinabove.

Once the dimension of the microchannels is fixed, the flow rate of the water-phase solution is then used to further control the diameter of the microspheres formed based on the basic principles, followed by using the flow rate of the biodegradable polymer-phase solution to fine tune the diameter thereof.

The flow rate of the water-phase solution and the flow rate of the biodegradable polymer-phase solution are controlled by controlling the flow rates of the solutions supplied to the multichannel microsphere forming unit 100 from the first reservoir 300 and the second reservoir 400 using the flow rate control unit 200.

These design techniques are incorporated in the mass production apparatus developed and described above to allow the fabrication of the desired medical products.

The modification incorporated into the mass production apparatus depending on the application requirement resulted in the production of a large volume of monodisperse biodegradable polymer-based microspheres having the desired target size.

Further investigation of the three medical products fabricated using the processes and the mass production apparatus of the present invention is as follow.

Microspherical Products Developed for Medical Filler

As a method for removing wrinkles, medical fillers, such as injectable bovine collagen, have been injected locally into the wrinkled facial area.

Such a medical filler, however, needs to be improved in the following areas: (1) must have a close dimensional accuracy with narrow size distribution to reduce the side effects such as allergies caused by the bio-toxicity and Kreutzfeld Jacob's disease; (2) should preferably be able to prevent the absorption in vivo for increased sustainability; and (3) should preferably be able to guarantee dermal injectability. As a consequence, there has been a growing need for the development of a medical filler that does not cause any undesirable biological reactions in the human body, does not cause aggregation, needle clogging, or nodule forming during injection, and shows slow reabsorption, and one type of medical fillers meeting the requirements described is a medical filler incorporating therein biodegradable polymer-based microspheres, for example is Ellanse™ M.

Generally, biodegradable polymer-based fillers have been prepared using phase separation, spray drying, and solvent extraction-evaporation. These manufacturing methods tend to manufacture microspheres having a relatively broad size distribution and a non-uniform size. Therefore, to obtain microspheres of the desired size, a separate size-refining process, such as sieving is required. As a result, microspheres ranging outside the target size are discarded, resulting in a decrease in final yield.

Thus, the inventors of the present invention have investigated the mass production of monodisperse biodegradable polymer-based microspheres, which slowly degrade inside the human body, using the basic principles developed and the mass production apparatus based thereon with a view to applying and extending in the technology developed in the mass production of PDDS for various purposes.

Monodisperse biodegradable polymer-based microspheres for use in medical fillers having a diameter close to the target diameter determined based on injectability, reducing needle clogging, nodule formation and flocculation and finally, reducing the occurrence of foreign body sensation or pain at the time of injection or after the injection are mass produced using the basic principles and the mass production apparatus based thereon.

The mass produced biodegradable polymer-based microspheres for use in medical fillers using the basic principles and the apparatus of the present invention are monodispersed and have a spherical shape in general, the diameter of the microspheres being about 20 μm to 70 μm, depending on the target initially set.

Further, the size distribution (span value) of the biodegradable polymer-based microspheres is one or less according to the formula below:

$$\frac{Dv_{0.9} - Dv_{0.1}}{Dv_{0.5}}$$

wherein, $Dv_{0.1}$ is the size of microsphere within 10% in distribution, $Dv\_0.5$ is the size of microsphere within 50% in distribution, and $Dv\_0.9$ is the size of microsphere within 90% in distribution. If the size distribution is larger than one, the size distribution is regarded as uneven, and the yield of the microspheres will be low.

In one embodiment of the present invention, the biodegradable polymer of the present invention is selected from the group consisting of polylactic acid (PLA), polyglycolic acid (PGA), polylactic-co-glycolic acid (PLGA), polycaprolactone (PCL), and derivatives thereof, and is preferably polycaprolactone, but is not limited to the examples. The number average molecular weight of the biodegradable polymer is not particularly limited, but is 5,000 to 300,000, preferably 8,000 to 250,000, and more preferably 10,000 to 200,000.

In one embodiment of the present invention, the microspheres comprising the biodegradable polymer produced using the production method and apparatus of the present invention are not particularly limited in their use, but may be, for example, a skin cosmetic or medical filler, and can be used as a subcutaneous or intradermal injection-type filler, particularly in vivo, but is not limited to the examples.

In one embodiment of the present invention, the in vivo resorption time of the biodegradable polymer-based microspheres produced according to the production method and the apparatus of the present invention is not particularly limited, but considering the use as biodegradable skin cosmetics or medical fillers, it is preferable that they are resorbed in vivo within one to three years.

[Product Example 1]—Mass Production of Monodisperse Biodegradable Polymer-Based Microspheres Considering the biodegradation period and injectability of the biodegradable polymer-based microspheres for use in medical fillers, the optimum size of the microspheres needed was determined to be 60 μm, with the lower limit and the upper limit being 40 μm and 80 μm, respectively.

The biodegradable polymer-phase solution was prepared by dissolving 15 wt % of Polycaprolactone (PCL) having a Mn of 45,000 in dichloromethane solvent (boiling point: 39.6° C.) and the water-phase solution, by dissolving, as a surfactant, 0.25 wt % of Polyvinyl alcohol (PVA) having a molecular weight of 85,000 to 124,000 in purified water One side, i.e., the width, of the microchannel incorporated in the multichannel microsphere forming unit 100 of the mass production apparatus in accordance with the present invention was set at 60 μm.

The water-phase solution and the biodegradable polymer-phase solution were filled respectively into the first reservoir 300 (see FIG. 13) and the second reservoir 400 (see FIG. 14) before being fed into the multichannel microsphere forming unit 100 of the mass production apparatus illustrated in FIG. 16.

At this time, the flow rate of the aqueous solution was increased or decreased while the flow rate of the biodegradable polymer phase solution was kept constant, and the size of the microspheres formed was determined. The flow rate of the aqueous solution was then adjusted so that the microspheres were in the vicinity of the target size, that is, about 50 μm.

Then, the size of the microspheres formed was fine-tuned by adjusting the flow rate of the biodegradable polymer phase solution while the flow rate of the aqueous solution was kept constant.

Referring to FIG. 16, the flow rate of water-phase solution and the flow rate of the biodegradable polymer-phase solution in the multichannel forming unit 100 are adjusted using the flow rate control unit 200.

The temperature of the water-phase solution and the biodegradable polymer-phase solution were maintained at 15° C.

The microspheres in the product reservoir 600 (see FIG. 16) were collected. Thereafter, the solvent, e.g., dichloromethane, was first extracted from the collected microspheres. After filtering the water-phase solution containing the microspheres, the residual surfactant and solvent, e.g., PVA and dichloromethane, were removed from the microspheres through washing before being dried, resulting in the formation of the desired monodisperse biodegradable polymer-based microspheres.

[Product Example 2]—Preparation of Monodisperse Biodegradable Polymer-Based Microspheres for Use in Medical Fillers Since the minimum diameter of the microspheres for being injected in to the human body is between 20 and 30 μm, the target diameter of the microspheres for use in medical fillers to be formed using the basic principles and the mass production apparatus developed based thereon was set between 20 μm and 40 μm, and in line with the basic principles, i.e., so-called the 30% rule, one side, i.e., the width, at least, of the microchannels in the multichannel microsphere forming unit 100 was set at 30 μm.

Other than the dimension of the microchannels, the same processes described in the Product Example 1 were used to prepare the monodisperse biodegradable polymer-based microspheres for use in medical fillers.

[Comparative Example]—Formation of PCL-Based Microspheres Using the Principles and the Apparatus Developed and Comparison Thereof with the PCL-Based Microspheres in Ellanse™ M Formed Using the Solvent Extraction-Evaporation The biodegradable polymer-based microspheres used in Ellanse™ M, a commercially available and representative medical filler, are prepared using the solvent extraction-evaporation method and are used as a comparison, i.e., as the Control Product.

The biodegradable polymer-phase solution was prepared by dissolving polycaprolactone (PCL) having a Mn of 45,000 in a solvent of dichloromethane (boiling point: 39.6° C.) at a concentration of 15 wt % and the water-phase solution, by dissolving polyvinyl alcohol (PVA) having a Mw of 85,000~124,000 as a surfactant in purified water at a concentration of 0.25 wt %.

The desired monodisperse biodegradable polymer-based microspheres were formed by introducing these solutions into the mass production apparatus of the present invention and manipulating the process parameters as described hereinabove.

[Test Example 1] SEM Image Analysis of the Microspheres for Use in Medical Fillers The monodisperse biodegradable polymer-based microspheres obtained using the basic principles and the apparatus developed in Product Example 1 were visually investigated. There are shown in FIGS. 8 and 9 a SEM image of single biodegradable polymer-based microsphere obtained and a SEM image of monodisperse biodegradable polymer-based microspheres obtained, respectively, each of the microspheres having a diameter of 50 μm.

As shown in FIGS. 8 and 9, the mass-produced microspheres of Product Example 1 are spherical with a smooth surface and are monodispersed, each of the microspheres having a constant size and shape.

Figure 56:
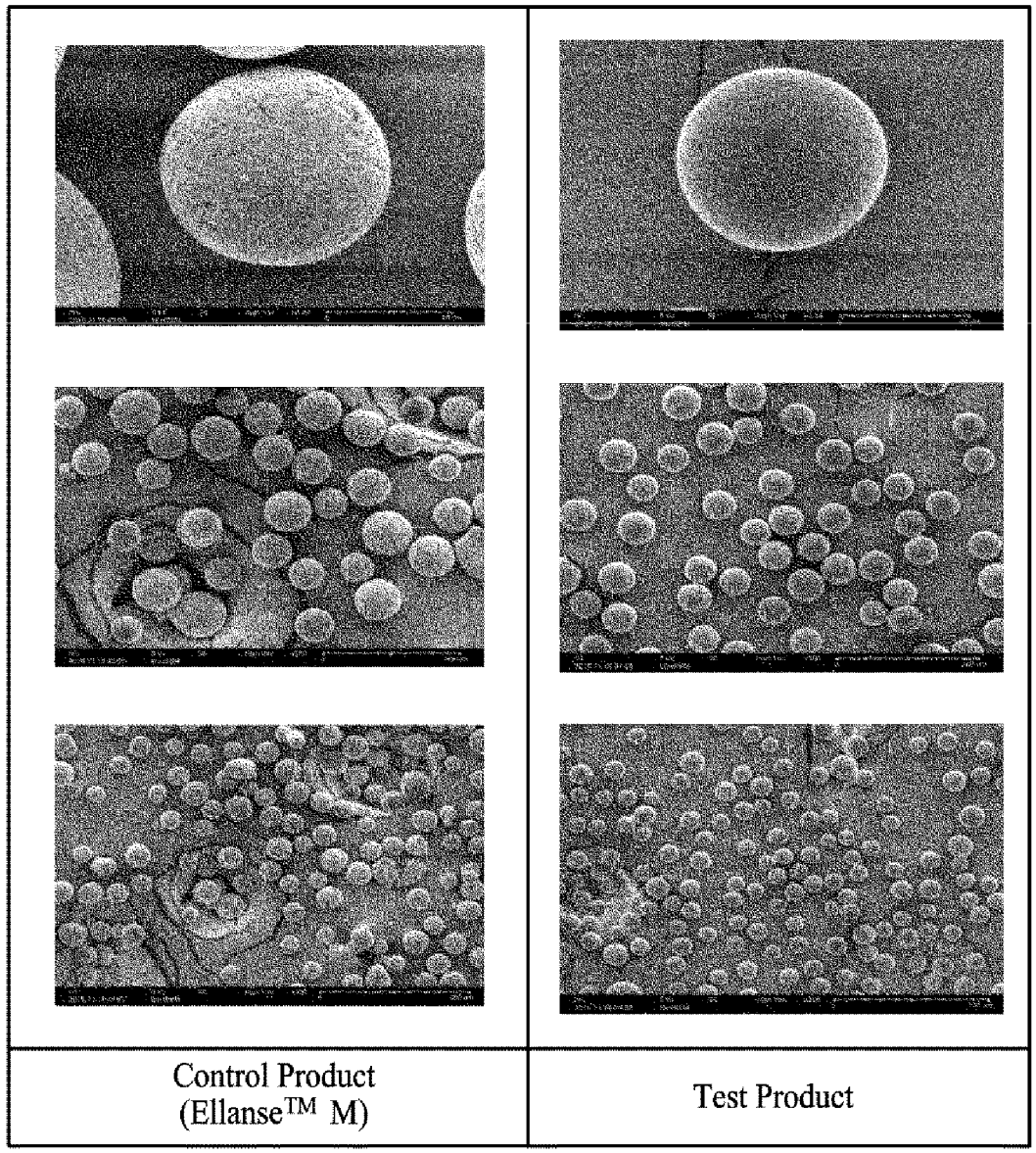
FIG. 56 illustrates an SEM Image Comparison of the Control Product (Ellanse™ M) and the Test Product (Perimore).

There are shown FIG. 56 a comparison of the SEM images of the microspheres produced in Product Example 2, each of the microspheres having a target diameter of 30 μm and those for Ellanse™ M having a diameter about 40 μm, as the Control Product.

Using a SEM, the morphology of microspheres was visually compared with that of the commercially available product, Ellanse™ M. According to the morphology analysis, the morphology of the microspheres of Product Example 2 is comparable to that of Ellanse™ M, i.e., spherical in shape.

It is relatively harder to produce monodisperse microspheres with a smaller diameter than the ones with a large diameter. Product Example 2 has a smaller diameter than Product Example 1 and Comparative Example, that is, Ellanse™ M. In spite the microspheres of Product Example 2 mass-produced using the basic principles and the mass production apparatus according to the present invention are smaller in size, they have a smoother shape than the Comparative Example/Control Agent, i.e., Ellanse™ M, and the overall size distribution is relatively constant and monodispersed.

In particular, the production of the biodegradable microspheres used in Ellanse™ M using the solvent extraction-evaporation method, results a low yield, for the solvent extraction-evaporation method results in producing microspheres having a wide particle size distribution and in order for the biodegradable microspheres to be used in the product, those microspheres not meeting the size requirement must first be selectively filtered and sieved out, leaving only a small amount of the microspheres from the lot meeting the size requirement.

However, in contrast to the solvent extraction-evaporation method, the basic principles and the mass production apparatus of the present invention are capable of ensuring a mass production of monodisperse biodegradable microspheres from the beginning of the production, therefore, not requiring the filtering and sieving steps required in the solvent extraction-evaporation method, minimizing the loss therefrom, which, in turn, results in a high yield.

[Test Example 2] GPC Analysis of the Microspheres for Use in Medical Fillers

Since the biodegradation period of the microsphere is dependent on the molecular weight of the polymer, the molecular weight of the microspheres of Product Example 2 and that of the Control Agent was investigated.

Figure 57A:
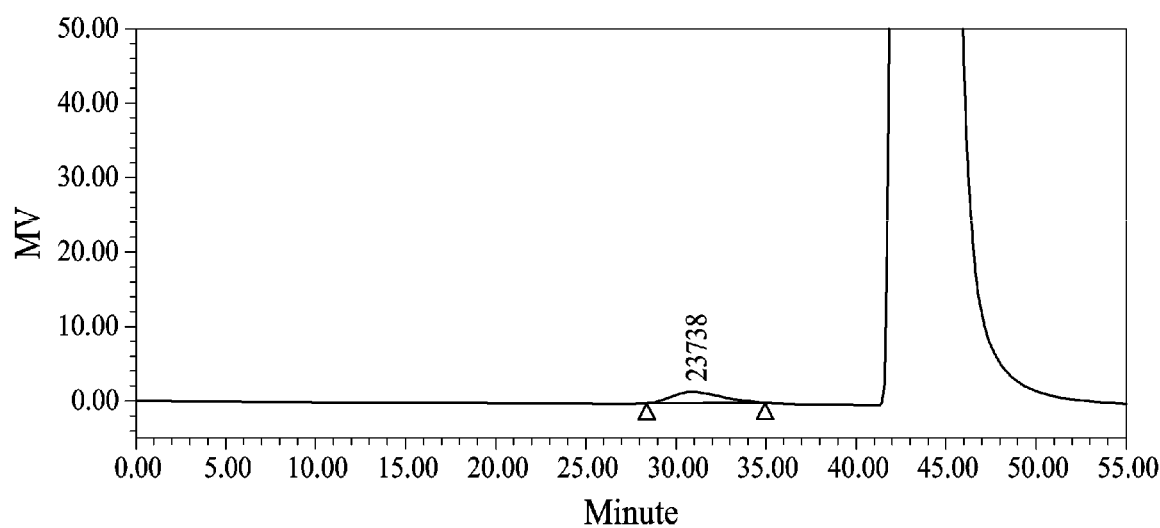
FIG. 57A to 57C illustrate a GPC Analysis of PCL (Polycaprolactone, Purac®), the Control Product (Ellanse™ M) and the Test Product (Perimore), respectively.
Figure 57B:
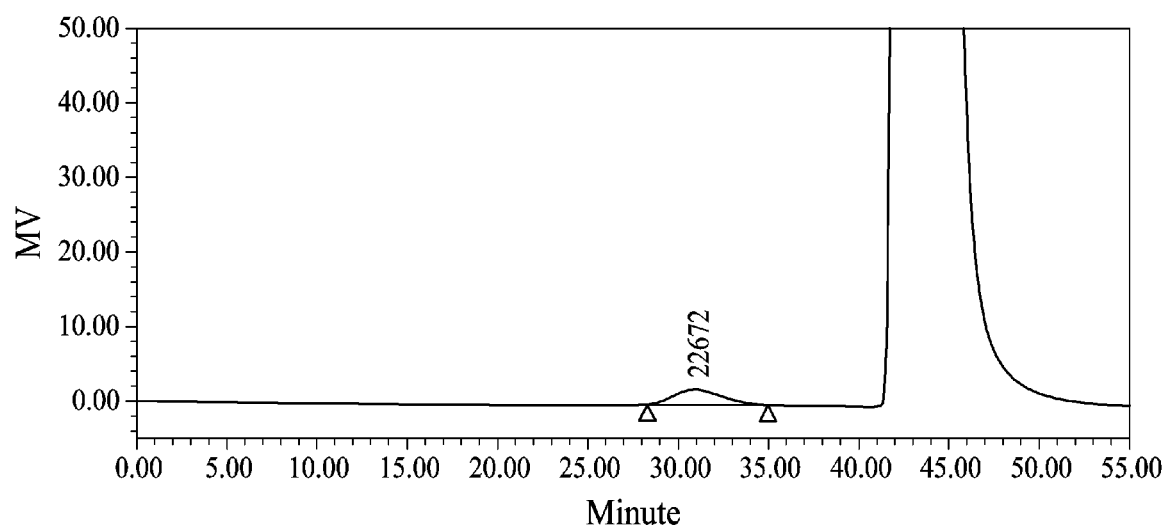
Figure 57C:
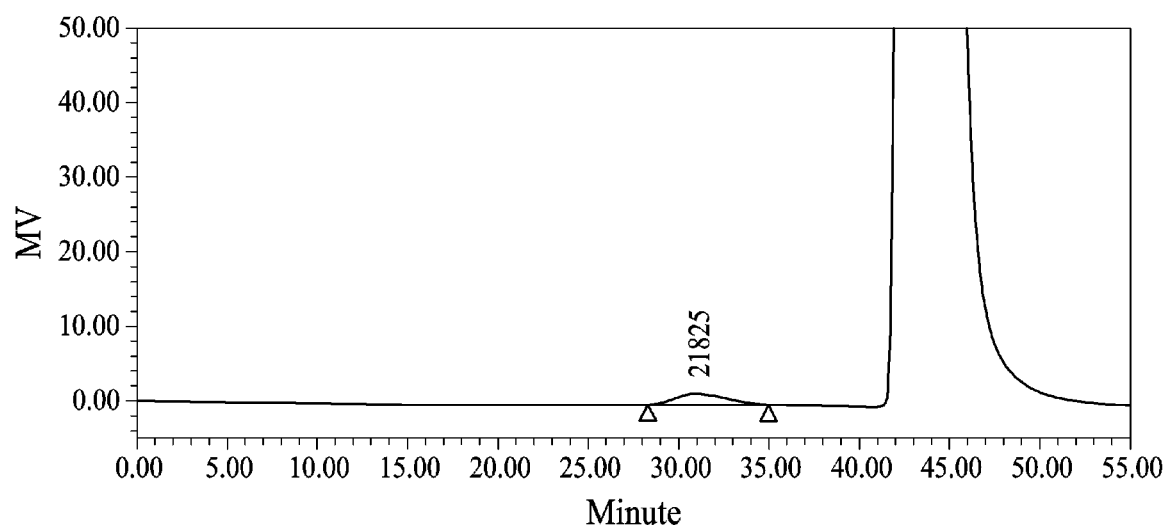

There are shown in FIGS. 57A to C the results of GPC analysis of the raw powder of the biodegradable polymer PCL (Polycaprolactone, Purac®) used, the results of GPC analysis of the Control Product, i.e., Ellanse™ M, and the results of GPC analysis of the Test Product, i.e., microspheres of Product Example 2. Table 7 summarizes the results of GPC analysis of raw powder for biodegradable polymers, the Control Product, and Test Product.

TABLE 7

Results of GPC analysis of raw powder for biodegradable polymers, the Control Product, and Test Product

| Classification | | Mn | Mw | MP | Mz | $M_{z+1}$ | Poly Dispersity |
|---|---|---|---|---|---|---|---|
| Material (Powder) | PCL(Purac ®) | 14461 | 23421 | 23738 | 33750 | 43427 | 1.619576 |
| Particle | control agent (Ellanse ™ M) | 15013 | 23829 | 22672 | 33776 | 43344 | 1.587199 |
| | Test Agent (product example 2) | 13259 | 23032 | 21825 | 34233 | 44718 | 1.737021 | wherein,
a) Mn is Number-average Molecular Weight
b) Mw is the weight-average molecular weight
c) Mz is the Z-average molecular weight.

According to the results obtained from the GPC analysis, the molecular weights of the PCL powder as the raw material, the Control Product, i.e., Ellanse™ M and the Test Product, i.e., the microspheres of Product Example 2 were similar to each other and the based thereon, it can be concluded that the Control Product and the Test Product have the similar biodegradation period and size distribution as the polymer concentration therein varies.

[Test Example 3]—Size Distribution Analysis of the Microspheres for Use in Medical Fillers The diameters of the Control Product, i.e., Ellanse™ M, and the Test Product, i.e., the microspheres of Product Example 2, were compared and analyzed using a particle size analyzer (PSA).

Figure 58A:
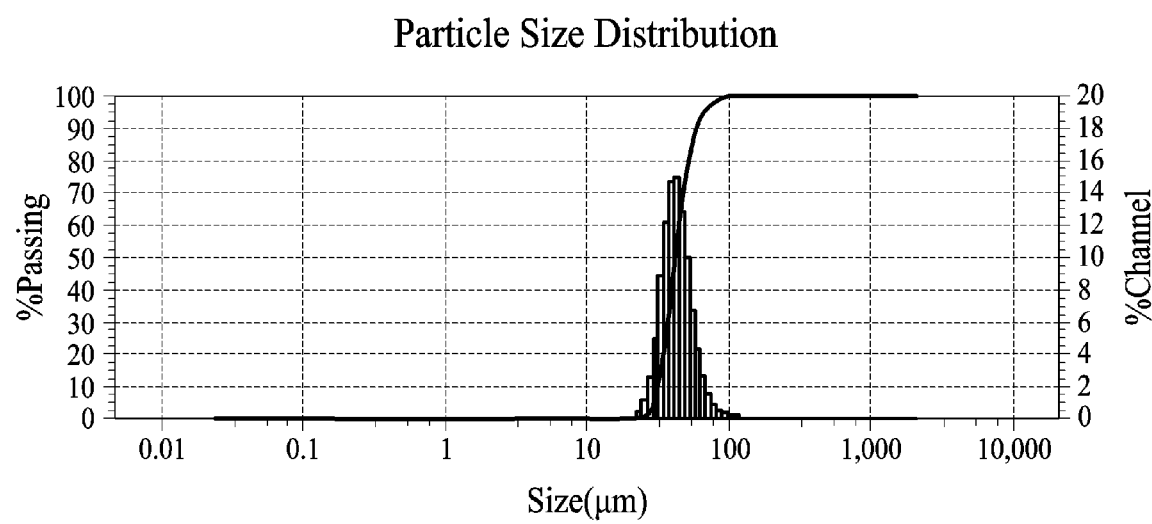
FIGS. 58A and 58B illustrate a Particle Size Distribution of the Control Product (Ellanse™ M) and the Test Product (Perimore), respectively, obtained using a PSA (Particle Size Analyzer).
Figure 58B:
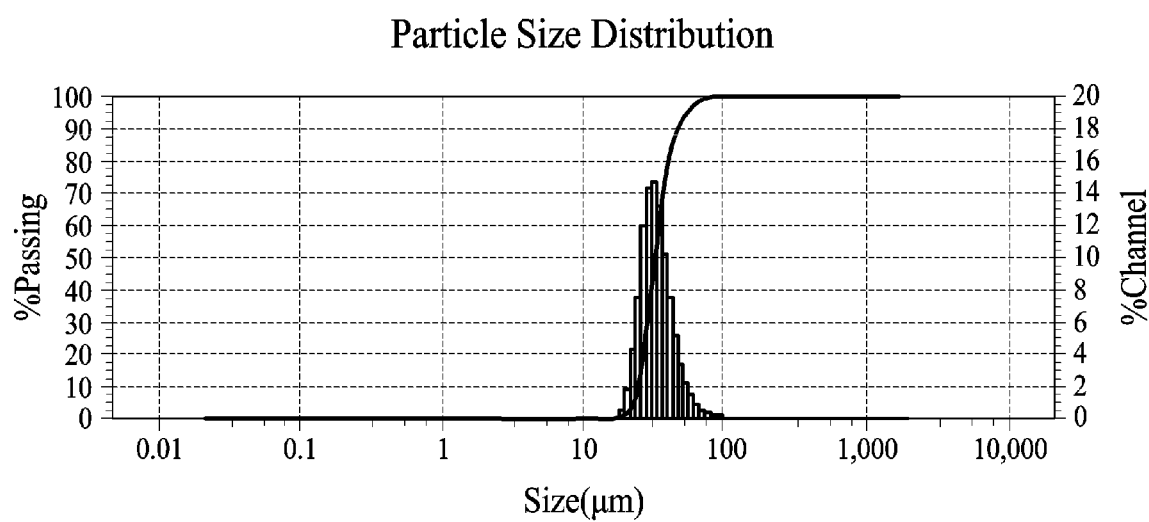
Figure 59A:
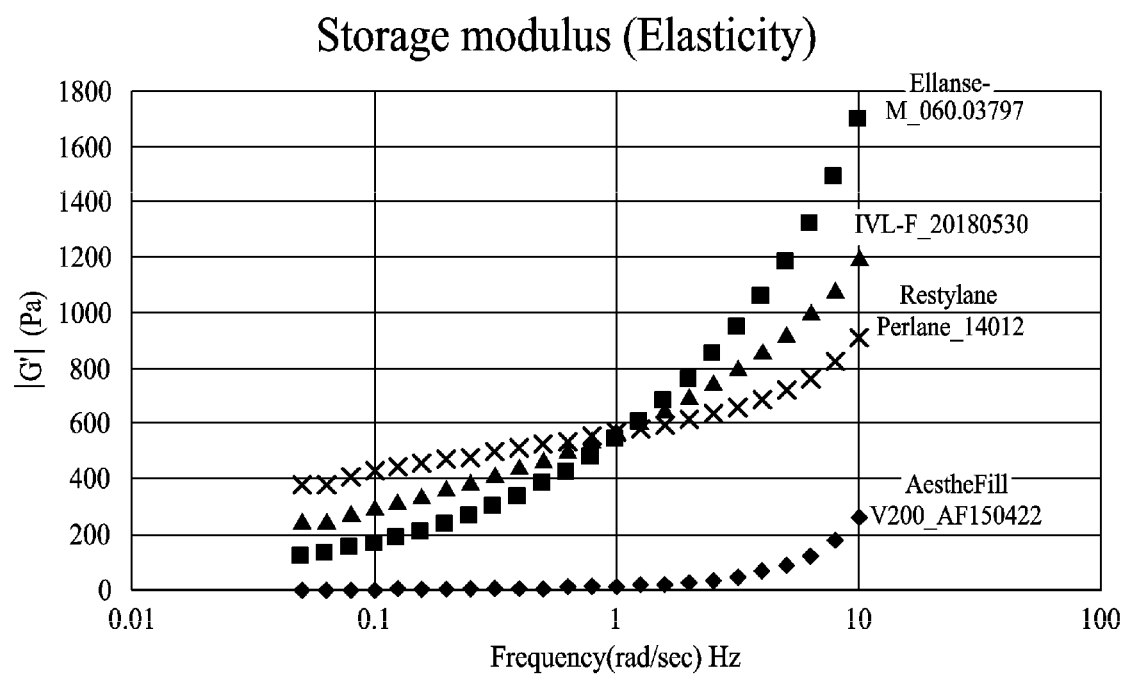
FIGS. 59A to 59D illustrate Storage Modulus, Loss Modulus, Complex Viscosity and Phase Angle of IVL-F_180530 IVL-F_180530, Restylane® Perlane+Lido, AestheFill® V200 and ELLANSE™ M, respectively, measured and compared using a Rheometer (Kinexus, Malvern, U.K.).
Figure 59B:
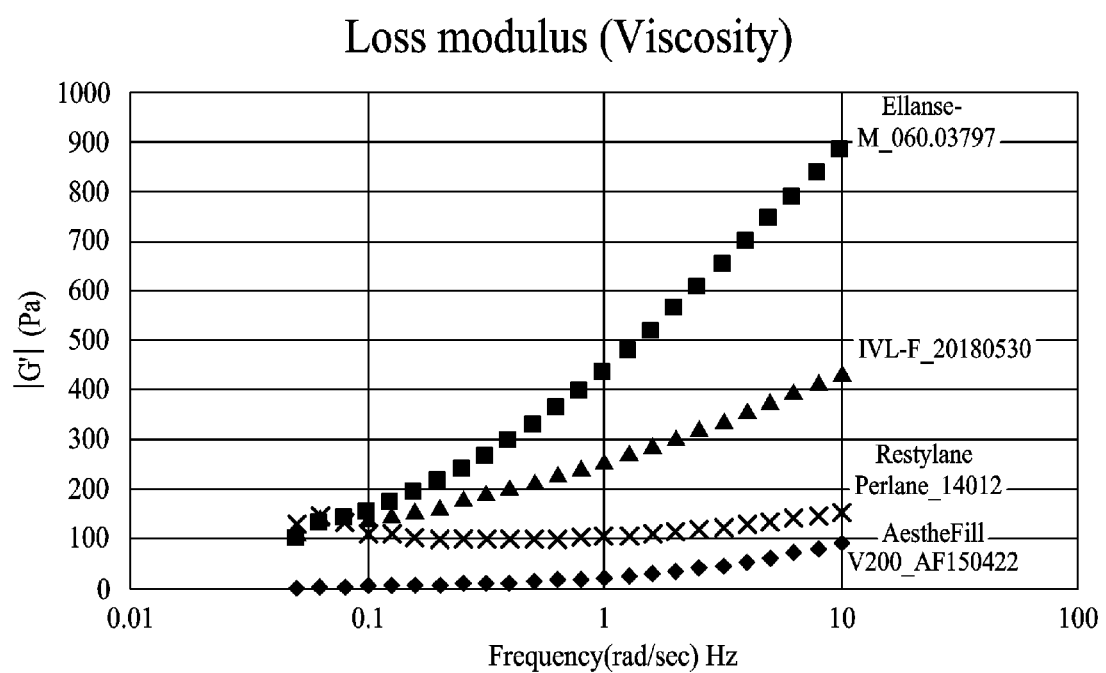
Figure 59C:
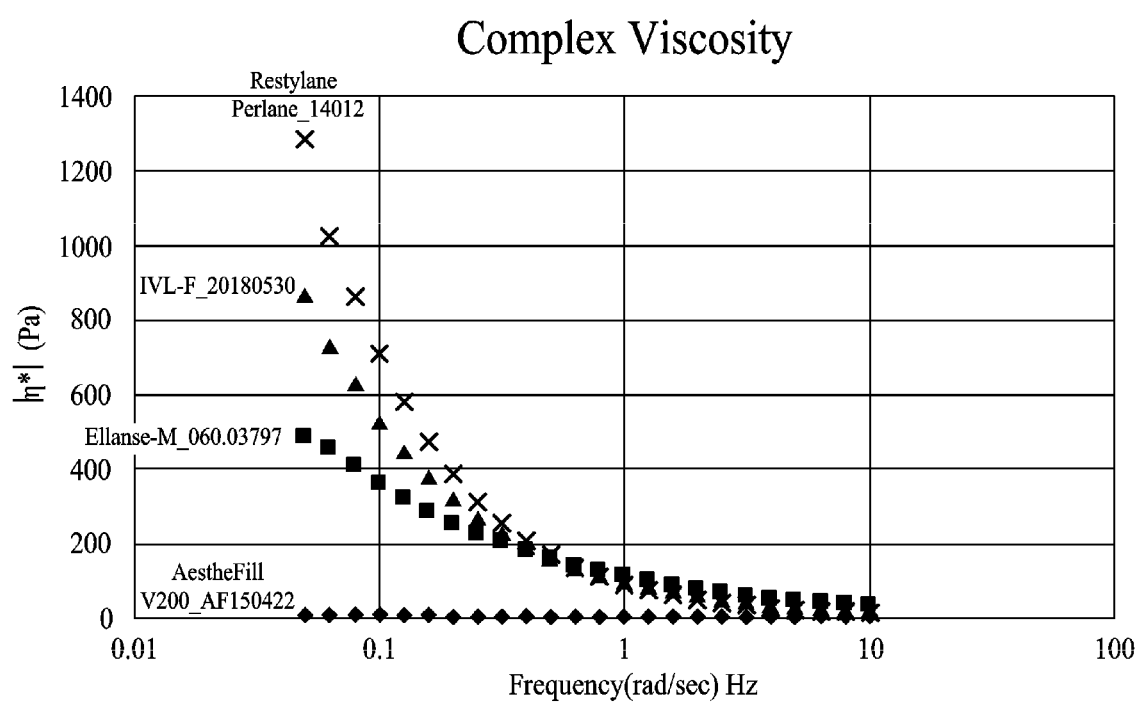
Figure 59D:
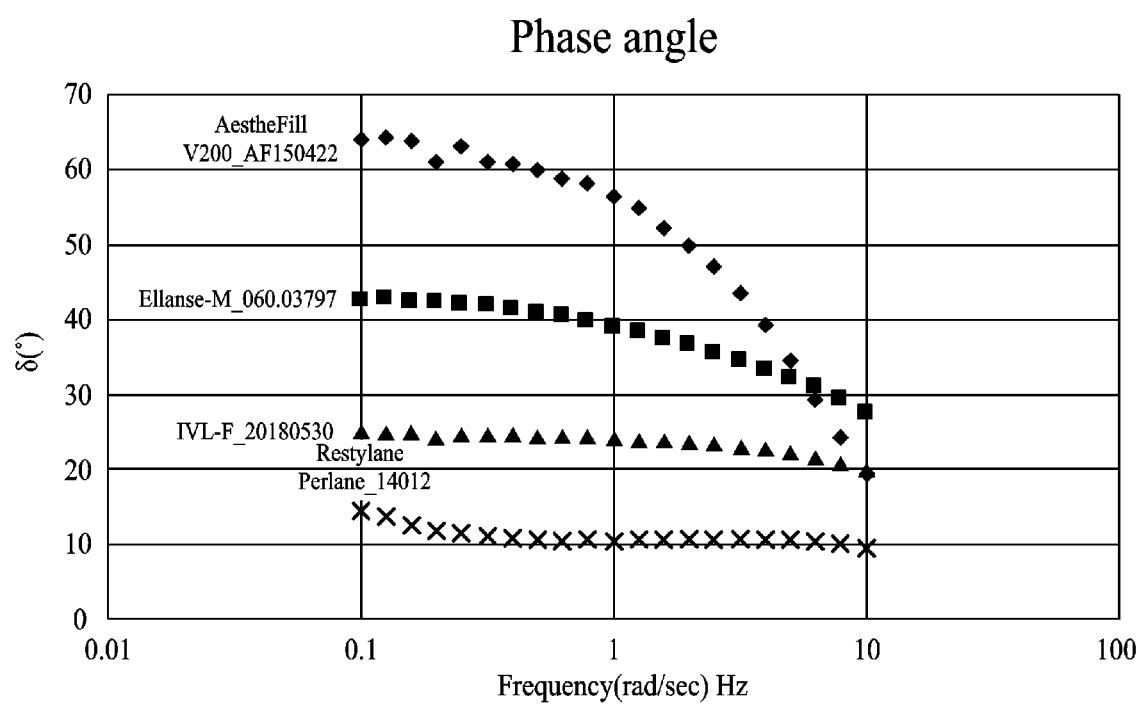

FIG. 58A is a graph of the particle size distribution of the Control Product, i.e., Ellanse™ M, and FIG. 58B, a graph of the particle size distribution of the Test Product, i.e., the microspheres of Product Example 2.

Referring to FIG. 58A, the Control Product, i.e., Ellanse™ M, was analyzed to have an average diameter of 41.59 μm and was analyzed to have a size distribution of 19.95 μm.

Referring to FIG. 58B, the Test Product, i.e., microspheres of Product Example 2, was analyzed to have an average diameter of 33 μm and was analyzed to have a size distribution of 16.65 μm.

As described above, the microspheres of Product Example 2 have a size of 30 μm, close to 20 μm, which is close to the limit diameter for exhibiting an appropriate biodegradability in vivo. Despite the difficulty of controlling the size distribution when the microspheres are small, the Test Product, i.e., Product Example 2, had a narrower diameter distribution, i.e., monodisperse, and also a smaller diameter than the Control Product, i.e., Ellanse™ M.

[Test Example 4]—Viscoelasticity of the Microspheres for Use in Medical Fillers

The viscoelastic properties of the Test Product, i.e., the microspheres of Product Example 2, and the Control Product, i.e., Ellanse™ M were measured and compared using Rheometer (Kinexus, Malvern, U.K.). In addition, as other Control Products, the viscoelastic properties of Restylane® (Perlane+Lido) and AestheFill® (V200) were also measured and compared.

There are shown in FIGS. 59A to D comparisons of the measured elasticity, the measured viscosity, the measured complex viscosity and the phase angle of the Test Product and the Control Products, respectively. Table 10 summarizes the viscoelastic measurements of the Test Product and Control Products.

TABLE 10

Summary of the Viscoelastic Measurements of the Test Product and Control Products

| | Storage Modulus[1] G'(Pa) | Loss Modulus[2] G"(Pa) | Complex Viscosity[3] η*(Pas) | Phase Angle[4] δ(°) |
|---|---|---|---|---|
| Test Product | 573.9 | 257.4 | 100.3 | 24.16 |
| Restylane ® Perlane + Lido | 566.2 | 105.2 | 91.88 | 10.53 |
| AestheFill ® V200 | 14.4 | 21.85 | 4.175 | 56.62 |
| ELLANSÉ ™ M | 537.4 | 436.5 | 110.4 | 39.08 | wherein, G' is the storage modulus, i.e., the elastic portion of the sample at the measured frequency. G" is the loss modulus, i.e., the viscous portion of the sample at the measured frequency. η* (complex viscosity) is a vector term representing viscosity and elasticity together that reflects the degree of deformation against external force and δ is the phase angle between viscosity and elasticity terms of η*. Compared with the Control Product (Ellanse™ M), the elasticity of the Test Product (Product Example 2) was similar to that of the Control Product, but the viscosity of the Test Product was lower than that of the Control Product. The smaller the viscosity of the microspheres is, the more easily the microspheres can be injected into the human body. In other words, since the viscosity of the Test Product is lower viscosity than that of the Control Product (Ellanse™ M), the Test Product can be injected more easily into the human body. Further, since the elasticity of the test product is similar to that of the Control Product (Ellanse™ M), the supporting force of the Test Product is as good as that of the Control Product in the human body, allowing the microspheres of the Test Product to physically maintain themselves as good as the Control Product in the human body.

In addition, according to the measured complex viscosities, the degree of deformation by the external force was analyzed to be similar in the Test product and Control Product (Ellanse™ M).

[Test Example 5]—Injection Force Analysis of the Microspheres for Use in Medical Fillers Medical fillers should be injected into the human body without an excessive force. Thus, the Test Product, i.e., the microspheres of Product Example 2, and the Control Product, i.e., Ellanse™ M, were compared with each other using a texture analyzer (Stable Micro System, U.K.). Additionally, the injection forces for other Control Products such as Restylane® (Perlane+Lido) and AestheFill® (V200) were also measured and compared.

Figure 60A:
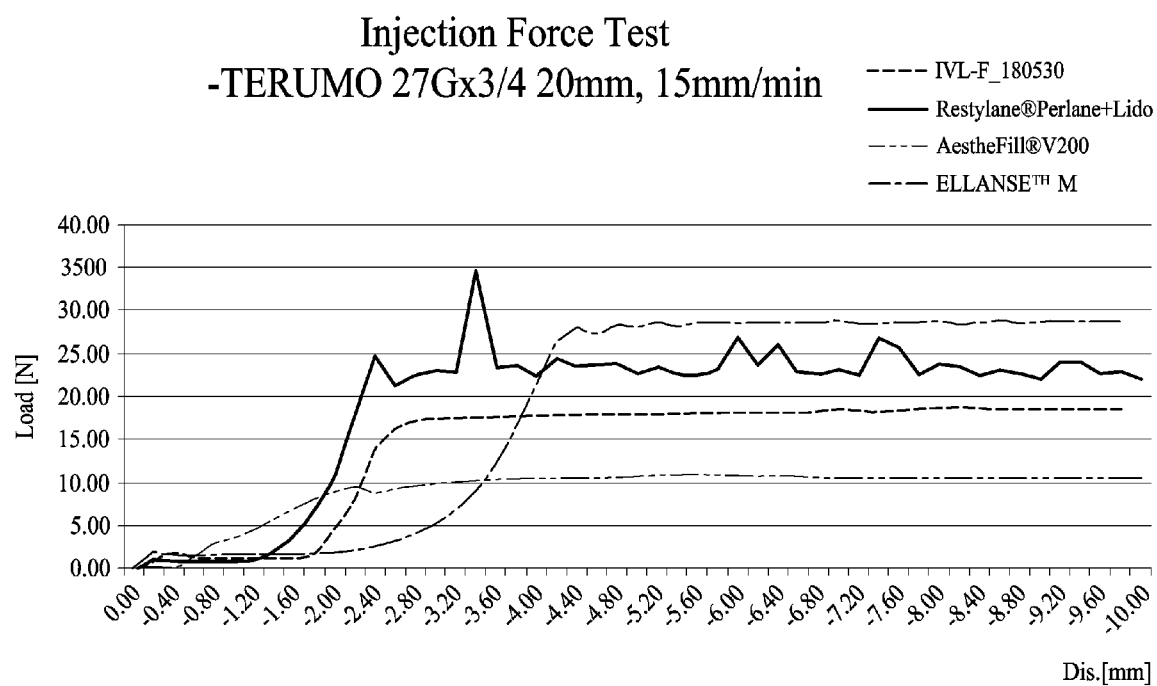
FIGS. 60A and 60B illustrate an Injection Force Test for IVL-F_180530 IVL-F_180530, Restylane® Perlane+Lido, AestheFill® V200 and ELLANSE™ M obtained using TERUMO 27Gx3/4 and DN Co. 27G.
Figure 60B:
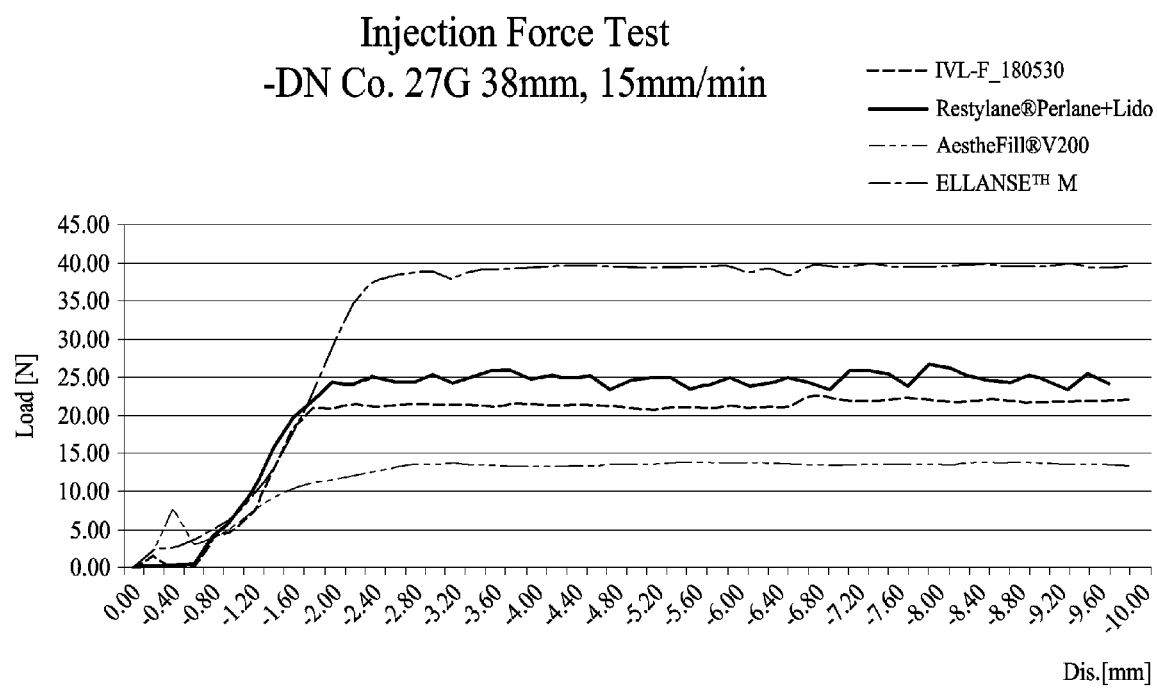

FIG. 60A is a graph of the injection force measurements of the Test and Control Products obtained using a TERUMO 27Gx3/4 needle and FIG. 60B is a graph of the injection force measurements of the Test and Control Products obtained using a DN Co. 27G needle. Table 11 summarizes the injection force measurements of the Test and Control Products above.

microspheres of Product Example 2, using the basic principles and the apparatus of the present invention, the biological stability evaluation thereof, was carried out and the results therefrom are summarized in Table 12.

TABLE 11 the injection force measurements of the Test and Control Products

|  | Test Product (Example Product 2) | | Restylane ® Perlane + Lido | | AestheFill ® V200 | | ELLANSE ™ M | |
| --- | --- | --- | --- | --- | --- | --- | --- | --- |
|  | TERUMO 27Gx3/4 0.4 × 20 mm | DN Co. 27G 38 mm | TERUMO 27Gx3/4 0.4 × 20 mm | DN Co. 27G 38 mm | TERUMO 27Gx3/4 0.4 × 20 mm | DN Co. 27G 38 mm | TERUMO 27Gx3/4 0.4 × 20 mm | DN Co. 27G 38 mm |
| 5 mm/min | 13.50 | 16.52 | 22.68 | 16.09 | 7.58 | 10.32 | 26.88 | 35.38 |
| 15 mm/min | 18.07 | 21.15 | 23.53 | 24.98 | 10.72 | 13.82 | 28.57 | 39.66 |
| 30 mm/min | 24.50 | 25.90 | 29.57 | 26.27 | 13.36 | 17.62 | 32.03 | 41.66 |

The measurement results show that the Test Product can be injected under the skin with a less force than the Control Product (Ellanse™ M), i.e., the test product requires less injection force and provides a more consistent control of the injection force than the Control Product (Ellanse™ M).

[Test Example 6] Durability & Migration Test of the Microspheres for Use in Medical Fillers Medical fillers should preferably be provided with a sufficient durability to maintain the supporting force after being injected under the skin. Thus, the volume change of the Test Product, i.e., the microspheres of Product Example 2 and the Control Product, i.e., Ellanse™ M, against the time was measured and compared using PRIMOSLITE (with Software PRIMOS 5.8). In addition, the volume change against the time were measured and compared for other Control Products, i.e., Restylane® (Perlane+Lido) and AestheFill® (V200) after being injected under the skin.

Figure 61:
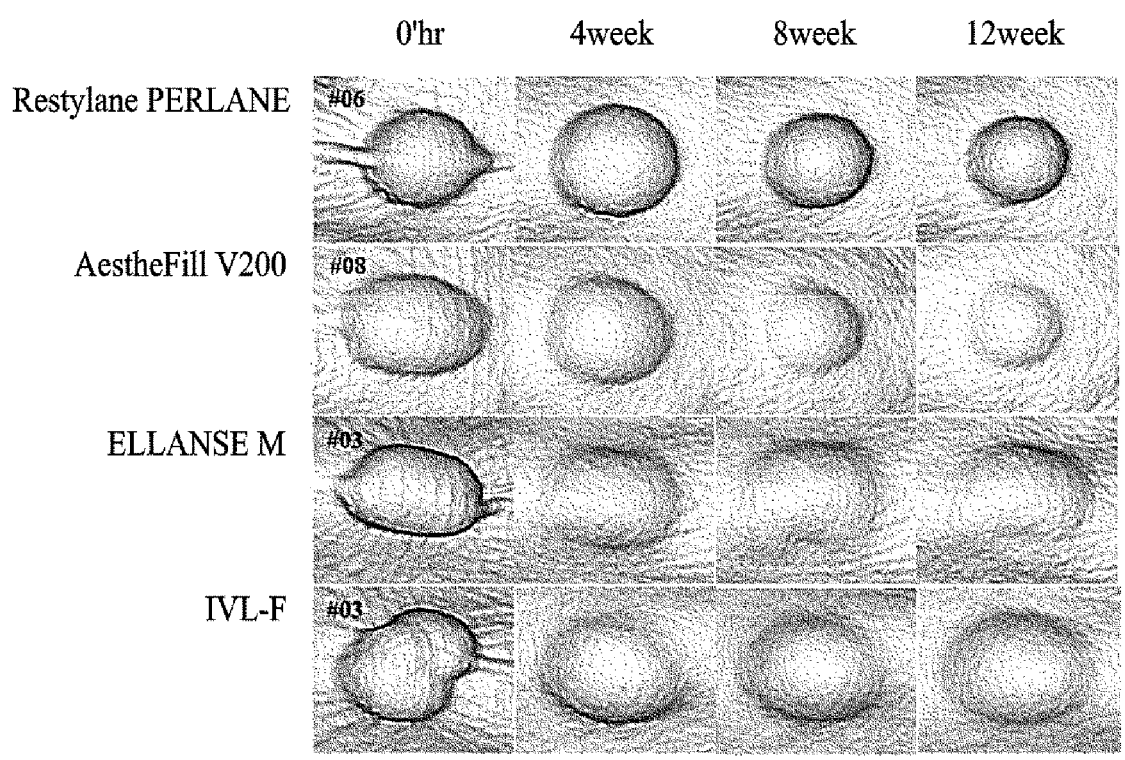
FIG. 61 illustrates SEM images illustrating the Change in Volume of IVL-F_180530, Restylane® Perlane+Lido, AestheFill® V200 and ELLANSE™ M after being injected into laboratory mice.

FIG. 61 is a photograph showing the volume changes in the microspheres of Product Example 2, i.e., Product Example 2 (IVL-F) and other Control Products against the time after being injected under the skin of the laboratory mice.

According to the results obtained, the Test Product is provided with a longer intradermal persistence period than the Control Product (Ellanse™ M).

[Test Example 7] Preparation of the Microspheres for Use in Medical Fillers: Biological Stability Evaluation As a preparation for the clinical test of the medical filler incorporating therein the microspheres produced, i.e, the

TABLE 12

Results of the Biological Stability Evaluation of the Test Product

| Test Items | Result | Evaluation | Test Method |
| --- | --- | --- | --- |
| Cytotoxicity Test (Indirect contact method-agar diffusion method) | Grade 0 (Noncytotoxic) | Suitable | Test according to ISO 10993-5, Cytotoxicity Test (Indirect Contact-Agar Diffusion Test). (Tested with undiluted solution) |
| Pyrogenicity Test | No NZW rabbit under test showed a rise in body temperature by 0.5° C. or higher in the pyrogenicity test, which evaluated the agent as a negative pyrogenic substance. | Suitable | ISO 10993-11, Pyrogenicity Test. (Prepare the sample solution: 4 g/20 mL, centrifuge at 3,000 rpm for 10 min at 37° C. for 72 h, filter through a 0.45 μm filter and use as the sample solution) |
| Intradermal Reaction Test | No NZW rabbit under test was observed to have erythema and edema in intradermal reaction test. Calculated difference between the test and control agents was less than "1.0". | Suitable | Test according to ISO 10993-10 Intracutaneous Reactivity test. |
| Acute Toxicity Test | No systemic toxicity change among ICR mice under test was observed within 72 hours after injection. | Suitable | Test according to ISO 10993-11 Acute systemic toxicity. (Administration route: abdominal cavity) |
| Genotoxicity Test (Microbial Return Mutation) | Negative | Suitable | Test according to ISO 10993-3, Test for genotoxicity. |
| Genotoxicity Test (Micronucleus test) | Negative | Suitable | Test according to ISO 10993-3, Test for genotoxicity. |
| Skin Sensitization | Sensitization test results of this agent against Dunkin | Suitable | Test according to ISO 10993-10, Maximization sensitization test. |

TABLE 12-continued

Results of the Biological Stability Evaluation of the Test Product

| Test Items | Result | Evaluation | Test Method |
|---|---|---|---|
| Test (Maximization method) | Hartley guinea pig were evaluated as weak in sensitization because it did not cause a skin reaction. | | |
| Subchronic Toxicity Test including Transplantation (90 days, transplant) | No significant systemic toxicity change was observed in all SD rats test group for 90 days after transplant compared with the control group. The histological evaluation indices of the test transplantation site were calculated as zero in both male and female groups compared with the control group, which evaluated both male and female group as "non-irritant." | Suitable | Test according to ISO 10993-11, subchronic systemic toxicity of Test for systemic toxicity and ISO 10993-6, Test method implantation in subcutaneous tissue. (90 days, undiluted solution, subcutaneous transplantation) |
| Aseptic Test | Suitable | Suitable | Test according to Aseptic Test Method in General Test Methods of the Korean Pharmacopoeia. | wherein, the infusion solution is in accordance with [Common Standard for Biological Safety of Medical Devices] or ISO 10993.

Based on the results of the biological stability evaluation, it can be concluded that the Test Product has achieved/met all of the required biological stability requirements.

Biodegradable Microspheres Developed for Use in Heartworm Preventives

The *Dirofilaria Immitis*, also known as Heartworm, is a parasite that is transmitted mainly by mosquitoes and detrimentally affects the heart of pets such as dogs and cats. When infected, it eradicated with an arsenic agent (caparsolate) or with melarsomine. However, all of the above therapeutic agents above have serious side effects such as irritation at the injection site and liver/kidney damages.

Therefore, it is safe and economical to prevent the Heartworm disease before being infected and Diethylcarbamazine (DEC), Ivermectin, Milbemycin, Moxidectin, Selamectin, etc. are known to prevent the Heartworm disease.

These preventive medicines should be given on a daily-basis or monthly intervals to ensure adequate preventive effects, but if the prescribed medication period is not properly kept, the preventive effect may disappear, exposing the pets to the risk of Heartworm infection.

Thus, the inventors have attempted to mass produce, using the basic principles and the apparatus in accordance with the present invention which are ideally suited for the mass production of polymeric DDSs as described above, biodegradable polymer-based microspheres, uniformly dissolved therein one of the Heartworm preventive agents above to be slowly released into the body as the biodegradable polymer in the microsphere degrades after being injected, similar to how polymeric DDSs function in human body.

The microspheres, including therein one of the preventive agents above, for use in Heartworm preventives in accordance with one embodiment of the present invention are to be administered through the syringe into the subject's skin, maintaining the effectiveness for a prolonged period of three to six months, the period coinciding with the degradation period of the biodegradable polymer. In addition, since the mass production apparatus according to the present invention is capable of mass producing monodisperse biodegradable polymer-based microspheres dissolved therein one of the Heartworm preventive agent, the Heartworm preventive incorporating therein the microspheres of the present invention, as a consequence of the monodispersity of the microspheres, can maintain the intended drug delivery rate, coinciding with the degradation rate of the biodegradable polymer and the drug effectiveness period constant, coinciding with the polymer degradation period. In addition, using the basic principles and the apparatus developed in accordance with the present invention, the biodegradable polymer-based microspheres for use in Heartworm preventives can be produced at a high yield, as observed for Medical Fillers above.

The microspheres for use in the Heartworm preventive mass produced in accordance with the present invention for use in Heartworm preventive are spherical in general and include therein a Heartworm preventive agent evenly distributed in a biodegradable polymer.

In one embodiment, the average diameter of the microspheres is from about 80 μm to about 130 μm. In another embodiment of the present invention, since Heartworm preventive incorporating therein the microspheres is to be injected into an animal such as a dog or a cat, not into a human, the microspherical product for prevention of *Dirofilaria Immitis* infestation is injected into an animal such as a dog or a cat and is not injected into a human, pain or foreign body sensation during injection may not be an issue. Accordingly, it is advantageous to make the biodegradation period of the microspheres for use in Heartworm preventives as long as possible with a view to carrying out Heartworm preventive function as long as possible, and, hence, the microspheres for use in Heartworm preventives are relatively be larger than the microspheres for use in other medical products to be injected into the human body.

Figure 62:
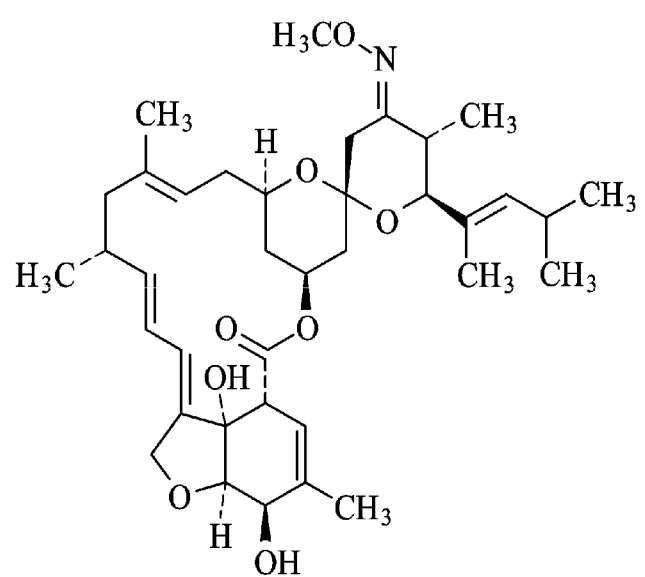
FIG. 62 illustrates Chemical Formula/Structure of Moxidectin.

In one embodiment of the present invention, Moxidectin is used as the Heartworm preventive agent and there is shown in FIG. 62 the chemical formula and structure thereof.

In one embodiment, the microspheres of the present invention may comprise a biodegradable polymer and Moxidectin in a weight ratio of 4:1 to 9:1, preferably 4:1. When the weight ratio of the biodegradable polymer and the moxidectin is less than 4:1, the shape-retaining force of the biodegradable polymer may be weakened, possibly resulting in an uneven distribution of Moxidctin and the biodegradable polymer in the microspheres. In addition, if the weight ratio of the biodegradable polymer and the moxidectin exceeds 9:1, a considerable amount of heartworm preventive should preferably be administered to the subject, which may cause discomfort to the subject. More specifically, the concentration of the biodegradable polymer in the biodegradable polymer-phase solution should be between 15 wt % and 60 wt %, preferably 15 wt %, but is not limited to the above example.

In one embodiment, the microspheres of the present invention may continuously release Moxidectin in the body for three to six months.

In one embodiment, the biodegradable polymer of the present invention may be selected from the group consisting of polylactic acid, polylactide, polylactic-co-glycolic acid, polylactide-co-glycolide (PLGA), polyphosphazene, polyiminocarbonate, polyphosphoester, polyanhydrides, polyorthoesters, polycaprolactones, polyhydroxyvalates, polyhydroxybutyrates, polyamino acid, and combinations thereof.

In one embodiment, the microspheres of the present invention are prepared by using the basic droplet-based HCMMM microsphere manufacturing method described above with reference to FIG. 2, wherein the mixture is properly mixed/dissolved in the biodegradable polymer-phase solution.

In another embodiment, the microspherical products of the present invention are formed using the mass production apparatus described with reference to FIGS. 16 to 31.

[Manufacturing Example]—Preparation of Microspheres Including Moxidectin for Use in Heartworm Preventives The diameter of the microspheres for use in Heartworm preventive to be subcutaneously injected into the animal is set between 80 μm and 130 μm, preferably set to be 100 μm, considering the biodegradation period, drug delivery rate and injectability of the Heartworm preventive including therein the microspheres, and the concentration of biodegradable polymer and Heartworm preventive agent, i.e., moxidectin, was set as follows.

The biodegradable polymer phase solution was prepared by dissolving polylactide-co-glycolide (PLGA) and Moxidectin in an organic solvent, i.e., dichloromethane. The concentration of the biodegradable polymer, i.e., PLGA, in the biodegradable polymer-phase solution was set at 15 wt % and the weight ratio of PLA to Moxidectin was set at 4:1.

The water-phase solution was prepared by dissolving Polyvinyl alcohol (PVA) as a surfactant in pure water with water at a concentration of 0.25 wt %.

In one of the side, e.g., the width, of the microchannels in the multichannel microsphere forming unit 100 was set at 100 μm.

The water-phase solution and biodegradable polymer-phase solution were introduced into the microchannels formed on a silicon wafer. The flow rate of the water-phase solution was adjusted while holding the flow rate of the biodegradable polymer-phase solution constant until the diameter of the microspheres formed reaches the target diameter, i.e., 100 μm.

Then, the flow rate of the biodegradable polymer-phase solution was adjusted while holding the flow rate of the water-phase solution constant to fine-tune the diameter of the microspheres obtained from the above described procedure.

Referring to FIG. 16, the flow rate of the water-phase solution and the flow rate of the biodegradable polymer-phase solution are adjusted by controlling the flows from the first reservoir 300 and the second reservoir 400 to the multichannel microsphere forming unit 100 using the flow rate control unit 200.

The water-phase solution and biodegradable polymer-phase solution were maintained at a temperature of 15° C.

The microspheres formed in the product reservoir 600 (see FIG. 16) were collected to be stirred. There are three stirring stages. The first stage stirring was carried out at a speed of 300 rpm for 1 hour at 17° C., followed by the second stage stirring, at a temperature of to 25° C., at a speed of 400 rpm for 1 hour and finally, the third stage stirring, a temperature of 45° C. at a speed of 500 rpm for 4 hours.

The desired microspheres were obtained by washing several times the microspheres that underwent the three stirring stages with purified water and by lyophilizing the microspheres that underwent the washing stages.

[Comparative Example]—Heartworm Preventives

As a comparative example, a commercial available Heartworm preventive, namely, Proheart® SR-12 was used.

[Test Example 1] SEM Image Analysis of the Microspheres for Use in Heartworm Preventives The morphology of the Control Product, i.e., commercially available Proheart®, and the Test Product, i.e., the microspheres for use in Heartworm Preventives in accordance were analyzed and compared using SEM images thereof.

Figure 63:
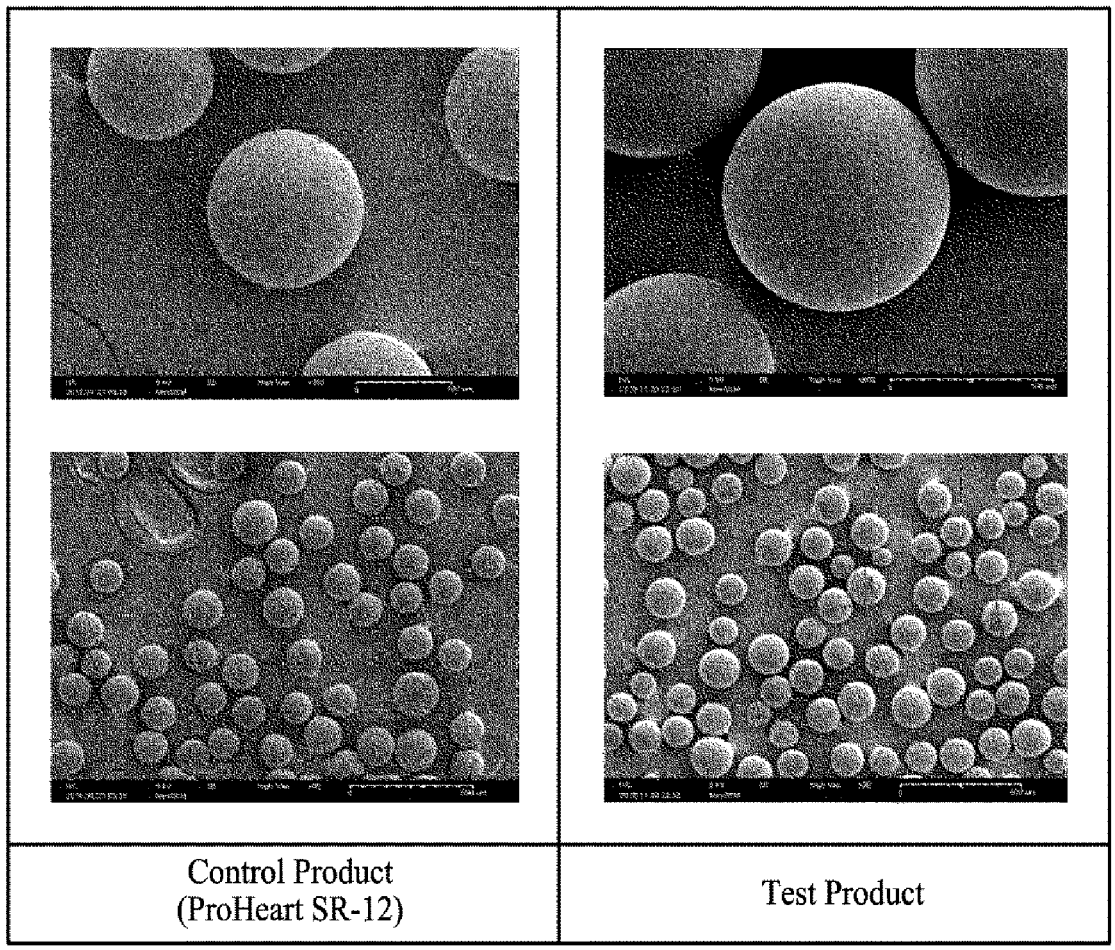
FIG. 63 illustrates a comparison of SEM Image Comparison of the Control Product (ProHeart SR-12) and the Test Product (DOP-02).

FIG. 63 is a comparison of the SEM images of the microspheres for use in Heartworm Preventives manufactured using the mass production apparatus and the basic principles in according with the present invention, i.e., the Test Product, and the SEM images of the microspheres incorporated in the Control Product, i.e., Proheart®.

Based on the analysis of SEM images of the microspheres of the Test Product, i.e., the microspheres obtained using the principles and the mass production apparatus of the present invention, and the microspheres incorporated in the Control Product, i.e., Proheart®, it can be concluded that the microspheres of Test Product have a spherical shape comparable to that of the Control Product.

Further, the microspheres of the Test Product have a smoother shape than the microspheres of the Control Product and the overall size distribution thereof is relatively constant, i.e., are monodispersed.

[Test Example 2]—Size Distribution Analysis of the Microspheres of the Test Product and the Control Product The diameters of the microspheres of the Control Product, i.e., Proheart® and the Test Product, were compared and analyzed using a particle size analyzer (PSA).

Figure 64:
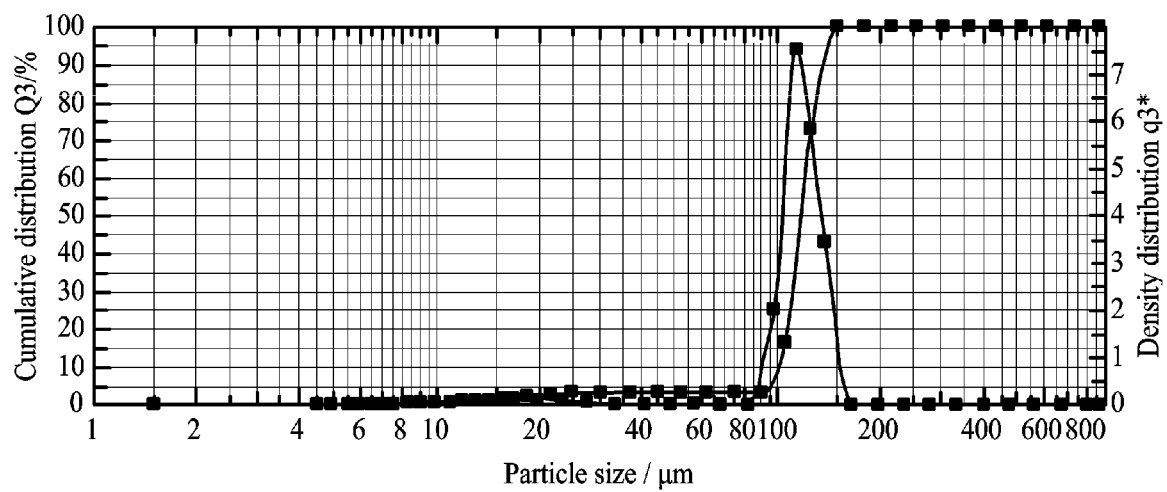
FIG. 64 illustrates a Size Distribution Analysis of the Control Product (ProHeart SR-12) and the Test Product (DOP-12).

There is shown in FIG. 64 a graph illustrating the results of the particle size analysis of the microspheres of the Test Product and the Control Product and Table 12 is a summary thereof.

According to the analysis, the Test Product was analyzed to have a smaller mean diameter and also a narrower distribution compared to the Control Product, implying that the Test Product can be injected into the animal using a high G (gage) needle having a narrower inner diameter, i.e., a higher injectability compared to the Control Product.

TABLE 12

Summary of the Size Distribution Analysis of the Microspheres of the Test Product and the Control Product

| Product | $X_{10}(\mu m)$ | $X_{50}(\mu m)$ | $X_{90}(\mu m)$ | SMD(μm) | VMD(μm) |
|---|---|---|---|---|---|
| Control Product (ProHeart SR-12) | 110.50 | 132.48 | 148.62 | 130.39 | 131.91 |
| Test Product | 98.09 | 116.93 | 140.77 | 99.37 | 116.01 |

[Test Example 3]—Content Test of the Microspheres for Use in Heartworm Preventives Table 13 describes the test items and methods used for the content test. The Test Product was tested for the contents according to the procedure as described in Table 13.

TABLE 13

| Content Test Method | |
| --- | --- |
| Standard Solution | 0.1 g of Standard Moxidectin was dissolved in Acetonitrile to obtain 10 ml of Acetonitrile Solution. The Standard Solution was obtained by adding acetonitrile to 1 ml of Acetonitrile Solution until the volume thereof reaches 10 ml. |
| Test Solution | Dissolve 1 g of the microspheres in Acetonitrile until the volume reaches 10 ml. Use this solution as the Test Solution. |
| Formula | Peak Area of the Test Solution/Peak Area of the Standard Solution × Content of Standard Moxidectin × 100 |

The content was calculated as a product of the Test Solution Peak Area divided by the Standard Solution Peak Area and multiplied by the Content of Standard Moxidectin multiplied and by 100.

According to the results of the test, the content of Moxidectin in the Test Product was measured to be 96.26% (±0.25%), meaning that the Moxidectin content of the Test Product was analyzed to be within the normal drug content range of 95.0 to 105.0%.

[Test Example 4]—Release Test of the Microspheres for Use in Heartworm Preventives Table 14 describes the test items and methods for the release test of the microspheres for use in Heartworm Preventives. The release test of the Test Product was carried out according to the procedure as described in Table 14

TABLE 14

| Release Test Method | |
| --- | --- |
| Release Test solution | 0.9% SLS |
| Release Test Method | 1. Fill 100 mg of this product in a 120 ml glass test container filled with 100 ml of the release test solution<br>2. Place it in a 37° C. water bath and shake it with a vibration amplitude 4 cm and a shaking frequency 120 times/minute (reciprocation)<br>3. Shake well before taking 1 ml of specimens when collecting.<br>4. Run centrifuge at 13,000 rpm for 3 minutes, take the supernatant and analyze by HPLC<br>(Analyze by HPLC after filtering using 0.45 μm PTEF syringe filter) |
| Release Temperature | 37° C. |
| Paddle rpm | 120 rpm |
| Sampling Time | 15, 30 min, 1, 2, 4, 8 hr, 1, 2, 3, 4, 7, 10, 14 day |

Figure 65A:
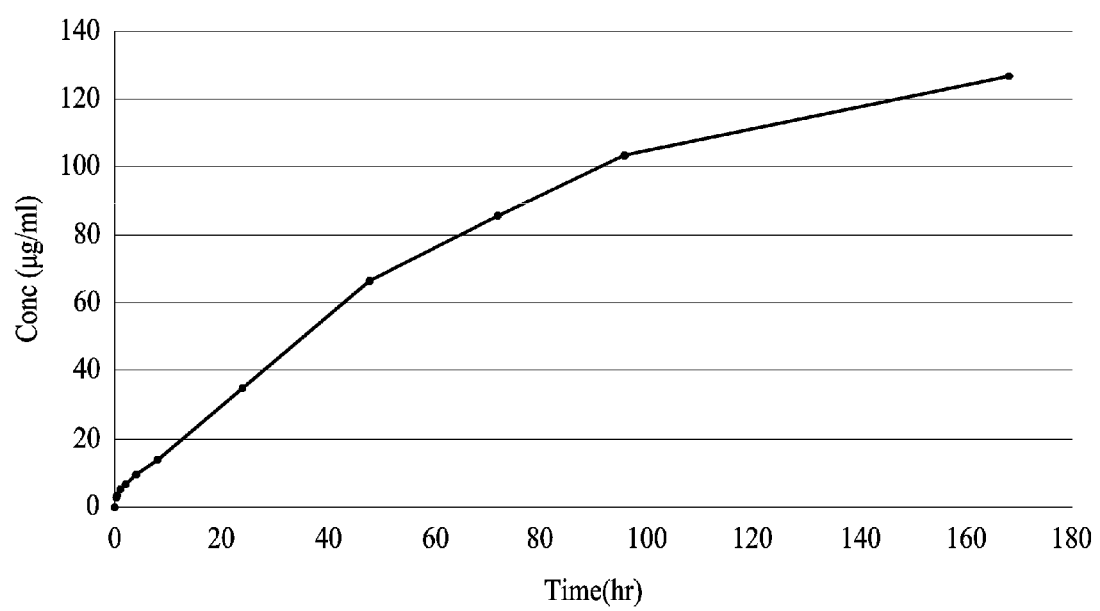
FIGS. 65A and 65B illustrate a Release Test of the Control Product (ProHeart SR-12) and the Test Product (DOP-02).
Figure 65B:
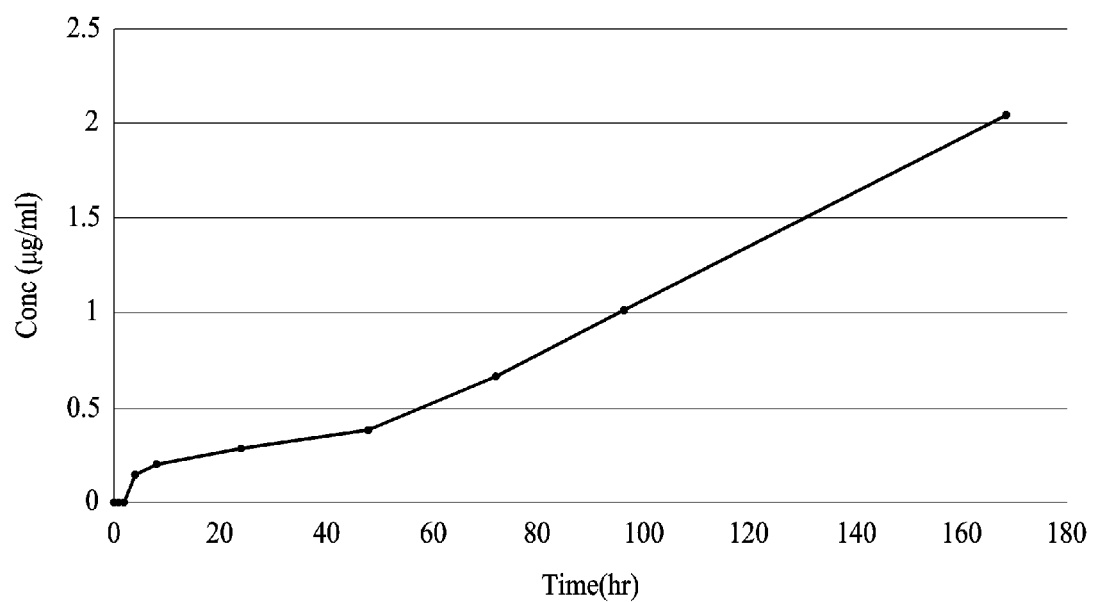

There are shown in FIGS. 65A and B the result of the in vivo release test of the control product (ProHeart® SR-12) and that of the Test Product, respectively.

According to the body release test, the total amount of drug released in the body increased with time in the Control Product and the Test Product, and both showed similar overall results.

In this graphs, the drug delivery rate will be the slope of the drug release over time. The Control Product showed a decrease in drug delivery rate near the final release stage, whereas the Test Product was found to maintain a constant slope, that is, a constant drug delivery rate even after a long period of release, showing a clear advantage over the Control Product.

[Test Example 5] Morphology Variation of the Microspheres for Use in Heartworm Preventives with Respect to the Concentration of the Biodegradable Polymer (PLA) Therein The morphological changes of the microspheres were observed as the concentration of the biodegradable polymer (PLA) therein was varied, from 40 wt % to 50 wt % and finally to 60 wt %.

Figure 66A:
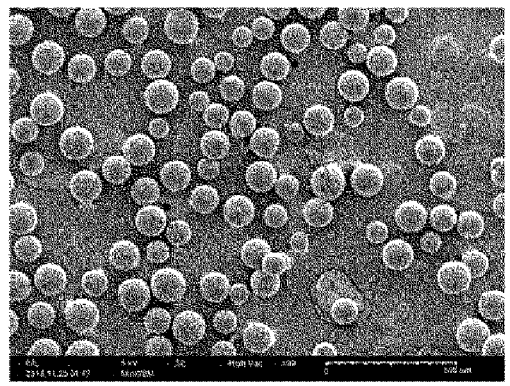
Figure 66B:
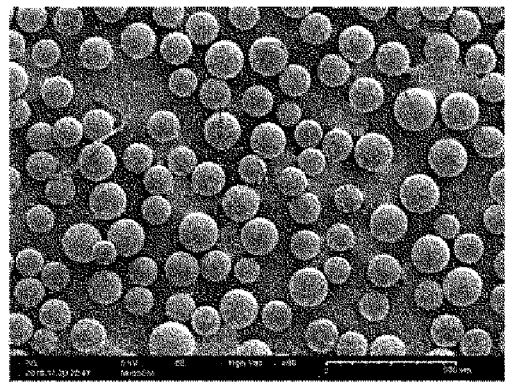
Figure 66C:
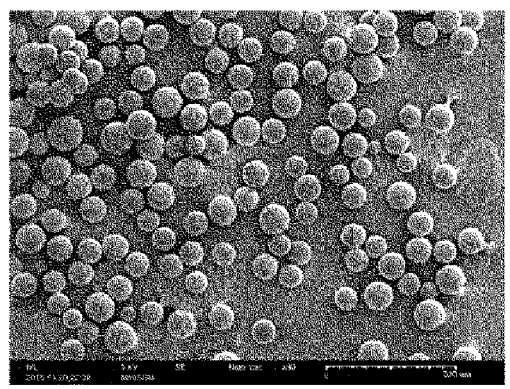

There are shown in FIGS. 66A to C an SEM image when the concentration of the biodegradable polymer (PLA) is 40 wt %, when the concentration of the biodegradable polymer is 50 wt % and when the concentration of the biodegradable polymer is 60 wt %, respectively.

It was confirmed through the observation that as the concentration of the biodegradable polymer, which functions as the skeleton in the microspheres incorporating therein Moxidectin and biodegradable polymer, increases, microspheres having more perfect spherical shape and a smoother surface are obtained.

[Test Example 6]—Analysis of the Particle Size Distribution of the Microspheres for Use in Heartworm Preventives as the Concentration of the Biodegradable Polymer (PLA) is Varied The particle size distribution of the microspheres of the Test Product were analyzed using a particle size analyzer (PSA) as the concentration of the biodegradable polymer (PLA) therein were varied, from 40 wt % to 50 wt % and finally to 60 wt %.

Figure 67A:
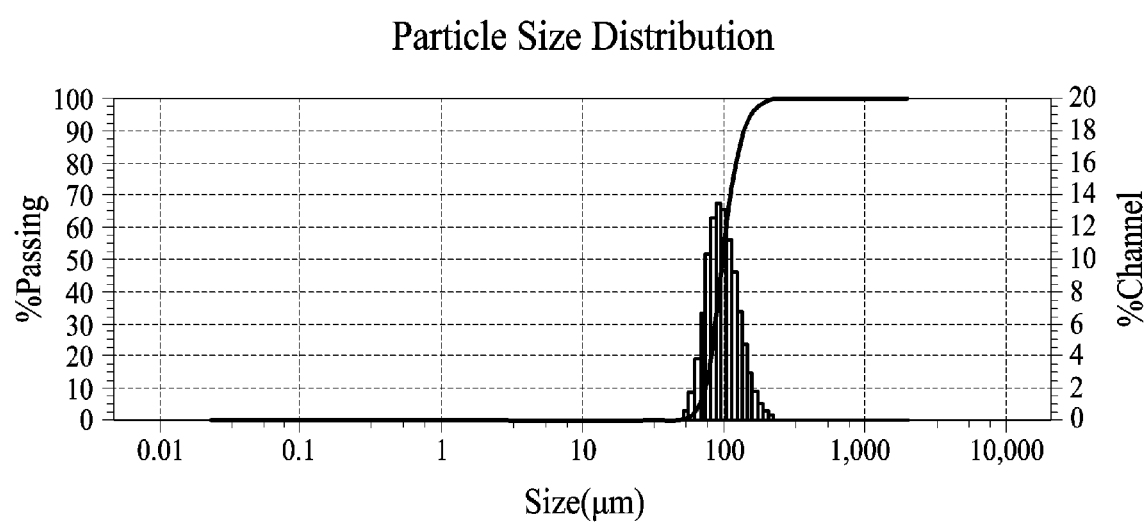
FIGS. 67A to 67C illustrate a Size Distribution Analysis of the Test Product (DOP-12) incorporating therein the biodegradable polymer (PLGA) at a concentration of 40 weight %, 50 weight % and 60 weight %, respectively.
Figure 67B:
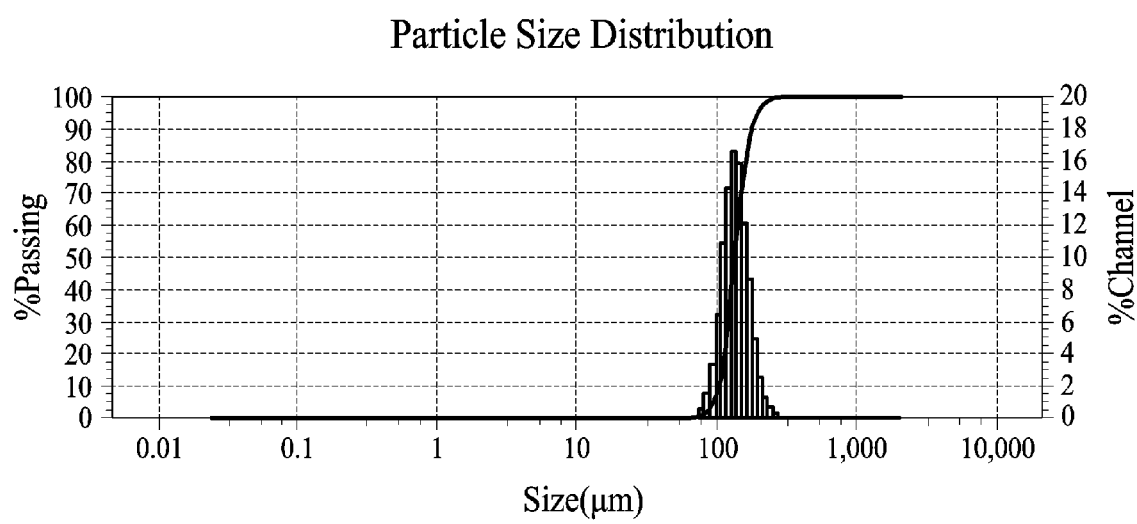
Figure 67C:
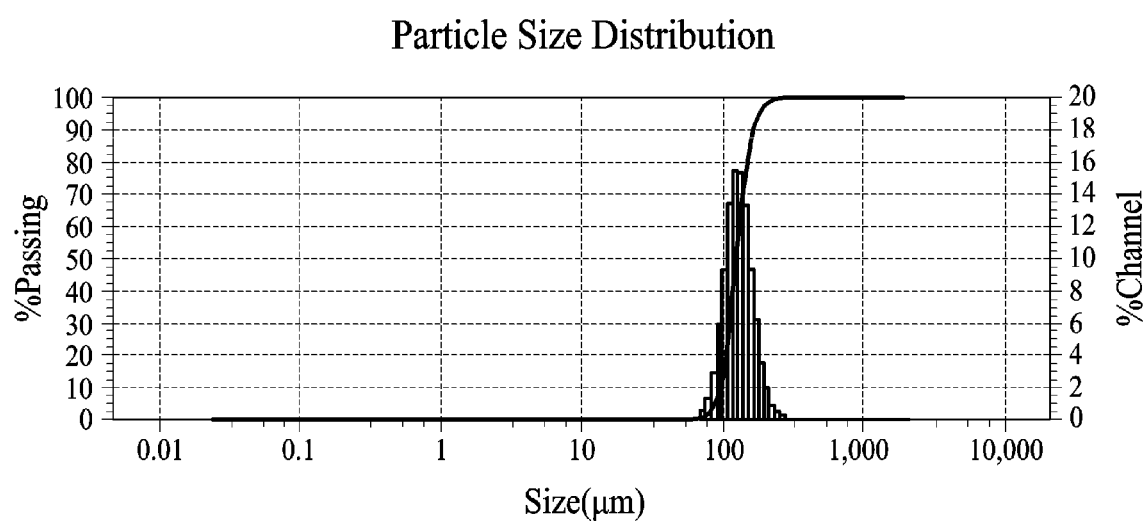

There are shown in FIGS. 67A to C, a graph of the particle size analysis when the concentration of the biodegradable polymer of the Test Product is 40 wt %, when the concentration of the biodegradable polymer of the Test Product is 50 wt % and when the concentration of the biodegradable polymer of the test product is 60 wt %, respectively.

Referring to FIG. 67A, the Test Product had an average diameter of 133.2 μm and was analyzed to have a diameter distribution of 56.43 μm centered on the average diameter.

Referring to FIG. 67B, the Test Product had an average diameter of 125.3 μm and was analyzed to have a diameter distribution of 55.77 μm centered on the mean diameter.

Referring to FIG. 67C, the test product has an average diameter of 96.69 μm and was analyzed to have a diameter distribution of 50.97 μm centered on the mean diameter.

According to the results of the particle size distribution analysis, the diameter of the prepared microspheres decreased as the concentration of the biodegradable polymer increased, and was analyzed to have a narrow diameter distribution in the range of 50 μm to 60 μm.

[Test Example 7]—Drug Release Test for the Microspheres for Use in Heartworm Preventives as the Concentration of the Biodegradable Polymer (PLA/PLGA) Therein is Varied The in vivo drug release test for the microspheres was carried out the concentration of the biodegradable polymer (PLA) of the Test Product was varied from 40 wt %, 50 wt % and finally, 60 wt %.

Figure 68A:
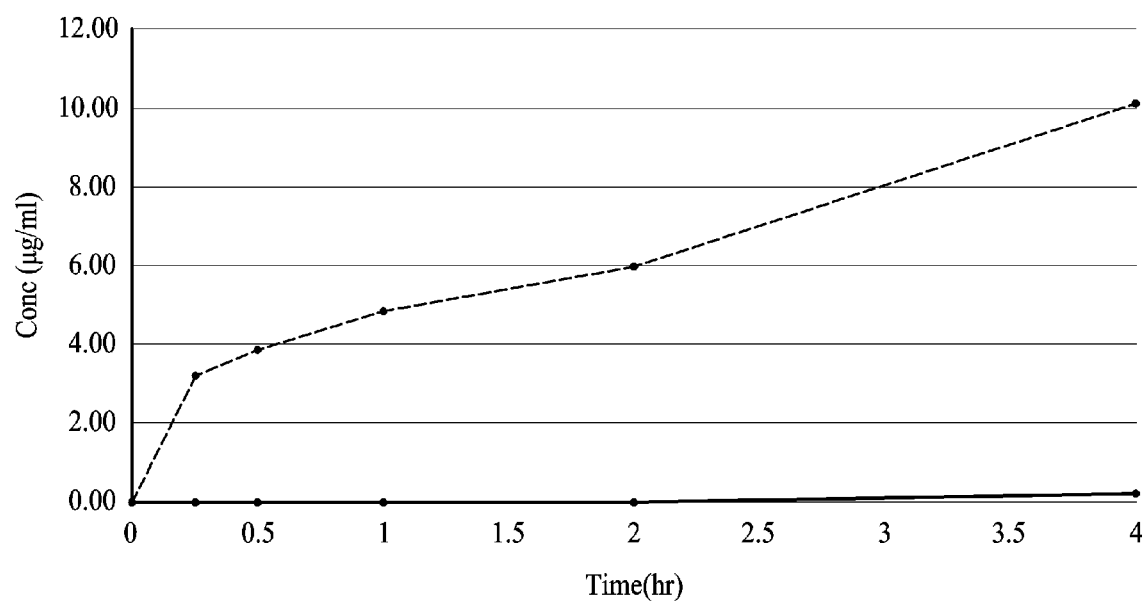
FIGS. 68A to 68C illustrate Release Tests of the Test Product (DOP-12) incorporating therein the biodegradable polymer (PLGA) at a concentration of 40 weight %, 50 weight % and 60 weight %, respectively.
Figure 68B:
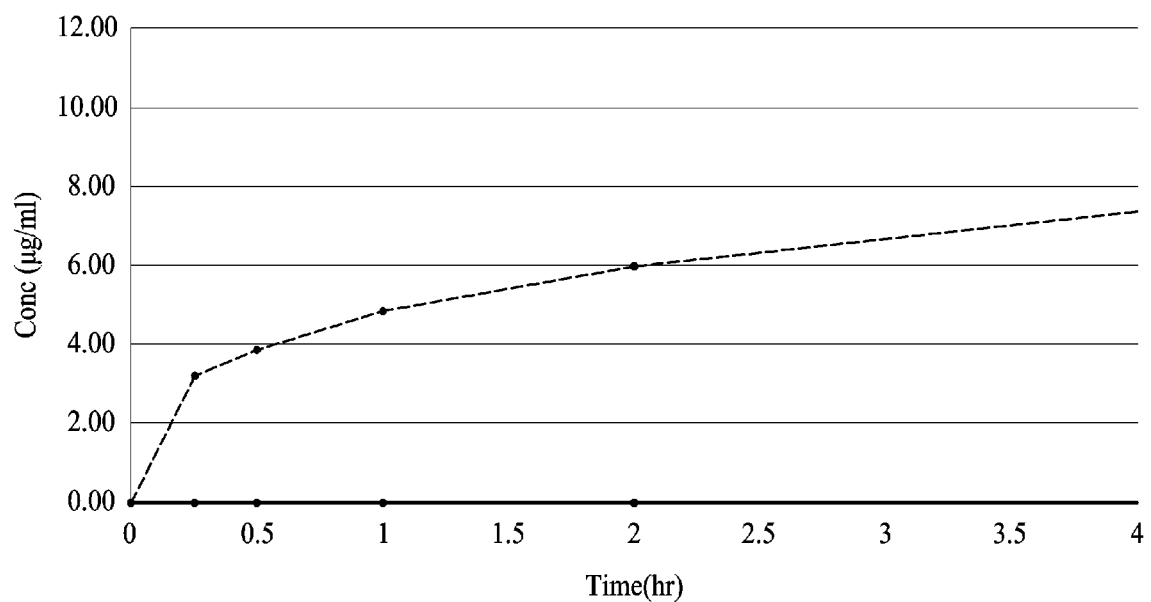
Figure 68C:
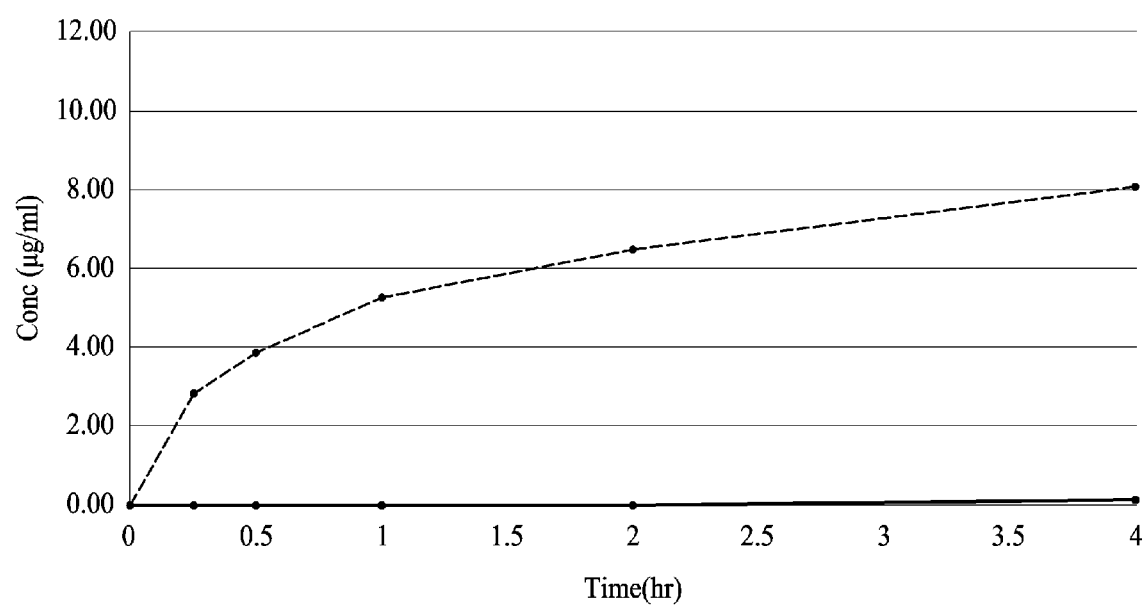

There are shown in FIGS. 68A to C, a graph of the drug release test results when the concentration of the biodegradable polymer of the Test Product is 40 wt %, when the concentration of the biodegradable polymer of the Test Product is 50 wt % and when the concentration of the biodegradable polymer of the test product is 60 wt %, respectively.

According to the drug release test results of the microspheres as the concentration of the biodegradable polymer therein was varied, the concentration of biodegradable polymer in the microspheres has a relatively small effect on the drug release. If a different drug release profile is desired, a different type or combination of the biodegradable polymers may be attempted.

Thus, microspheres incorporating therein PLGA (DL-lactide/glycolide copolymer, PURAC®), which is based on PLA (poly (DL-lactide), PURAC®) polymer with glycolide added thereto to shorten the polymer degradation period, was further tested.

[Test Example 8] Morphology Variation in the Microspheres for Use in Heartworm Preventives According to the Mixing Ratio of the Biodegradable Polymer (PLGA) to Moxidectin The morphological changes in the microspheres were observed as the mixing ratio of moxidectin to the biodegradable polymer (PLGA) was varied from 1:9, to 1:6 and, finally to 1:4.

Figure 69A:
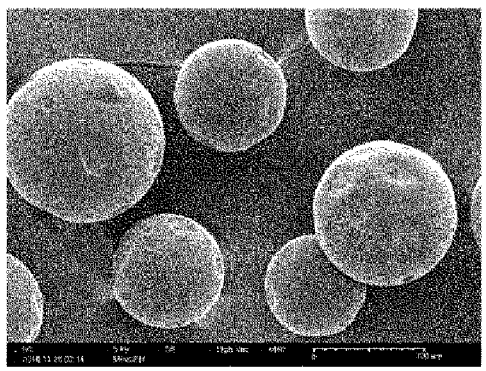
FIGS. 69A to 69C SEM illustrate images of the Test Product (DOP-12) incorporating Moxidectin and the biodegradable polymer (PLGA) at a ratio of 1:9, 1:6 and 1:4, respectively.
Figure 69B:
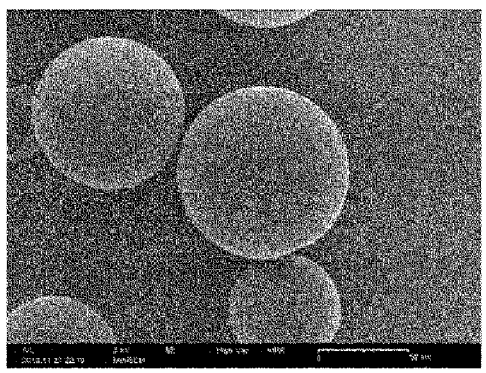
Figure 69C:
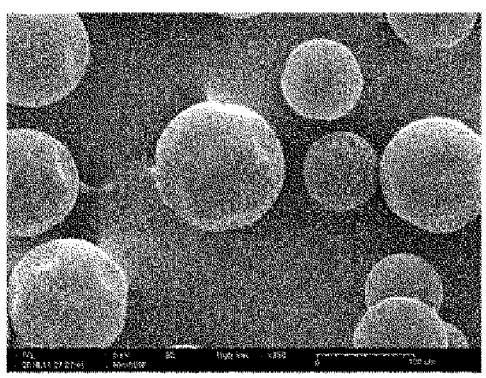

There are shown in FIGS. 69A to C an SEM image of the microspheres when the ratio of moxidectin to the biodegradable polymer (PLGA) is 1:9, the same when the ratio of moxidectin to the biodegradable polymer (PLGA) is 1:6, and the same when the ratio of moxidectin to the biodegradable polymer (PLGA) is 1:4, respectively.

According to the SEM images of the microspheres incorporating therein PLGA as the biodegradable polymer, density of the microspheres decreased as the ratio of the heartworm preventive agent/drug to PLGA polymer increased, and the rate or amount of drug release should increase as the density of the microspheres decreases.

[Test Example 9] In-Vivo Drug Release Test of the Micropsheres for Use in Heartworm Preventives as the Mixing Ratio of the Biodegradable Polymer (PLGA) to Moxidectin Changes The in vivo drug release tests were performed the microspheres to be used in Heartworm Preventives as the ratio of the heartworm preventive agent/drug, i.e., moxidectin, to the biodegradable polymer (PLGA) is varied from 1:9, to 1:6 and finally to 1:4.

Figure 70:
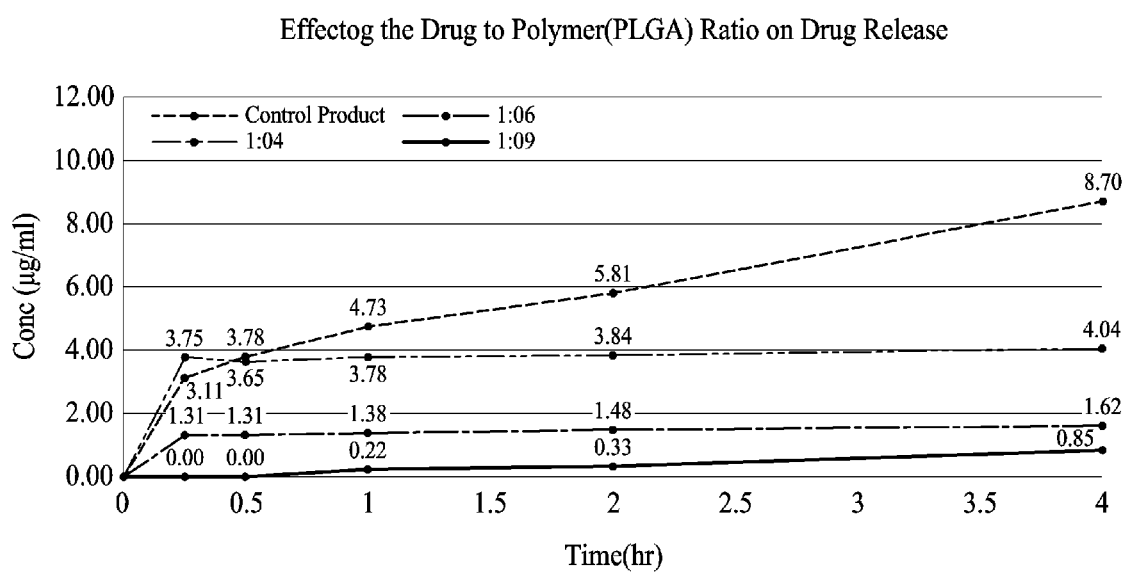
FIG. 70 illustrates Release Test Results (in-vitro) of the Test Product (DOP-12) incorporating therein Moxidectin and the biodegradable polymer (PLGA) at a ratio of 1:9, 1:6 and 1:4, respectively.

FIG. 70 is a graph of the in vivo drug release results of the Test Product while varying the mixing ratios of the heartworm preventive agent/drug, i.e., moxidectin, and the biodegradable polymer (PLGA).

Compared with the Control Product, the Test Products having a variety of mixing ratio of moxidectin and biodegradable polymer (PLGA) have exhibited shorter in vivo release periods and smaller release amount. However, this is due to the biodegradation period of the Test Product was designed to be short, and it was confirmed that the drug release amount can be increased by increasing the mixing ratio of the heartworm preventive agent/drug, i.e., moxidectin, to the biodegradable polymer, i.e., PLGA.

[Test Example 10]—Test of the Heartworm Preventive Developed Incorporating Therein the Microspheres of the Present Invention on Animals Testing of the Test Product was carried out on animals. As the first step, a test plan was prepared.

The purpose of the animal testing is for the pharmacokinetic evaluation of the Test Product, that is, the mass-produced microspheres for use in Heartworm Preventives in accordance with the present invention and the Control Product, i.e., ProHeart® SR-12.

Pharmacokinetic parameters of moxidectin are provided in Table 15 below.

TABLE 15

| Pharmacokinetic Parameter of Moxidectin | |
|---|---|
| Pharmacokinetic Parameters | Value |
| AUC | 217 ng. day/mL |
| Cmax | 5.1 ng |
| Tmax | 7-10 day |
| T½ | 35 day |

The animal testing method was designed as follows:

1. Blood collections are conducted at 0, 1, 2, 6, 12 hours, 1, 3, 6, 7, 8, 9, 10, 14, 21, 28, 42, 56, 70 and 90 days;
2. Three groups are tested, each group consisting three specimen; and
3. Test group is composed as shown in the following Table 16.
4. The dosage was set based on the dosage (0.5 mg/kg) of the commercial Control Product (ProHeart® SR-12). The dosage of the Test Product was set at ¼ of the Control Product (0.125 mg/kg) proportional to the expected duration of the drug in the body (Control Product: 12-month release period and the Test Product: 3-month release period); and
5. The Control Product and the Test Product were administered once by subcutaneous injection, and the blood was collected from the jugular vein and analyzed for the concentration of Moxidectin in the blood using LC-MS/MS.

TABLE 16

| Configuration of the Test Group | | | | | |
|---|---|---|---|---|---|
| Group | Gender | Number of Animals | Animal Number | Dose | Drug |
| G1 | M | 3 | 1-3 | 0.125 mg/kg | Moxi-1Q |
| G2 | M | 3 | 4-6 | 0.5 mg/kg | ProHeart SR-12 |

TABLE 16-continued

| | | | Configuration of the Test Group | | |
|---|---|---|---|---|---|
| Group | Gender | Number of Animals | Animal Number | Dose | Drug |
| G3 | M | 3 | 7-9 | 2.5 mL (10-20 kg test group setting) | Advocate | wherein, Moxi-1Q refers to the Test Product

Figure 71A:
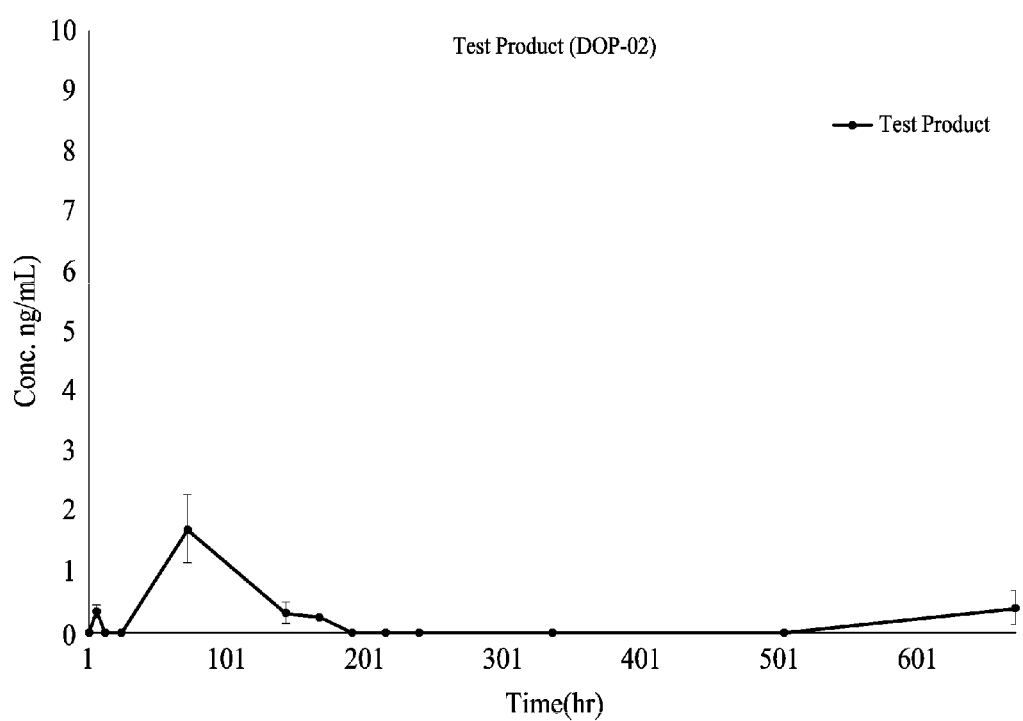
FIGS. 71A to 71C illustrate Release Test Results (laboratory animal) of the Test Product (DOP-2), the Control Product (ProHeart SR-12) and a Direct Comparison of the Release Test Results of the Test Product and the Control Product, respectively.
Figure 71B:
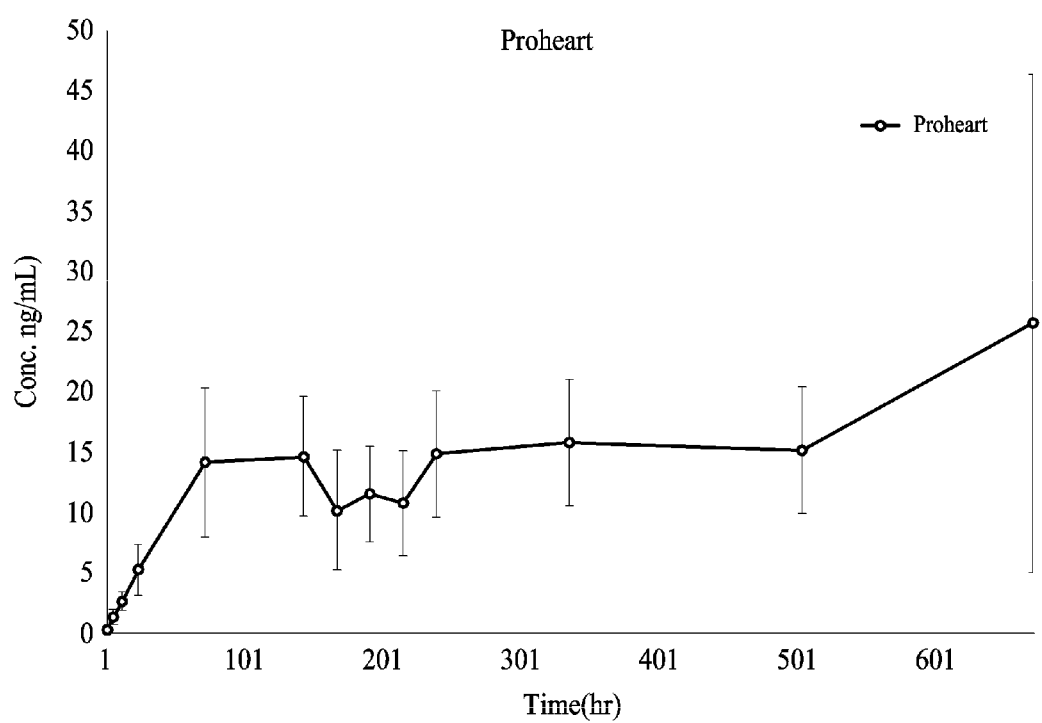
Figure 71C:
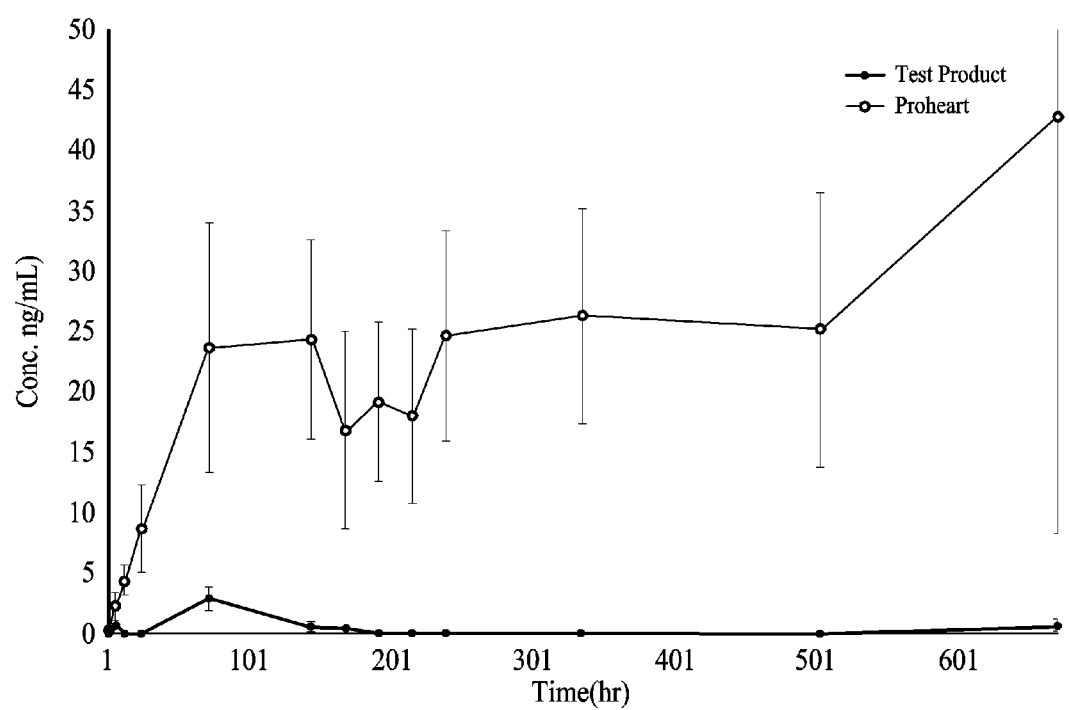

There are illustrated in FIGS. 71A to C a graph of the drug release results of the Test Product, a graph of the drug release results of the Control Product (ProHeart® SR-12) and a combined graph of the drug release results of the Test Product and the Control Product.

According to the drug release results, the primary PK test of the Control Product (ProHeart® SR-12) and the Test Product showed a slight difference in blood concentration. Since, however, these differences can be overcome by varying the dosage of the heartworm preventive or by increasing the concentration of the preventive agent/drug therein, it can be concluded that the Test Product has a drug efficacy comparable to that of the Control Product.

Microspherical Products Developed for Hair Loss Preventives

Figure 72:
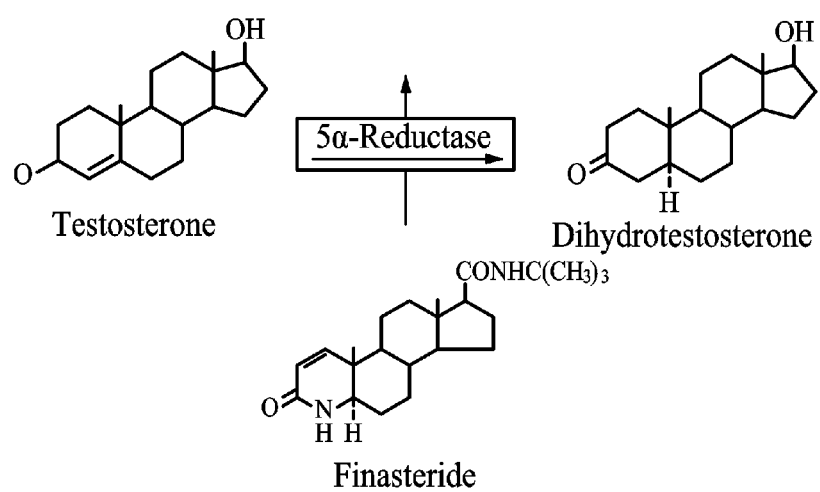
FIG. 72 illustrates the effect of Dutasteride and Finasteride on Testosterone.

There are two types of commercially available oral therapeutic agents for preventing hair loss, namely, finasteride or dutasteride. These hair loss treatments using these therapeutic agents, as shown in FIG. 72, inhibit 5-α-reductase inhibitor which acts to convert testosterone into dihydrotestosterone (DHT), which is a strong male hormone, thereby inhibiting DHT production, which, in turn, inhibits the shrinking of hair root by DHT at the scalp, thereby treating androgenetic hair loss.

5-α-reductase inhibitors can be divided into Type 1 and Type 2. Type 1 is found in the scalp and sebaceous glands, and Type 2 in the scalp and prostate. Finasteride only blocks Type 2 of the 5-α-reductase inhibitor, but dutasteride blocks both, Type 1 and Type 2 inhibitors. It is known that the dutasteride is more potent in inhibiting DHT than finasteride. However, based on the first year of use, the rate of side effects of dutasteride was higher, and as a consequence, finasteride, is now the most widely used and safe treatment for the hair loss, and is the only FDA approved drug therefor.

Such oral hair loss treatment drugs can only be effective when taken on a daily-basis for more than 3 months, making it extremely inconvenient for the patient.

The inventors have investigated the possibility of mass producing biodegradable polymer-based microspheres incorporating therein the hair loss preventive/therapeutic agent/drug using the basic principles and the apparatus developed in accordance with the present invention, capable of providing a controlled release of the hair loss therapeutic agent/drug in the human body as seen in the polymeric DDSs according to the present invention as described above.

The hair loss preventive incorporating therein the biodegradable polymer-based microspheres in accordance with present invention is administered through the syringe into the skin of the patient, allowing the hair loss preventive/therapeutic agent/drug included in the microspheres to be released into the body in a controlled manner, as the biodegradable polymer degrades, for an extended period of time, e.g., one to three months, depending on the drug design requirements. In addition, since it is possible to mass produce monodisperse biodegradable microspheres, i.e., microspheres having a narrow particle size distribution, through the use of the basic principles and the mass production apparatus according to the present invention, the duration and degree of the drug release of the drug can be controlled tightly, eliminating or greatly reducing the inconvenience associated with the oral intaking of hair loss preventive/therapeutic agent/drug on a daily-basis. In addition, the basic principles and the mass production apparatus of the present invention allow the mass production of monodisperse biodegradable polymer-based microspheres for use in hair loss preventives having a size close to the desired size possible with a high yield.

In one embodiment of the microspheres for use in hair loss preventives, wherein the microspheres include a hair loss treatment agent/drug and a biodegradable polymer, the microspheres are generally spherical with a uniformly distributed hair loss treatment agent/drug and biodegradable polymer therein. The average diameter of the microspheres is about 20 to 70 μm.

In one embodiment, the hair loss treatment agent/drug of the present invention is finasteride or dutasteride.

In one embodiment, the microspheres of the present invention may comprise biodegradable polymer and finasteride in a weight ratio of 3:1 to 9:1, preferably 4:1. When the weight ratio of the biodegradable polymer and the finasteride is less than 3:1, the shape-retaining force of the biodegradable polymer may be weakened, resulting in the biodegradable polymer and the finasteride in the microspheres being unevenly distributed. In addition, when the weight ratio of the biodegradable polymer and the finasteride exceeds 9:1, that is, the finasteride content in the microspheres is small, a large amount of microspheres should be administered in order for the treatment of be effective, which, in turn, would cause discomfort to the patient. More specifically, the biodegradable polymer in the biodegradable polymer-phase solution contains 10 to 20 wt %, preferably 15 wt %, but is not limited to the above examples.

In one embodiment, the microspheres of the present invention are capable of continuously releasing the finasteride for one to three months in the body.

In one embodiment, the biodegradable polymer of the present invention is selected from the group consisting of polylactic acid, polylactide, polylactic-co-glycolic acid, polylactide-co-glycolide (PLGA), polyphosphazine, polyiminocarbonate, polyphosphoester, polyanhydrides, polyorthoesters, polycaprolactones, polyhydroxyvalates, polyhydroxybutyrates, polyamino acid, and combinations thereof.

In one embodiment, the microspheres of the present invention are prepared using the basic droplet-based HCMMM microsphere manufacturing method described above with reference to FIG. 2, wherein the mixture of the solvent, the hair loss preventive agent/drug and the biodegradable polymer are properly mixed/dissolved in the biodegradable polymer-phase solution.

In one embodiment, the microspheres of the present invention are formed using the mass production apparatus described with reference to FIGS. 16 to 31.

[Product Example]—Preparation of the Microspheres for Use in Hair Loss Preventives, Including Therein Finasteride The size of the microspheres for subcutaneous injection in human was set to be 50 μm and the size limit to be from 20 to 70 μm considering the biodegradation period, drug delivery rate and injectability of the microspheres, and the concentration of the biodegradable polymer and finasteride was set as follows.

The biodegradable polymer-phase solution was prepared by dissolving polylactide-co-glycolide (PLGA) and finasteride in dichloromethane. At this time, the concentration of polylactide-co-glycolide in the biodegradable polymer-phase solution is 15 wt %, and the weight ratio of polylactide-co-glycolide and finasteride is set at 4:1.

The water-phase solution was prepared by dissolving polyvinyl alcohol (PVA) as the surfactant in pure water at a concentration of 0.25 wt %.

In the mass production apparatus, one side of the microchannels, i.e., the width or the depth or both, in the multichannel microsphere forming unit 100 was set to be 50 μm, in accordance with the basic principles developed.

The water-phase solution and biodegradable polymer-phase solution were introduced into the microchannels formed on a silicon wafer. The flow rate of the water-phase solution was adjusted while holding the flow rate of the biodegradable polymer-phase solution constant until the diameter of the microspheres formed reaches the target diameter, i.e., 50 μm.

Then, the size of the microspheres formed was fine-tuned by adjusting the flow rate of the biodegradable polymer phase solution while the flow rate of the aqueous solution was kept constant.

Referring to FIG. 16, the flow rate of water-phase solution and the flow rate of the biodegradable polymer-phase solution in the multichannel forming unit 100 are adjusted using the flow rate control unit 200.

The temperature of the water-phase solution and the biodegradable polymer-phase solution were maintained at 15° C.

The microspheres in the product reservoir 600 (see FIG. 16) were collected. Thereafter, the solvent, e.g., dichloromethane, was first extracted from the collected microspheres. After filtering the water-phase solution containing the microspheres, the residual surfactant and solvent, e.g., PVA and dichloromethane, were removed from the microspheres through washing before being dried, resulting in the formation of the desired monodisperse biodegradable polymer-based microspheres.

The microspheres formed in the product reservoir 600 (see FIG. 16) were collected to be stirred. There are three stirring stages. The first stage stirring was carried out at a speed of 1000 rpm for 1 and half hours at 15° C., followed by the second stage stirring, at a temperature of to 20° C., at a speed of 1000 rpm for 1 hour and finally, the third stage stirring, a temperature of 25° C. at a speed of 1000 rpm for 1 hour.

The desired microspheres were obtained by washing several times the microspheres that underwent the three stirring stages with purified water and by lyophilizing the microspheres that underwent the washing stages.

[Comparative Example]—Oral Hair Loss Treatment Agent/Drug 7.5 mg of hydroxypropyl beta cyclodextrin was dissolved in 100 mg of ethanol. 5 mg of finasteride was dissolved in a mixed solution in which hydroxypropyl beta cyclodextrin was dissolved in ethanol and dried at 40° C. for 12 hours. After drying, the dried material was sieved using a screen (30 mesh), 172.5 mg of microcrystalline cellulose was added and mixed to prepare a mixture. 5 mg of magnesium stearate was added to the mixture, and the mixture was then tabulated to prepare the treatment agent/drug in an oral dosage form.

CONCLUSION

As with other microparticle engineering technologies, however flexible the methodology may be, it must still aim to contend with existing large-scale manufacturing processes, and the HCMMM processing platform and method described hereinabove can handle the issues of scale-up and industrial-scale manufacture in unique way. The HCMMM processing platform of the present invention can produce monodisperse microspheres in precision engineered, microfluidic circuits. Working alone, a single fluidic circuit may produce only small volumes of particles. Yet with intelligent fluid distribution and handling described in the present invention, it may become possible to integrate the single fluid circuits to produce massively parallel arrays of circuits. The HCMMM processing platform and method of the present invention make it possible to mass produce monodisperse microspheres with an overall product size distribution of usually less than 1% in a considerably less space and at considerably lesser cost, as compared to conventional processes used therefor.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications and patent documents cited in this application are incorporated by reference in their entirety for all purposes to the same extent as if each individual publication or patent document were so individually denoted.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method for design optimization of an apparatus for a large-scale production of monodisperse microspheres and biodegradable polymer-based drug delivery systems and process optimization using therewith, wherein the apparatus comprising a multichannel microsphere forming unit for initially generating the monodisperse microspheres and biodegradable polymer-based drug delivery systems of a desired diameter and shape including therein at least two microchannels with a fixed dimension and at least two solutions, one solution known as a first solution and the other, a second solution, the first solution and the second solution being immiscible with respect to each other, one of the solutions including at least one biodegradable polymer dissolved therein in a predetermined amount, respectively known as a biodegradable polymer concentration, and the other solution including at least one surfactant dissolved therein in a predetermined amount, respectively known as a surfactant concentration, each of the solutions flowing in the respective microchannel at a constant flow rate, known respectively as a biodegradable polymer solution flow rate and a surfactant solution flow rate, the microchannels flowing therein the biodegradable polymer solution and the surfactant solution merging with each other at a merging point at an angle, known respectively as the merging angle, to form an outflow microchannel, resulting in the formation of monodisperse microspheres at the merging point having the desired diameter and shape including therein the biodegradable polymers, the monodisperse microspheres flowing out of the apparatus through the outflow microchannel along with the biodegradable polymer solution and the surfactant solution, the formation of the monodisperse microspheres having the desired diameter and shape resulting from interaction of the immiscibility of the solutions with respect to each other, the presence of the surfactant and the concentration thereof in the surfactant solution, the concentration of the biodegradable polymer in the biodegradable polymer solution, the merging angle, wettability between the solutions and the microchannel walls, the flow rate of the biodegradable polymer solution and the surfactant solution and the dimension of the microchannels, the method involving an optimization of the factors mentioned above, the method further comprising:

(1) determining the biodegradable polymer to be used and a first solvent in which the biodegradable polymer is to be dissolved, resulting in the biodegradable polymer solution, and determine the surfactant to be used and a second solvent in which the surfactant is to be dissolved, resulting in the surfactant solution, in such a way that the solutions are to be immiscible with respect to each other;

(2) fixing a material on which the microchannels to be formed, resulting in fixing of the wettability;

(3) fixing the diameter of the microspheres to be formed;

(4) fixing the dimension of the microchannels to be formed on the material by determining a relationship between the dimension and the diameter of the microspheres to be formed by forming the microspheres by varying the channel dimension while holding constant the flow rate of the biodegradable polymer solution, the flow rate of the surfactant solution, the biodegradable polymer concentration, the surfactant concentration and the merging angle;

(5) forming the microchannels on the materials to be incorporated in the multichannel microsphere forming unit in such a way that each of the biodegradable polymer solutions and the surfactant solutions flowing in the respective microchannels to flow an identical distance from an inlet of the multichannel microsphere forming unit to an outlet thereof, resulting in the flow rates of the biodegradable polymer solution and the surfactant solution within the respective microchannels in the multichannel microsphere forming unit to remain constant therethroughout;

(6) determining a relationship between the flow rate of the surfactant solution on the diameter of the microspheres to be formed by forming the microspheres by varying the flow rate of the surfactant concentration while holding constant the channel dimension, the flow rate of the biodegradable solution, the biodegradable polymer concentration, the surfactant concentration, the merging angle;

(7) determining a relationship between the flow rate of the biodegradable polymer solution on the diameter of the microspheres to be formed by forming the microspheres by varying the flow rate of the biodegradable polymer concentration while holding constant the channel dimension, the flow rate of the surfactant solution, the biodegradable polymer concentration, the surfactant concentration and the merging angle;

(8) determining a relationship between the surfactant concentration on the diameter of the microspheres to be formed by forming the microspheres by varying the surfactant concentration while holding constant the channel dimension, the flow rate of the surfactant solution, the flow rate of the biodegradable polymer solution, the biodegradable polymer concentration and the merging angle;

(9) determining a relationship between the biodegradable polymer concentration on the diameter of the microspheres to be formed by forming the microspheres by varying the surfactant concentration while holding constant the channel dimension, the flow rate of the surfactant solution, the flow rate of the biodegradable polymer solution, the biodegradable polymer concentration and the merging angle;

(10) determining a relationship between the merging angle on the diameter of the microspheres to be formed by forming the microspheres by varying the merging angle while holding constant the channel dimension, the flow rate of the surfactant solution, the flow rate of the biodegradable polymer solution, the biodegradable polymer concentration and the surfactant concentration; and

(11) determining an optimum design of the apparatus, including therein the multichannel microsphere forming unit, for the large scale production of the monodisperse microspheres and biodegradable polymer-based drug delivery systems of the desired diameter and shape incorporating therein an optimum merging angle and an optimum dimension of the microchannels determined through which the biodegradable polymer solution and the surfactant solution flow and an optimum processes to be used therewith incorporating therein an optimum flow rates of the biodegradable polymer solution and an optimum concentrations of the biodegradable polymer and surfactant in the respective solutions determined, wherein the flow rate of the biodegradable polymer solution, the flow rate of the surfactant solution, and the microchannel dimension are fixed after the surfactant concentration, the biodegradable polymer concentration, and the material for the microchip are fixed, and after the flow rate of the surfactant solution is fixed, then the flow rate of the biodegradable polymer solution is fine-tuned until the diameter of the microspheres formed corresponds to the target diameter.

2. The method of claim 1, wherein the material is selected from the group consisting of: silicon in wafer form, glass, steel or hydrophobic polymer in wafer form.

3. The method of claim 1, wherein the dimension of the microchannels is directly proportional to the diameter of the microspheres to be formed, and wherein a linear relationship or close thereto exists between the dimension of the microchannels and the diameter of the microspheres formed.

4. The method of claim 1, wherein a cross-sectional area of the microchannels is within 30% of a cross sectional area of the microspheres formed.

5. The method of claim 1, wherein a cross-section of the microchannels is a square, the width being identical to the depth, and wherein the width and the depth of the microchannels is within 30% of the diameter of the microspheres formed.

6. The method of claim 1, wherein either one of a width or a depth of the microchannels is within 30% of the diameter of the microspheres.

7. The method of claim 1, wherein the multichannel microspheres forming unit incorporates therein a plurality of microchannels through which the respective biodegradable polymer solution and the respective surfactant solution flow at a constant flow rate.

8. The method of claim 1, wherein a ratio of the flow rate of the surfactant solution to the flow rate of the biodegradable polymer solution is between 2:1 to 100:1.

9. The method of claim 1, wherein in order for the flow rates of the biodegradable polymer solution and the surfactant solution to remain constant in the respective microchannels in the multichannel microsphere forming unit of the apparatus, the microchannels is formed in such a way that the microchannels for the biodegradable polymer solution to flow is of the same length and the microchannels for the surfactant solution to flow must also be of the same length.

10. The method of claim 9, wherein the multichannel microsphere forming unit comprises a first inlet manifold, a second inlet manifold, a plurality of first microchannels through which the biodegradable polymer solution flow, a plurality of second microchannels through which the surfactant solution flow, a plurality of merging points at which the first microchannels and the second microchannels merge and the formation of the microspheres initially takes place, a plurality of third microchannels through which a mixture of the biodegradable polymer solution, the surfactant solution and the microspheres formed at the merging points flow, and a product outlet, the first inlet manifold being in fluid communication with the plurality of first microchannels, the second inlet manifold being in fluid communication with the plurality of second microchannels, and the plurality of third microchannels being connected to a plurality of merging points and extending from the plurality of merging points to the product outlet.

11. The method of claim 10, wherein the number of the first microchannels, the second microchannels, the third microchannels and the merging points is identical, and wherein additional plurality microchannels can be introduced depending on final microsphere requirements.

12. The method of claim 1, wherein the merging angle is between 30° and 90°.

13. The method of claim 1, wherein an optimum/ideal surfactant concentration in terms of the effectiveness and the cost factor is between 0.15 weight % and 0.30 weight %.

14. The method of claim 1, wherein a linear relationship exists between the concentration of the surfactant in the surfactant solution and the microsphere diameter in a certain concentration range defined by an upper limit of the surfactant concentration and beyond the upper limit, the effect thereof on the microsphere diameter is minimal.

15. The method of claim 1, wherein the optimum biodegradable polymer concentration is between 5 weight % and 30 weight %.

16. The method of claim 15, wherein, in the concentration range specified, roughly a linear relationship exists between the concentration of the biodegradable polymer in the biodegradable polymer solution and the microsphere diameter, as defined by the relationship:

Microsphere Diameter=−0.408*(Biodegradable Polymer Concentration)+57.1 with a standard deviation of 0.8048.

17. The method of claim 16, wherein the relationship is to be used to fine tune the microsphere diameter.

18. The method of claim 1, wherein a strong linear relationship exists between the flow rate of the biodegradable polymer solution and the diameter, as defined by the relationship:

Microsphere Diameter=0.095*(Flow Rate)+38.387 with a standard deviation of 0.9999.

19. The method of claim 18, wherein the relationship defined above is to be used to fine tune the microsphere diameter.

20. The method of claim 1, wherein diameter of the microspheres is generally inversely linearly proportional to the flow rate of the surfactant solution, wherein, an increase in the flow rate results in a corresponding decrease in the diameter of the microspheres.

* * * * *

UNITED STATES PATENT AND TRADEMARK OFFICE
CERTIFICATE OF CORRECTION

PATENT NO. : 10,632,442 B2
APPLICATION NO. : 15/788930
DATED : April 28, 2020
INVENTOR(S) : Ju Hee Kim Page 1 of 1

It is certified that error appears in the above-identified patent and that said Letters Patent is hereby corrected as shown below:

On the Title Page

Item (54) and in the Specification at Column 1, Lines 1-5, Title:
Delete "APPARATUS FOR A MASS PRODUCTION OF MONODISPERSE BIODEGRADABLE POLYMER-BASED MICROSPHERES AND A MULTI-CHANNEL FORMING DEVICE INCOPORATABLE THEREIN"
And insert --OPTIMIZATION OF THE DESIGNING OF APPARATUS AND PROCESSES FOR MASS PRODUCTION OF MONODISPERSE BIODEGRADABLE POLYMER-BASED MICROSPHERES AND BIODEGRADABLE POLYMER-BASED DRUG DELIVERY--
therefor.

Signed and Sealed this
Eighteenth Day of August, 2020

Andrei Iancu
*Director of the United States Patent and Trademark Office*